US008715951B2

(12) United States Patent
Parhami-Seren et al.

(10) Patent No.: US 8,715,951 B2
(45) Date of Patent: *May 6, 2014

(54) HIGHLY SENSITIVE IMMUNOASSAYS AND ANTIBODIES FOR DETECTION OF BLOOD FACTOR VIII

(75) Inventors: Behnaz Parhami-Seren, So. Burlington, VT (US); Kenneth G. Mann, Grand Isle, VT (US); David N. Fass, Rochester, MN (US)

(73) Assignee: The University of Vermont and State Agriculture College, Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,246

(22) Filed: Jul. 18, 2012

(65) Prior Publication Data

US 2013/0115621 A1   May 9, 2013

Related U.S. Application Data

(63) Continuation of application No. 11/988,518, filed as application No. PCT/US2006/027409 on Jul. 13, 2006, now Pat. No. 8,236,518.

(60) Provisional application No. 60/699,584, filed on Jul. 15, 2005, provisional application No. 60/715,978, filed on Sep. 9, 2005.

(51) Int. Cl.
*C12Q 1/56* (2006.01)
*G01N 33/86* (2006.01)
*C12N 5/07* (2010.01)
*G01N 33/53* (2006.01)

(52) U.S. Cl.
USPC .............. 435/13; 435/7.1; 435/7.4; 435/7.94; 435/69.6; 435/337; 435/962; 436/517; 436/523; 436/547; 436/548; 436/69; 436/175; 436/177; 436/811

(58) Field of Classification Search
USPC .......... 435/7.1, 7.2, 7.92, 7.94, 13, 69.6, 962; 436/517, 524, 528, 547, 548, 69, 175, 436/177, 811, 523
See application file for complete search history.

(56) References Cited

U.S. PATENT DOCUMENTS

| | | | | |
|---|---|---|---|---|
| 4,795,806 | A * | 1/1989 | Brown et al. | 530/383 |
| 7,855,274 | B2 | 12/2010 | Fay et al. | |
| 8,236,518 | B2 * | 8/2012 | Parhami-Seren et al. | 435/13 |
| 2003/0170613 | A1 | 9/2003 | Straus | |
| 2003/0224477 | A1 * | 12/2003 | Heartlein et al. | 435/69.1 |

OTHER PUBLICATIONS

Precup et al. A Monoclonal Antibody to Factor VIII Inhibits von Willebrand Factor Binding and Thrombin Cleavage, Blood (1991), 77 (9): pp. 1929-1936.*
Precup, et al., "A Monoclonal Antibody to Factor VIII Inhibits von Willebrand Factor Binding and Thrombin Cleavage," Blood. 1991, 77(9): pp. 1929-1936.
International Search Report for PCT/US06/27409 issued Jan. 15, 2007 and mailed Apr. 23, 2007.

* cited by examiner

*Primary Examiner* — Gail R Gabel
(74) *Attorney, Agent, or Firm* — Edwards Wildman Palmer LLP; David G. Conlin; Lisa Swiszcz

(57) ABSTRACT

Disclosed are antibodies that selectively bind to blood coagulation factor FVIII, and highly sensitive immunological assays comprising these antibodies. Preferred assays can detect FVIII at about 3500-fold below the normal physiological levels, and have a wide array of applications including accurate monitoring of FVIII concentration in pharmaceutical products for treatment of blood coagulation disorders, and determination of FVIII levels in plasma of human patients, including those with blood coagulation disorders such as hemophilia.

14 Claims, 34 Drawing Sheets

HIGHLY SENSITIVE IMMUNOASSAYS AND ANTIBODIES FOR DETECTION OF BLOOD FACTOR VIII

CROSS-REFERENCE TO RELATED APPLICATIONS

The present application is a continuation of U.S. national phase application Ser. No. 11/988,518, filed Apr. 21, 2009, now U.S. Pat. No. 8,236,517, pursuant to 35 U.S.C. §371, of PCT international application Ser. No. PCT/US2006/027409, filed Jul. 13, 2006, designating the United States and published in English, which claims the benefit of the following U.S. Provisional Patent Application Ser. No. 60/699,584 entitled "Highly Sensitive Immunoassays and Antibodies for Detection of Blood Factor VIII," filed Jul. 15, 2005, and U.S. Provisional Patent Application Ser. No. 60/715,978 of the same title, filed Sep. 9, 2005, the disclosures of which are hereby incorporated by reference in their entireties.

STATEMENT OF U.S. GOVERNMENT INTEREST

This invention was made with government support under Grant Nos. HL-46703 and RO3 A1057727 awarded by the National Institutes of Health. The Government has certain rights in the invention.

FIELD OF THE INVENTION

The invention generally relates to compositions and methods for detecting and quantifying levels of proteins present in bodily fluids such as blood, plasma or serum. More particularly, it relates to antibodies that selectively bind to blood coagulation factors such as FVIII, and immunological methods of using these antibodies in assays to detect these factors in body fluids of patients, including those with blood coagulation disorders such as hemophilia.

BACKGROUND

Blood clotting begins when platelets adhere at a lesion site in the cut wall of an injured blood vessel. In a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Co-factors are required at most of the steps.

The human factor VIII (FVIII) is a plasma glycoprotein that acts as a cofactor for the serine protease factor FIXa to activate FX in the intrinsic cascade of blood coagulation. Factor VIII circulates as an inactive precursor at a very low concentration in blood, bound tightly and non-covalently to von Willebrand factor. Factor VIII is proteolytically activated by thrombin or factor Xa, which dissociates it from von Willebrand factor and activates its procoagulant function in the cascade (Hoyer, 1981; Kane and Davie, 1988). In its active form, the protein FVIIIa is a cofactor that increases the catalytic efficiency of factor IXa toward factor X activation by several orders of magnitude.

Quantitative or qualitative deficiency in FVIII results in a bleeding disorder called hemophilia A (Scandella et al., 1998; Rick et al., 2003). Severe hemophiliacs number about 17,000 in the United States. These patients can suffer uncontrolled internal bleeding that may result in serious symptoms ranging from inflammatory reactions in joints to early death. These patients can be treated with human FVIII, which will restore the blood's normal clotting ability if administered with sufficient frequency and concentration. Hemophiliacs require daily replacement of factor VIII to prevent bleeding and the resulting deforming hemophilic arthropathy.

Several commercial preparations of human plasma-derived FVIII of varying degrees of purity are available for the treatment of hemophilia A. These products are derived from blood plasma of human donors treated to remove viruses, or prepared by recombinant means from cultures of cells that carry genetically engineered recombinant (r) full-length or truncated FVIII (Brackmann et al., 1993; Lusher et al., 1993); Bihoreau et al., 1991; Pipe and Kaufman, 1997; Sandberg et al., 2001).

Unfortunately, human factor VIII is unstable at physiologic concentrations and pH, and is present in blood at an extremely low concentration. Problems in therapeutic use occur due to difficulty in isolation and purification, immunogenicity, and the necessity of removing the AIDS and hepatitis infectivity risk.

Accurate assessment of the quantity and quality of FVIII is critical to successful outcome in hemophilia patients undergoing FVIII replacement therapy. Current assays of quantification of FVIII products and concentrates involve bioassays including clotting assays and generation of FXa (Langdell et al., 1953; Niemetz and Nossel, 1969; Over, 1986; Kemball-Cook et al., 1993). Thus currently available assays measure FVIII concentration only indirectly (Hoyer, 1981; Kane and Davie, 1988; Chavin and Fay, 1989; Foster and Zimmerman, 1989; Fay, 1993; Lenting et al., 1998). Unfortunately such indirect assays exhibit problems of poor reproducibility and lack of precision due to complex reaction kinetics.

A particular problem associated with FVIII preparations is the presence of FVIII degradation product. This is undesirable for several reasons. First, much more FVIII is required to achieve a desired therapeutic goal. Also, degradation products can interfere with FVIII function by interacting with substrate proteins, reducing the efficiency of FVIII activation by the substrates. Use of excess FVIII in patients is also undesirable as it can enhance production of neutralizing FVIII-specific antibodies (Scandella et al., 1998; El Alfy et al., 2000; Klinge et al., 2001; Lindgren et al., 2002). Available bioassays for FVIII reflect only the concentration of fully functional FVIII. Thus, if FVIII preparations contain degraded or inactive FVIII, such products are not detectable by bioassays.

To enhance ability to precisely assess the quality of FVIII preparations in a timely and cost effective manner, there exists a clear need for sensitive assays that can determine both the concentration and the biological activity of FVIII in FVIII preparations.

As discussed, FVIII is present in the blood of normal subjects at a very low concentration (about 100-700 pM). In severe hemophilia patients, FVIII concentrations are below 1% physiological concentration. Such low FVIII concentrations are below the level of detection of existing assay methods. A great improvement in the diagnosis and management of hemophilia patients would be achieved if it were possible to accurately measure FVIII levels in the plasma of these patients. Thus both for monitoring FVIII levels in patients suspected of having a blood clotting disorder, and in severe, moderate, and mild hemophilia patients undergoing FVIII replacement therapy, there is an unmet need for highly specific and sensitive assays that can detect FVIII at physiological concentrations and significantly below.

SUMMARY OF THE INVENTION

The invention provides highly sensitive immunoassays and antibodies capable of accurate detection of FVIII concentration in the plasma of normal human subjects and those with hemophilia. Levels of detection exhibited by particular embodiments greatly exceed those of previously described assays, for example by at least 3400-fold. The enhanced sensitivity of the assays is contributed in part by using a combination of two antibodies that can bind human FVIII protein in plasma with high affinity and selectivity following treatment with an agent that causes the FVIII to dissociate from FVIII-binding molecules to which it is bound, such as Von Willebrand factor (vWF).

Preferred antibodies of the invention are monoclonal and specifically bind an epitope on the Heavy-chain, B-domain or Light-chain of native human FVIII protein. Binding affinities ($IC_{50}$) of preferred antibodies are in the range of 50-160 nM FVIII. Antibodies of the invention are particularly useful in in vitro assays to detect and quantitate free FVIII or FVIII fragments and FVIII in complex with vWF in a laboratory or biological sample including a body fluid. These factors can be detected in the picomolar range in human plasma and in sub-picomolar concentrations in commercial products containing these factors.

Antibodies of the invention can be used to prepare substantially pure native FVIII, particularly native human FVIII from a biological sample.

Antibodies of the invention can also be employed as a component of a diagnostic kit, e.g., for detecting and preferably quantifying native FVIII in a biological sample, such as plasma from normal individuals or a human subject with a bleeding disorder.

Further provided are novel immunoassays that in some embodiments are at least 3400-fold more sensitive than existing assays and can measure FVIII concentrations as less than 1 pM in a biological sample such as human plasma.

A method for detecting a FVIII protein or a fragment thereof in a sample in accordance with the invention includes: (a) contacting a sample comprising FVIII protein with a reducing agent that releases FVIII from a FVIII-binding molecule; (b) contacting the sample of step (a) with a first (capture) antibody directed to a FVIII antigen such that the FVIII protein or fragment binds to the antibody and forms a complex therewith; (c) contacting the complex formed in step (b) with a second (probe) antibody directed to a FVIII antigen, the probe antibody being labeled with a detectable marker, to form a complex which includes the antibody of step (b), the FVIII protein or fragment, and the second antibody; and (d) detecting the second antibody in the complex formed in step (c), thereby detecting the FVIII protein or fragment in the sample. The method can be used to determine FVIII concentration in biological samples and commercial products comprising plasma.

In some embodiments of the assay, the reducing agent is selected from the group consisting of β-mercaptoethanol, sodium borohydride, dithiothreitol, erytritol, and ethane thiol.

A highly sensitive immunoassay in accordance with the invention, in which capture anti-FVIII antibodies are conjugated to fluorescent beads and probe antibodies are detected by flow analysis (e.g., using lasers, optics, micro-fluidics and advance signal processing) is sufficiently sensitive to be useful for determining FVIII levels in a human subject having or at risk of developing a blood clotting disorder such as hemophilia. Sensitivity of the assay is contributed in part by the very high binding affinity of a preferred capture antibody, and by ability of the anti-FVIII antibodies used in the assay to bind to FVIII protein under conditions in which the protein is dissociated from FVIII-binding molecules such as von Willebrand factor after treatment with a reducing agent. In a preferred embodiment of the method, the concentration of FVIII protein detectable in the sample is less than 1 pM.

Other aspects and advantages of the invention are discussed below.

BRIEF DESCRIPTION OF THE DRAWINGS

FIG. 1A shows detection by mAbs anti-FVIII-1, -20, and -21 and FIG. 1B shows detection by mAbs anti-FVIII-23, -25, and -68. FIG. 1C shows specificity of the immunoassay for human FVIII protein.

FIG. 7A shows a standard curve generated by immobilizing purified vWF on an anti-vWF mAb and detecting binding with a labeled second antibody. FIG. 7B shows quantification of vWF in commercial products containing FVIII using the immunoassay.

DETAILED DESCRIPTION OF THE INVENTION

Figure 1A:
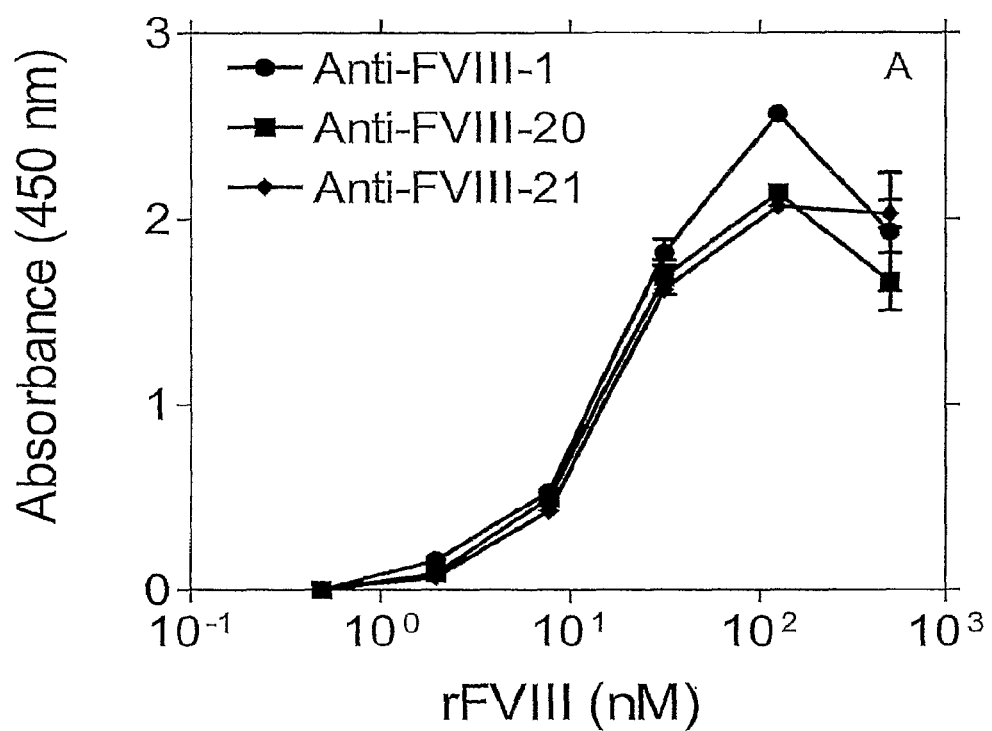
FIG. 1A-C is three graphs showing detection and quantification of blood factor VIII (FVIII) in a double sandwich enzymatic immunoassay (ELISA) according to an embodiment of the invention. Human FVIII protein is captured by a first anti-FVIII monoclonal antibody (mAb) (Fab)'$_2$ fragment, anti-FVIII-24. Binding of FVIII is detected by a second anti-FVIII mAb (as specified) and a horse peroxidase (HRP)-labeled anti-mouse FC fragment.

Human factor VIII (FVIII) is a plasma glycoprotein that acts as a cofactor of FIXa to activate FX in the intrinsic cascade of blood coagulation. As discussed, under normal circumstances FVIII circulates as an inactive precursor at a very low concentration in the blood, as a minor component tightly bound to a very large protein, the von Willebrand factor (vWF) (Hoyer, 1981; Kane and Davie, 1988). Detection of FVIII in human plasma by immunological methods is significantly complicated both by its very low concentration in biological fluids and particularly by its association with vWF. In one aspect, the invention newly addresses this problem by providing highly sensitive methods of detecting FVIII in a sample such as human plasma that in some embodiments exceed the sensitivity of existing immunoassays by a factor of 3400-fold or more. The methods derive their extreme sensitivity for FVIII from two interrelated discoveries. The first is that despite the noncovalent binding of FVIII to FVIII-binding molecules such as vWF, unexpectedly, reducing agents such as mercaptoethanol can be successfully used at low concentration (about 1-10 mM) to separate FVIII from these molecules. Importantly, this separation is effected without destruction of epitopes necessary for antibody recognition of FVIII. The second discovery is that anti-FVIII antibodies can be isolated and purified having the ability to bind FVIII with high specificity and affinity in the presence of such reducing agents. Accordingly, these antibodies can recognize and bind to epitopes in FVIII in its most accessible form, free from its natural binding partner, the much larger vWF. This feature greatly enhances the level of detection of FVIII achievable in fluid samples in which this protein is normally present at very low concentration, such as in plasma of healthy human subjects, and more particularly in that of patients with blood clotting disorders such as hemophilia, in which FVIII levels are extremely reduced.

Immunoassays for Detecting FVIII

In one important aspect, the invention provides a highly sensitive method for detecting a FVIII protein or a fragment thereof in a sample. The method includes the step of contacting a sample comprising FVIII protein with a reducing agent that irreversibly releases FVIII from a factor VIII-binding molecule. As discussed, the presence of such molecules that can bind to FVIII can interfere with FVIII detection in immunoassays. An example of a factor VIII-binding molecule is von Willebrand factor (vWF), with which FVIII is normally associated in the circulating blood of a subject. Any reducing agent can be employed in the method that can cause the separation of FVIII from vWF without destruction of antigenic sites on the FVIII molecule that are specifically recognized by antibodies used to detect FVIII in an immunoassay. Many reducing agents are known (e.g., β-mercaptoethanol, sodium borohydride, dithiothreitol, erytritol, ethane thiol) and those suitable for use in the invention can be determined empirically by testing for this quality in an immunoassay using particular anti-FVIII antibodies under consideration.

A preferred reducing agent for this purpose is β-mercaptoethanol. As shown below, pretreatment of both human plasma and samples containing recombinant FVIII (rFVIII) prior to immunoassay with this reducing agent at 1-10 mM concentration enables detection of FVIII at levels as low as 1 pM. See, for instance, Examples 8 and 9, infra.

As is apparent from the foregoing, a key aspect of the method for detecting a FVIII protein or fragment is the step of contacting the sample with an antibody directed to a FVIII antigen. In general, the method can be practiced with a wide variety of anti-FVIII antibodies. As described in more detail below, many forms of antibodies and fragments thereof are known. All of these can be used as anti-FVIII antibodies in the method. As also described below, in another aspect the invention provides monoclonal antibodies that possess unique qualities that render them particularly suitable for detection of FVIII in human plasma and in various FVIII-containing commercial products.

In a method of detecting FVIII, a first antibody of the subject invention is used as a "capture" antibody. The capture antibody is directed to an epitope on the FVIII protein or fragment thereof such that upon contact, the FVIII protein or fragment specifically binds to the antibody and forms a complex with it. In this manner the antibody "captures" the FVIII protein or fragment, removing it from the sample. As discussed, the capture antibody may be a monoclonal antibody or a polyclonal antibody.

The method further includes the use of a second (probe) antibody, also directed to a FVIII antigen. The epitope recognized by the probe antibody is different from the epitope recognized by the first (capture) antibody. Thus, upon binding to its recognition site on the captured FVIII protein molecule, the probe antibody contributes to a complex that includes the capture antibody and the probe antibody, with the FVIII protein or fragment sandwiched between the two anti-FVIII antibodies.

The probe antibody is generally labeled with a detectable marker. Detection of the FVIII protein in the complex is achieved by detecting the marker on the probe antibody. A wide variety of labels may be suitably employed to detectably-label the probe antibody, such as radionuclides, fluors, enzymes, enzyme substrates, enzyme cofactors, enzyme inhibitors, ligands such as, e.g., haptens, and the like. Detectable labels also include, but are not limited to, luminescent probes, radioisotopes, chromophores, fluorophores, or heavy metals. Anti-FVIII immunoglobulin linked to N-hydroxysuccinimidobiotin (i.e., biotin) can also be an effective probe for FVIII antigen when reacted with a detector (e.g., avidin, streptavidin or horseradish peroxidase). The peroxidase substrates identified above can be used to generate the color endpoint. The color detectors are most convenient but the invention is not so limited. Other detection systems including radioisotopic, luminescent, or electrochemical labels can also be employed. See also Examples below illustrating use of several detectable markers conjugated to anti-FVIII probe antibodies.

In some embodiments, the capture agents (antibodies) are immobilized, permanently or reversibly, on a solid support such as a bead, chip, or slide. In one embodiment, the capture agents are conjugated with a reporter molecule such as a fluorescent molecule or an enzyme, and used to detect the presence of bound FVIII on a substrate, for example, a "sandwich" type assay in which one capture agent is immobilized on a support to capture a FVIII antigen while a second, labeled antibody also specific for the captured FVIII may be added to detect/quantitate the captured FVIII. In some methods disclosed above, the detectable marker is preferably an enzyme. Preferred enzymes are horseradish peroxidase and alkaline phosphatase, although other enzymes known to those skilled in the art can also be used in the subject invention.

Numerous types of assays can be used in the subject invention as long as the configuration of the assay allows the antibodies to recognize the FVIII epitopes. Those skilled in the art to which the subject invention pertains would readily understand that any conventional immunoassay which would allow the recognition of the FVIII epitopes can be used in the subject invention to both quantitatively and qualitatively detect FVIII antigen. Such assays include regular sandwich assays, wherein an antigen is sandwiched between the bound antibody on a solid carrier and a labeled antibody; reverse sandwich assays, in which a labeled antibody is reacted with the antigen prior to contact with the bound antibody; and a simultaneous sandwich assay, in which the antibodies and the antigen are reacted simultaneously. These and other immunoassay methods can be used with the antibodies of the subject invention if they allow recognition by the antibodies of the FVIII epitopes.

The capture antibody, which is initially contacted with the FVIII-containing sample, may be attached to an immunological reaction surface. An immunological reaction surface is a surface that is insoluble in the reacting medium and on which immunological reactions take place, for example reactions involved in the enzyme-linked immunosorbent (ELISA) procedure. Typically the surfaces are glass, paper, or plastic, such as polystyrene or polyacrylate. The surface may be the interior surface of a test tube, the well of a microtiter plate or some other container suitable for an immunological reaction. Those skilled in the art will know of other appropriate surfaces on which an immunological reaction can take place and which can be used in the subject invention, such as glass or plastic beads or rods, or paper strips. For purposes of the subject invention, such an immunological reaction surface will be one to which the antibodies of the subject invention will adhere.

A particularly preferred surface is a bead or "microsphere" having physical characteristics and fluorescent properties suitable for use in applications such as flow cytometry. Beads suitable for use as a starting material in accordance with the invention are generally known in the art and may be obtained from manufacturers such as Spherotech (Libertyville, Ill.), Molecular Probes (Eugene, Oreg.) and Luminex (Austin Tex.). Once a homogeneous subset of beads is obtained, the beads are conjugated with a first anti-FVIII antibody of the invention. Preferably the bead comprises at least one appropriate fluorescing compound.

Flow analysis operates in a conventional manner. That is, the beads are processed by illuminating them, essentially one at a time, with a laser beam. Measurements of the scattered laser light are obtained for each illuminated bead by a plurality of optical detectors. In addition if a bead contains at least one appropriate fluorescing compound, it will fluoresce when illuminated. A plurality of optical detectors within the flow analyzer measure fluorescence at a plurality of wavelengths. Typical measured bead characteristics include, but are not limited to, forward light scatter, side light scatter, red fluorescence, green fluorescence, and orange fluorescence. An exemplary flow cytometric system for simultaneous assay of multiple analytes in a sample, including antigens bound to antibodies conjugated to fluorescent beads is marketed by Luminex (Austin, Tex.) and is described, for example, in U.S. Pat. No. 5,981,180, the disclosure of which is herein incorporated by reference in its entirety.

Figure 8:
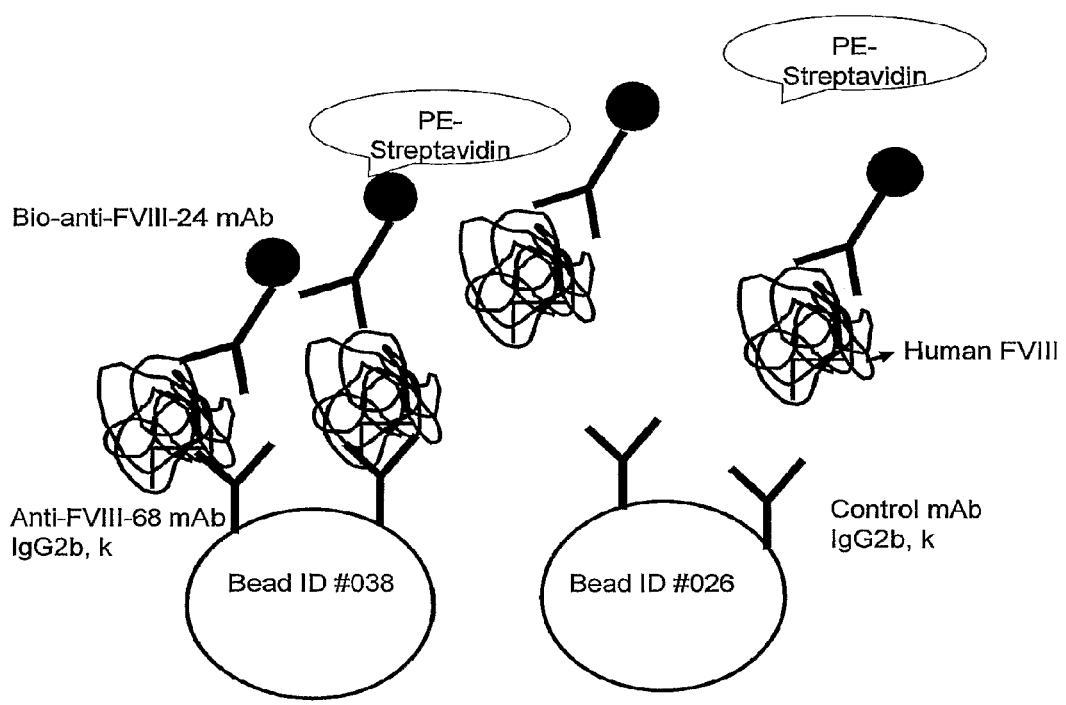
FIG. 8 is a schematic diagram illustrating a highly sensitive fluorescence-based immunoassay (FLI) for detection of FVIII, according to an embodiment of the invention.

As illustrated in FIG. 8, a particularly preferred highly sensitive method for detecting a FVIII protein or fragment comprises contacting a sample with an anti-FVIII capture antibody attached to a first (test) bead having at least one detectable characteristic, such as a first identifiable spectral property. As a control, the sample is contacted with an irrelevant antibody (i.e., an antibody of the same class having no binding affinity to FVIII) that is attached to a second (control) bead having at least one characteristic distinguishable from that of the first bead, such as a fluorescent bead having a second spectral property distinguishable by detectors in a flow analyzer from that of a first fluorescent bead to which a FVIII capture antibody is attached. Upon contact with the sample, FVIII in the sample complexes with the anti-FVIII capture antibody. In the case of the control beads, some proteins in the sample may form non-specific complexes with the control antibody. The complexes formed on the beads comprising capture anti-FVIII antibodies and on the beads comprising control antibodies (if such complexes form) are detected by contacting the respective beads with a second (probe) antibody directed to a FVIII antigen labeled with a detectable marker. Complexes which include the capture and control antibodies are then detected, and the amount of FVIII protein in the sample is determined by subtracting the non-specific binding detected by the probe antibody on the control beads from that of the specific binding detected by the probe antibody on the capture beads. Incorporation of this control ensures that spurious, non-specific binding can be screened for and subtracted from the determination of FVIII concentration.

Although immunoassays using antibodies attached to surfaces such as beads have been previously described, the inventors have discovered that particular conditions tailored to the specific anti-FVIII antibodies are necessary to achieve the very high levels of detection of FVIII protein in bead-based fluorescent immunoassays of the invention. Detailed exemplary protocols for attachment of FVIII antibodies to microspheres are provided infra, for instance in Examples 8 and 9. In general, several factors were found to be important to obtain a high yield of beads with appropriately conjugated antibodies, and to achieve the observed high level sensitivity of the bead-based FVIII immunofluorescent assay.

One important aspect is avoidance of methods such as vortexing and sonication throughout the procedures involving coupling of antibodies to beads. Use of these methods significantly reduces yields by causing the microspheres to disintegrate. Time and speed of centrifugation of beads is also important for recovery. A preferred centrifugation protocol is about 3 minutes at 11,000-12,000 rpm. It is also preferable to considerably increase the pH of the coupling buffer above that recommended by a commercial supplier (Luminex), to approximately pH 6.0. In addition, it is important that the concentration of the capture antibody incubated with the beads during the attachment step not be too high. For example, the inventors have determined that for anti-FVIII mAb-68 described herein, a preferred concentration is 5 µg/ml, which is significantly lower than the concentration (25 µg/ml) recommended, for example, by Luminex.

Immunological reaction conditions for the disclosed methods are conditions with respect to temperature, concentration, solvent, pH, etc., under which the immunological reaction such as the formation of an antibody/antigen complex will take place. Those skilled in the art are familiar with the parameters under which such complexes will form. They will know that the temperature cannot be so high or the pH so extreme as to inactivate the reactant. The solvent is typically a selected buffer or other carrier for the reactants. It may be plasma, serum or some fraction of these materials. The reaction products, including the intermediate reaction products of this invention, are soluble in the reaction solvent. Any suitable immunological reaction conditions which allow the recognition of the epitopes by the antibodies of the subject invention may be used in the methods of the invention. Further details of suitable immunological reaction conditions for specific immunoassays including ELISA, sandwich assays and bead-based fluorescent assays are described in Examples below.

The samples which can be analyzed using the methods of the subject invention can be obtained from any vertebrate species in which one is interested in determining the FVIII content of the sample. Preferably, the vertebrate species is a warm-blooded vertebrate species. Such warm-blooded vertebrate species include, but are not limited to, human, canine, porcine, bovine, guinea pig, horse, cat, monkey, sheep, rat, mouse, goat, rabbit, manatee, llama, chicken and camel. A particularly preferred subject is a human having or at risk of developing a bleeding disorder.

The sample which is analyzed using the subject invention is preferably a biological fluid. Suitable biological fluids include serum, plasma, cell lysates, urine, or products from a tissue culture cell. A person skilled in the art to which the subject invention pertains would readily understand that numerous other biological fluids from the vertebrate species can be used as samples in the subject assay. In preferred embodiments of the subject invention, however, the biological fluid comprises serum or plasma, with the most preferred biological fluid comprising blood plasma.

In addition to their uses for detection of FVIII in biological samples, the immunoassays of the invention are especially suitable for analysis of the concentration of FVIII in commercial products containing FVIII or recombinant FVIII (see, for instance, Examples 5-7 and Table III). A bead-based fluorescent immunoassay embodiment is particularly useful, due to its very high level of sensitivity in the picomolar range, for detection of FVIII in human plasma from normal subjects and those with blood clotting and autoimmune disorders, as described, for instance, in the Examples below.

Antibodies Directed to FVIII

In one aspect, the invention provides antibodies directed against FVIII protein or peptide antigens ("anti-FVIII antibodies"). As used herein, a "FVIII antigen" or "factor VIII antigen" means any portion of a FVIII protein or peptide that elicits an immune response. A preferred FVIII antigen is a sequence contained in a human FVIII protein.

Several preferred anti-FVIII antibodies useful, for example, as capture or probe agents in immunoassays for detection of VIII in fluids such as plasma include mouse monoclonal antibodies (mAb) directed against human FVIII protein. Preferred mouse monoclonal antibodies identified herein as anti-FVIII mAb clones 1, 24, 20, 21, 23, 25, and 68 have been extensively characterized, as further described below in Examples 2-4. A particularly preferred antibody is anti-FVIII mAb-24. A hybridoma cell line designated αFVIII-24 producing mAb-24 was deposited on Jul. 28, 2005, under Accession Number PTA-6890, with the American Type Culture Collection ("ATCC"), at 10801 University Boulevard, Manassas, Va. 20110-2209 USA, which is an International Depository Authority (IDA) listed in MPEP §2405 as being recognized under the Budapest Treaty on the International Recognition of the Deposit of Microorganisms for the Purposes of Patent Procedure. These deposits were made under the provisions of the Budapest Treaty and the regulations thereunder. All restrictions on the availability to the public of the deposited material will be irrevocably removed upon the granting of the patent, except for the requirements specified in 37 C.F.R. §1.808(b), and the term of the deposit will comply with 37 C.F.R. §1.806.

In some embodiments the capture agents are referred to as "first" antibodies. An antibody useful as capture or probe antibody for FVIII may be a full length antibody or a fragment thereof, which includes an "antigen-binding portion" of an antibody. The term "antigen-binding portion," as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv, scFv); see, e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology.

Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123).

Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

As discussed, anti-FVIII antibodies may be polyclonal or monoclonal. The terms "monoclonal antibodies" and "monoclonal antibody composition," as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition typically displays a single binding affinity for a particular antigen with which it immunoreacts.

Any art-recognized methods can be used to generate a FVIII directed antibody. For example, a FVIII protein or peptide (alone, or linked to a hapten or protein carrier) can be used to immunize a suitable subject, (e.g., rabbit, goat, mouse or other mammal or vertebrate). For example, the methods described in U.S. Pat. Nos. 5,422,110; 5,837,268; 5,708,155; 5,723,129; and 5,849,531 (the contents of each of which are incorporated herein by reference) can be used. The immunogenic preparation can further include an adjuvant, such as Freund's complete or incomplete adjuvant, or similar immunostimulatory agent. Immunization of a suitable subject with a FVIII protein or fragment thereof induces a polyclonal anti-FVIII antibody response. The anti-FVIII antibody titer in the immunized subject can be monitored over time by standard techniques, such as with an enzyme linked immunosorbent assay (ELISA) using immobilized FVIII protein or peptide. The antibody molecules directed against a FVIII antigen can be isolated from the immunized mammal (e.g., from the blood) and further purified by well known techniques, such as protein A chromatography to obtain the IgG fraction.

At an appropriate time after immunization, e.g., when the anti-FVIII antibody titers are highest, antibody-producing cells can be obtained from the subject and used to prepare, e.g., monoclonal antibodies by standard techniques, such as the hybridoma technique originally described by Kohler and Milstein (1975) Nature 256:495-497 (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol Today 4:72), or the EBV-hybridoma technique (Cole et al. (1985), Monoclonal Antibodies and Cancer Therapy, Alan R. Liss, Inc., pp. 77-96). The technology for producing monoclonal antibody hybridomas is well known (see generally, R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet. 3:231-36). Briefly, an immortal cell line (typically a myeloma) is fused to lymphocytes (typically splenocytes) from a mammal immunized with a FVIII immunogen as described above, and the culture supernatants of the resulting hybridoma cells are screened to identify a hybridoma producing a monoclonal antibody that binds a FVIII antigen.

Any of the many well known protocols used for fusing lymphocytes and immortalized cell lines can be applied for the purpose of generating an anti-FVIII monoclonal antibody (see, e.g., G. Galfre et al. (1977) Nature 266:55052; Gefter et al. Somatic Cell Genet.; Lerner, Yale J. Biol. Med.; Kenneth, Monoclonal Antibodies, cited supra). Moreover, one of ordinary skill will appreciate that there are many variations of such methods which also would be useful.

Typically, an immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine-("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from American Type Culture Collection (ATCC). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells. (Unfused splenocytes die after several days because they are not transformed.) Hybridoma cells producing a monoclonal antibody of the invention are detected by screening the hybridoma culture supernatants for antibodies that bind a FVIII antigen, e.g., using a standard ELISA assay.

Anti-FVIII antibodies in accordance with the invention can be characterized by one or more distinguishing features, which provide utility in different types of assays. As shown in Tables I and II, infra, useful monoclonal antibodies in accord with the invention can exhibit varying affinities for FVIII protein and can be directed to binding regions in the B-domain, H-chain, or L-chain of a FVIII protein.

Some embodiments of the antibodies of the subject invention are characterized by particularly strong binding affinity for FVIII protein. Useful binding affinities ($IC_{50}$) are in the range of about 50-160 nM FVIII. Some embodiments of antibodies in accordance with the invention are directed to an epitope in the H-chain or L-chain of FVIII (designated H/L) and exhibit a relative binding affinity ($IC_{50}$) in the range of about 50-103 nM. (See, e.g., Table 1, infra.) Other distinguishing features of antibodies of the subject invention are described in the Examples below.

In some embodiments, antibodies of the subject invention can be conjugated to a variety of pharmaceutical agents such as, e.g., drugs, enzymes, hormones, chelating agents capable of binding a radionuclide, as well as other proteins and polypeptides useful for diagnosis or treatment of disease. For diagnostic and other purposes, as discussed, the antibodies of the present invention can be used either detectably-labeled or unlabeled. For example, a wide variety of labels may be suitably employed to detectably-label the antibody, such as radionuclides, fluors, enzymes, enzyme substrates, enzyme cofactors, enzyme inhibitors, ligands such as, e.g., haptens, and the like.

Diagnostic methods are also contemplated including in vivo diagnostic imaging (see, e.g., A. K. Abbas, Cellular and Molecular Immunology, pg. 328 (W.B. Saunders Co. 1991)). For most in vivo imaging applications, an antibody of the invention can be detectably-labeled with, e.g., $^{125}I$, $^{32}P$, $^{99}Tc$, or other detectable tag, and subsequently administered to a mammal, particularly a human, for a pre-determined amount of time sufficient to allow the antibody to contact a desired target. The subject is then scanned by known procedures such as scintigraphic camera analysis to detect binding of the antibody. The analysis could aid in the diagnosis and treatment of a number of bleeding disorders such as those specifically disclosed herein.

Antibodies of the invention also can be used to prepare substantially pure (e.g., at least about 90% pure, preferably at least about 96 or 97% pure) native FVIII, particularly native human FVIII from a biological sample such as human plasma. For example, native FVIII can be obtained and purified by admixing the solution with a solid support comprising the antibody to form a coupling reaction admixture. Exemplary solid supports include a wall of a plate such as a microtiter plate, as well as supports including or consisting of polystyrene, polyvinylchloride, a cross-linked dextran such as Sephadex™. (Pharmacia Fine Chemicals), agarose, polystyrene beads, polyvinyl chloride, polystyrene, polyacrylamide in cross-linked form, nitrocellulose or nylon and the like. The FVIII can then be isolated from the solid support in substantially pure form in accordance with standard immunological techniques. See generally, Ausubel et al., Current Protocols in Molecular Biology, John Wiley & Sons, New York, (1989); Harlow and Lane in Antibodies: A Laboratory Manual, CSH Publications, NY (1988).

As also discussed above, antibodies of the invention can be employed to detect native human FVIII in a biological sample. Exemplary biological samples include blood plasma, serum, saliva, urine, stool, vaginal secretions, bile, lymph, ocular humors, and cerebrospinal fluid. Samples may be suitably obtained from a mammal suffering from or suspected of suffering from a bleeding disorder For such assays, as discussed above, an antibody of the invention can be detectably-labeled with a suitable atom or molecule e.g., radioactive iodine, tritium, biotin, or reagent capable of generating a detectable product such as an anti-iodiotypic antibody attached to an enzyme such as β-galactosidase or horseradish peroxidase, or a fluorescent tag (e.g., fluorescein or rhodamine) in accordance with known methods. After contacting the biological sample with the detectably-labeled antibody, any unreacted antibody can be separated from the biological sample, the label (or product) is detected by conventional immunological methods including antibody capture assay, antibody sandwich assay, RIA, ELISA, immunoprecipitation, immunoabsorption, immunoblotting and the like. Any label (or product) in excess of that detected in a suitable control sample is indicative of the presence of native FVIII in the biological sample. For example, antibodies of the invention can be detectably-labeled to detect, and preferably quantitate, native FVIII in accordance with immunological techniques as discussed above such as antibody capture assay, ELISA, antibody sandwich assay, RIA, immunoprecipitation, immunoabsorption, bead-based fluorescent assay and the like). See generally, Harlow and Lane and Ausubel et al., supra).

EXAMPLES

The invention is further illustrated by reference to the following non-limiting examples.

Example 1

Materials and Methods

The following materials and methods were used as needed to conduct studies outlined in Examples 1-10. Additional methodological details are included in Examples 11 and 12.

1. Proteins

Albumin-free rFVIII was used as our gold standard in all immunoassays and activity assays), Recombinate® (albumin-stabilized rFVIII), Hemofile-M® (plasma-derived, immunoaffinity purified vWF-containing FVIII), Immunate® (plasma-derived FVIII containing excess molar concentration of vWF), Refacto® (B-domain-deleted FVIII) and Kogenate (sucrose-stabilized rFVIII, Bayer Corporation, Elkhart, Ind.) were obtained from Baxter Healthcare Corporation, Westlake Village, Calif.). VWF (purified, MW of 250, 000) was a generous gift from Dr. Rick Jenny, Haematologic Technologies Inc., Essex Junction, Vt.).

2. Production of FVIII- and vWF-Specific Monoclonal Antibodies (mAbs)

Balb/C mice were used for immunization with plasma purified FVIII and vWF. Immunization protocols and mAb production methods were similar to those reported previously (Foster et al., 1982; Foster et al., Blood). FVIII light-chain specific mAb clone 68 (designated as F68) was a generous gift from Dr. David Fass (Mayo Clinic, Rochester, Min.).

3. Immunoassays

3a. Direct binding ELISA was used to determine the binding specificity of mAbs for FVIII. In such assays, wells of polyvinyl chloride (PVC) microtiter plate (Falcon, Becton Dikinson Labware, Franklin Lakes, N.J.) were coated over night with 50 µl of a solution of 5 µg/ml PBS (phosphate buffered saline (0.15 M NaCl, 0.1 M sodium phosphate, pH 7.2) of full-length rFVIII. Excess FVIII was removed by washing the wells with 1% bovine serum albumin fraction V (BSA, Sigma, St. Louis, Mo.) in PBS. Fifty µl of various dilutions of culture supernatants or increasing concentrations of purified mAbs were added to the pre-coated wells and incubated for 1 hr at room temperature using an orbital shaker. Following 3 washes to remove excess Ab, binding of mAb was detected using horse radish peroxidase (HRP) labeled goat anti-mouse Ig (Sigma) and a chromogenic substrate (KPL, Gaithersburg, Md.). The end point of reaction was determined after addition of 25 µl of 2 M phosphoric acid in a plate reader (Bio-Tek Instruments, Inc., Winooski, Vt.) at 450 nm.

3b. Competition ELISA was used to determine the relative apparent affinity of each mAb for FVIII. Wells of PVC microtiter plate were coated with 50 µl of 5 µg/ml PBS of rFVIII. First we determined mAb-containing culture supernatant dilution or mAb concentration that was not in excess of the immobilized antigen. Using the direct binding assay described above, the culture supernatant dilution or mAb concentration at which 50% binding was achieved was ascertained. Inhibition of binding of mAbs to FVIII was determined by adding 25 µl of mAb-containing culture supernatant or purified mAb (at 50% binding) and 25 µl of free rFVIII (0.6-400 nM, 2-fold dilutions). The percent inhibition is the ratio of $(OD_{450}$ in the presence of BSA-$OD^{450}$ in the presence of FVIII)/$(OD_{450}$ in the presence of BSA)×100. The relative affinity $(IC_{50})$ is the FVIII concentration (nM) that inhibits 50% of the binding of mAb to immobilized FVIII.

3c. Double sandwich mAb immunoassay was utilized for quantification of various FVIII products, FVIII-vWF preparations and determination of FVIII specific activity. In such assays, one FVIII-specific monoclonal (Fab)$'_2$ fragment was immobilized in the wells of microtiter plate. Various dilutions or concentrations (10-0.04 nM, 3-fold dilutions) of FVIII or FVIII-vWF complex were added to the pre-coated wells. FVIII binding was probed with a different FVIII-specific mAb or anti-vWF mAb. Binding of this second mAb was detected using HRP-anti-mouse FC (Sigma) and a chromogenic substrate as described above. Unless it is specified all FVIII immunoassays were carried out in the presence PBS.

3d. A double Ab sandwich assay was utilized to determine concentration of vWF in FVIII concentrates. In such assay purified vWF or FVIII concentrates containing vWF were immobilized in the wells of microtiter plate pre-coated with anti-vWF mAb. Protein binding was probed using goat anti-human vWF (also a gift from Dr. Rick Jenny) and HRP-rabbit anti-goat Ig (Southern Biotechnology Associates, Inc., Birmingham, Ala.).

4. FVIII Activation Using Thrombin

Activated FVIII (FVIIIa) was used in experiments involving epitope mapping and for dissociation of FVIII-vWF complex. Forty µg rFVIII (6.5 µl of 0.62 mg/ml FVIII) was added to 12.2 µl of HBS buffer (HEPES buffered saline, 0.15 M NaCl, 0.02 M HEPES, pH 7.4) containing 0.1% polyethylene glycol (PEG, MW 8000, Sigma) and 2 mM $CaCl_2$. Alpha thrombin (generous gift from Hematologic Technologies Inc.) at final concentration of 20 nM (2.8 NIH units) was added and was incubated for 5 minutes at room temperature. The reaction was terminated by addition to final concentration of 20 mM EDTA and 10 µM PPACK (Phe-Pro-Arg-chloromethyl Ketone, Sigma). Activation of FVIII was confirmed by coagulation assay using Automated APTT (activated partial thromboplastin time) according to the manufacturer's protocol (bioMérieux, Inc., Durham, N.C.) and by immunoblotting as described below.

5. Preparation of FVIII-vWF Complex

Twenty nM FVIII was mixed with 40 nM vWF in HBS buffer containing 2 mM $Cl_2Ca$. The mixture was incubated for 5 minutes at 37° C. in a water bath. Various concentrations (0.082-20 nM) were used for immunoassays.

6. Immunoblotting

Immunoblotting was utilized as a complementary approach to assess the blotting capabilities and epitope specificity of each mAb shown in Table I. Immunoblotting was also used determine FVIII concentration in commercial preparations, and to confirm FVIII activation. Various concentrations of FVIII were electrophoresed on a gradient SDS-PAGE (5-15%) and subsequently transferred onto nitrocellulose membranes. Membranes were first blocked in 10% non-fat dry milk in PBS-0.05% Tween 20 and then reacted with FVIII heavy chain (H), light chain (L) and B-domain specific mAbs. Binding was probed with HRP-sheep anti-mouse Ig (Amersham Life Science, Arlington Heights, Ill.). Proteins were detected with enhanced chemiluminescence (ELC) Western blotting detection reagents (Amersham Life Sciences, Piscataway, N.J.).

Example 2

Immunological Characterization of FVIII-Specific mAbs

Monoclonal antibodies against Factor VIII were prepared as described in Methods. From eighteen stable clones produced, six clones (designated M1 and M20-M25) were selected for further characterization. Immunological characteristics of these clones are shown in Table I. Immunological properties of anti-FVIII mAb clone 68 (F68, see Methods) is also included in the Table I. A hybridoma cell line designated αFVIII-68 producing mAb-68 was deposited on Jul. 28, 2005, under Accession Number PTA-6891, with the American Type Culture Collection ("ATCC").

As shown in Table I, all FVIII clones exhibited apparent affinities in the range of 49-160 nM. Two clones (M1 and F68) could be used in immunoblotting for structural analysis of full-length FVIII and FVIII fragments, and for epitope mapping. Clone F68 binds to protein A; thus binding of this mAb to FVIII could be probed by both HRP-anti-mouse Ig and HRP-protein A.

TABLE I

Immunological characteristics of FVIII-specific clones

| Clone | Relative Affinity, IC50(nM)[a] | Protein A binding[b] | Immunoblot[c] | Isotype[d] | Binding region[e] |
|---|---|---|---|---|---|
| M1 | 160 | − | + | IgG1, κ | B-domain |
| M20 | 90 | − | − | IgG1, κ | Heavy or light chain |
| M21 | 50 | − | − | IgG1, κ | Heavy or light chain |

TABLE I-continued

Immunological characteristics of FVIII-specific clones

| Clone | Relative Affinity, IC50(nM)[a] | Protein A binding[b] | Immunoblot[c] | Isotype[d] | Binding region[e] |
|---|---|---|---|---|---|
| M23 | 100 | − | − | IgG1, κ | Heavy or light chain |
| M24 | 103 | − | − | IgG1, κ | Heavy or light chain |
| M25 | 49 | − | − | IgG1, κ | Heavy or light chain |
| F68 | 60 | + | + | IgG2b, κ | Light chain |

[a]Relative affinity was determined using competition solid-phase ELISA. Binding of murine anti-FVIII mAbs (mAb concentration which was not in excess of immobilized antigen i.e., equivalent to 30-50% binding to rFVIII) to immobilized rFVIII was determined in the absence or presence of various concentrations (1-200 nM) of free soluble rFVIII. Binding was determined using HRP-anti-mouse Ig. IC50 is FVIII concentration that inhibits 50% of the binding of mAb to immobilized FVIII.
[b]Protein A (PA) binding was determined using solid-phase ELISA. Wells of the microtiter plate were coated with FVIII. Binding of mAbs to immobilized FVIII was determined using HRP-PA.
[c]FVIII was subjected to SDS-gel electrophoresis under non-reducing conditions and transferred onto nitrocellulose paper. Binding of mAbs to FVIII was probed using HRP-anti-mouse Ig and chemiluminescence detection reagents.
[d]Isotype of each mAb was determined using solid-phase ELISA in which binding of mAbs to immobilized FVIII was determined using rabbit-anti-mouse isotype specific Abs and HRP-anti-rabbit Ig.

Example 3

Double Sandwich Immunoassays Comprising FVIII-Specific mAbs

Figure 1B:
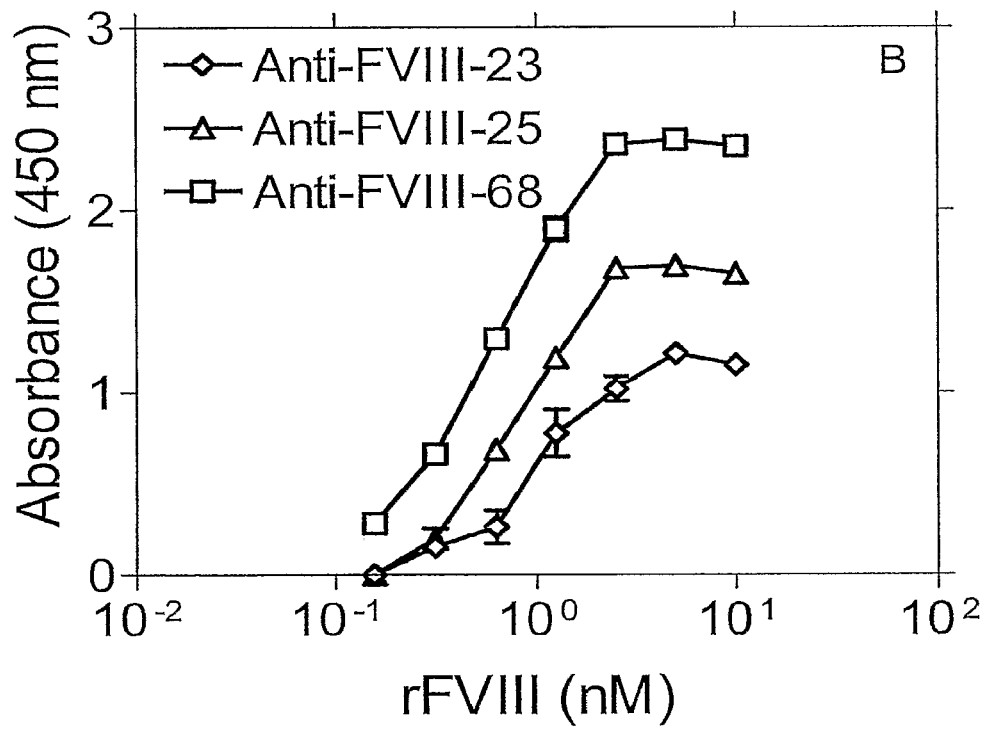

In an exemplary double sandwich mAb assay, F(ab)'2 fragment from clone 24 was immobilized in the wells of microtiter plates. Binding of FVIII to mAb 24 was detected using different anti-FVIII-specific mAbs as shown in FIGS. 1A and 1B. More particularly, FIGS. 1A and 1B show immunoassays in which recombinant Factor VIII (rFVIII) was captured using anti-FVIII-24 mAb(Fab)'2 fragment. Binding of rFVIII was detected with one of the anti-Factor VIII mAbs as indicated, i.e., anti-FVIII-1, -20 and -21 mAbs (FIG. 1A) or anti-Factor VIII-23, 25, or -68 mAbs (FIG. 1B).

Figure 1C:
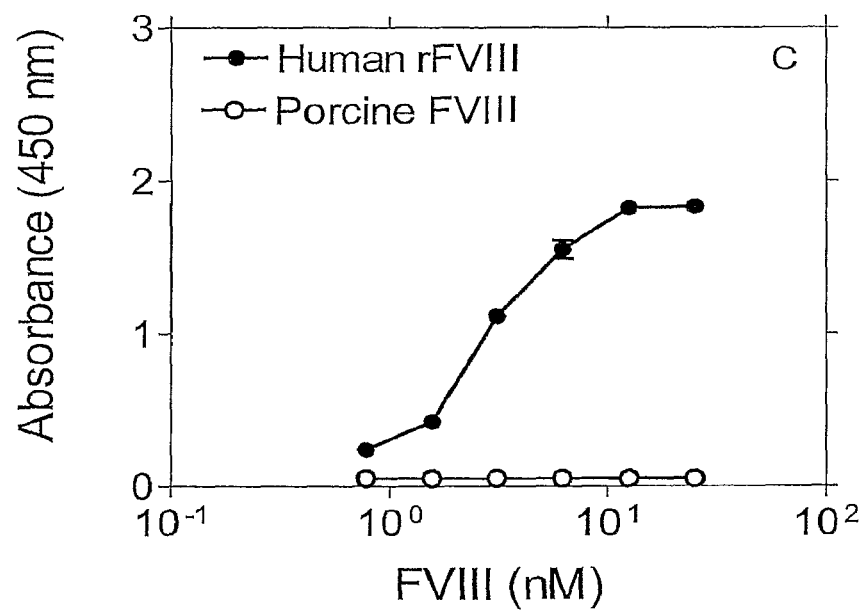

Binding specificity of anti-FVIII mAbs was confirmed using porcine FVIII as compared with human FVIII. A representative curve is shown in FIG. 1C in which binding of FVIII to immobilized anti-FVIII-24 (Fab)'2 was probed with anti-FVIII-20 mAb. Human or porcine FVIII bound to anti-FVIII-24 mAb (Fab)'2 fragment was probed with anti-FVIII-20 mAb and HRP-anti-mouse FC fragment. The results show that the immunoassay detects human, but not porcine, FVIII.

Example 4

Epitope Mapping of Anti-FVIII mAbs

Using immunoassays and various forms of FVIII, epitope mapping was performed to localize the binding specificity of anti-FVIII mAbs. Table II summarizes the binding specificity of mAbs for full-length FVIII, FVIIIa, B-domain less FVIII and FVIII-vWF complex. Details of the epitope mapping for individual monoclonal antibodies are described infra.

TABLE II

Epitope specificity of anti-FVIII mAbs[a]

| Clone[b] | rFVIII | rFVIIIa | ReFacto (B-domain less) | FVIII-vWF[c] | Binding region[d] |
|---|---|---|---|---|---|
| 1 | + | − | − | − | B-domain |
| 24 | + | + | + | + | H/L-chain |
| 23 | ± | + | + | − | H/L-chain |
| 20, 21, 25 | + | + | + | − | H/L-chain |
| 68 | + | ± | + | − | L-chain |

[a]Binding specificity of anti-FVIII mAbs was determined using double mAb sandwich assay as described in FIG. 1. In all assays, mAb 24 was used for capture of FVIII products.
[b]Immunological characteristics of FVIII-specific mAbs are described in Table I.
[c]FVIII-vWF complex was prepared by mixing 20 nM FVIII with 40 nM vWF as described in Methods.
[d]Binding region was deduced from the results of immunoassay and immunoblotting. H/L designates heavy or light chain.

Anti-FVIII-1 mAb. Following capture of the FVIII proteins by mAb 24, anti-FVIII-1 mAb bound to full-length FVIII but it did not react with FVIIIa or ReFacto. This result indicates that the binding region of mAb 1 is located in the B-domain. As shown in Table II, Clone 1 epitope is sterically hindered when FVIII is in complex with vWF.

Figures 2A, 2B:
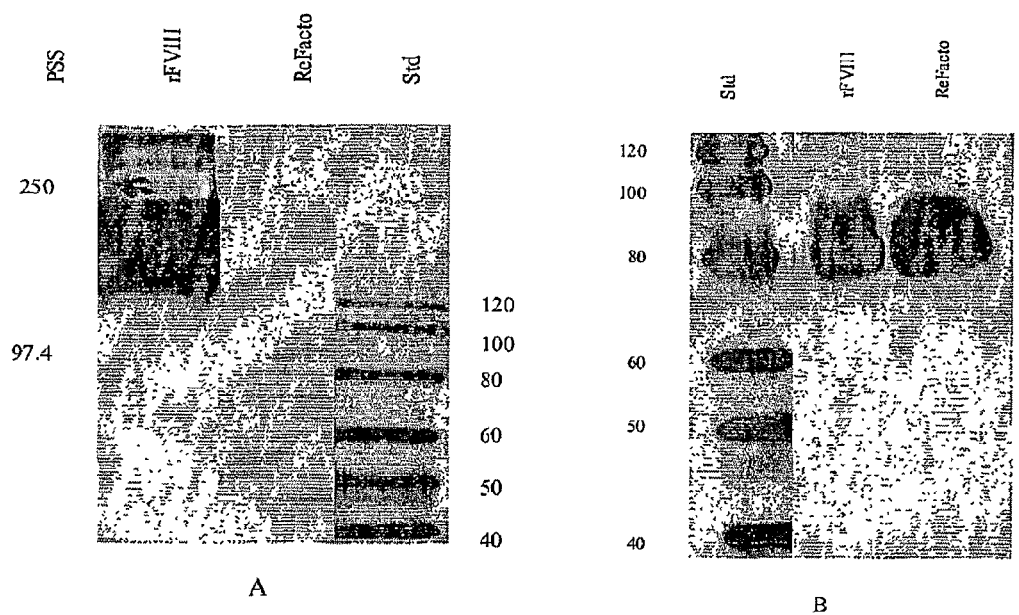
FIG. 2A-B is two photographs of immunoblots showing reactivity of mAbs anti-FVIII-1 (2A) and anti-FVIII-68 (2B) against preparations containing FVIII protein, according to an embodiment of the invention.

The epitope specificity of anti-FVIII-1 mAb was confirmed by immunoblotting (FIG. 2). More specifically, FIG. 2 shows immunoblots of reactivity using anti-FVIII-1 (2A) and anti-FVIII-68 (B) as probes. Proteins (0.2 µg in 50 µl) were subjected to electrophoresis (7.5% SDS-PAGE, under non-reducing conditions) and immunoblotting. Binding of FVIII-specific mAbs was visualized with sheep anti-mouse Ig and ELC western blotting detection reagents. As seen in FIG. 2A, mAb 1 does not bind to ReFacto whereas it reacts with full-length rFVIII. In contrast, ReFacto could be detected using a different mAb, i.e., anti-FVIII-68 (FIG. 2B). Monoclonal Ab 68 bound to an approximately 80 kDa fragment consistent with binding specificity for FVIII light chain. This mAb bound both the full-length FVIII and ReFacto (FIG. 2B). Though anti-FVIII-68 bound ReFacto, it did not exhibit significant binding to activated FVIII and it did not bind to FVIII in complex with vWF (Table II). This indicates that the binding region of mAb 68 is sterically hindered when FVIII is in complex with vWF.

Anti-FVIII-23 mAb. The epitope recognized by the clone 23 antibody was mapped to FVIII heavy (H/L)-chain. Nevertheless, its epitope was not found to overlap with that of clone 24, as evidenced by the fact that binding of FVIII to mAb 24 could be probed with anti-FVIII-23, as shown in FIG. 1B.

Figure 3A:
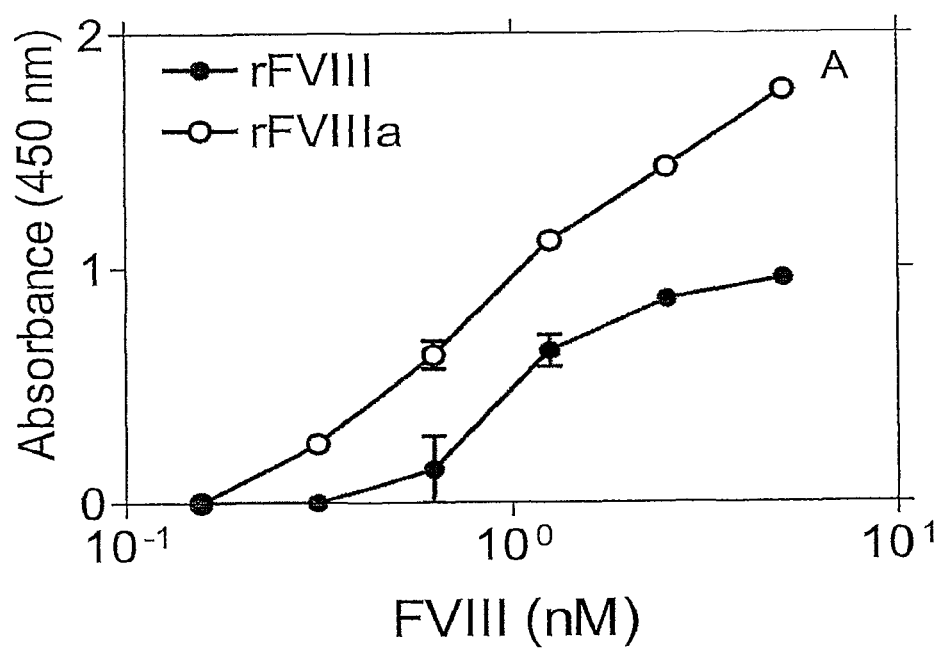
FIG. 3A-B is two graphs showing the binding specificity of certain anti-FVIII mAbs for recombinant FVIII protein (rFVIII) or activated FVIII (rFVIIIa) in a double sandwich immunoassay according to an embodiment of the invention. Binding was detected with anti-FVIII-23 mAb (3A) or anti-FVIII-68 mAb (3B).
Figure 3B:
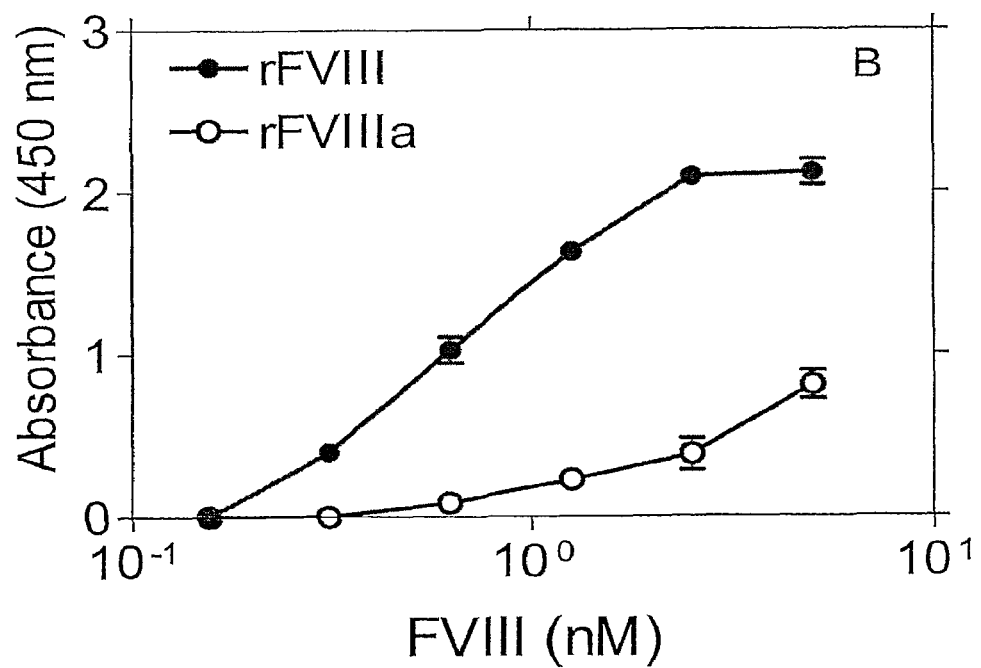

Interestingly, mAb 23 exhibited preferential binding to activated-FVIII, as illustrated in FIG. 3. FIG. 3 shows the binding specificity of mAb-23 compared with mAb-68. More specifically, a sandwich immunoassay was performed in which FVIII or FVIIIa was immobilized on anti-FVIII-24 (Fab)'2 fragment. FVIII binding was probed using anti-FVIII-23 mAb (FIG. 3A) or anti-FVIII-68 mAb (FIG. 3B) and HRP-anti-mouse FC. FIG. 3A shows that once captured by anti-FVIII-24 (Fab)'2, mAb 23 binds to FVIIIa significantly better than to FVIII. By contrast, mAb 68 binds preferentially to rFVIII (FIG. 3B).

Figure 4:
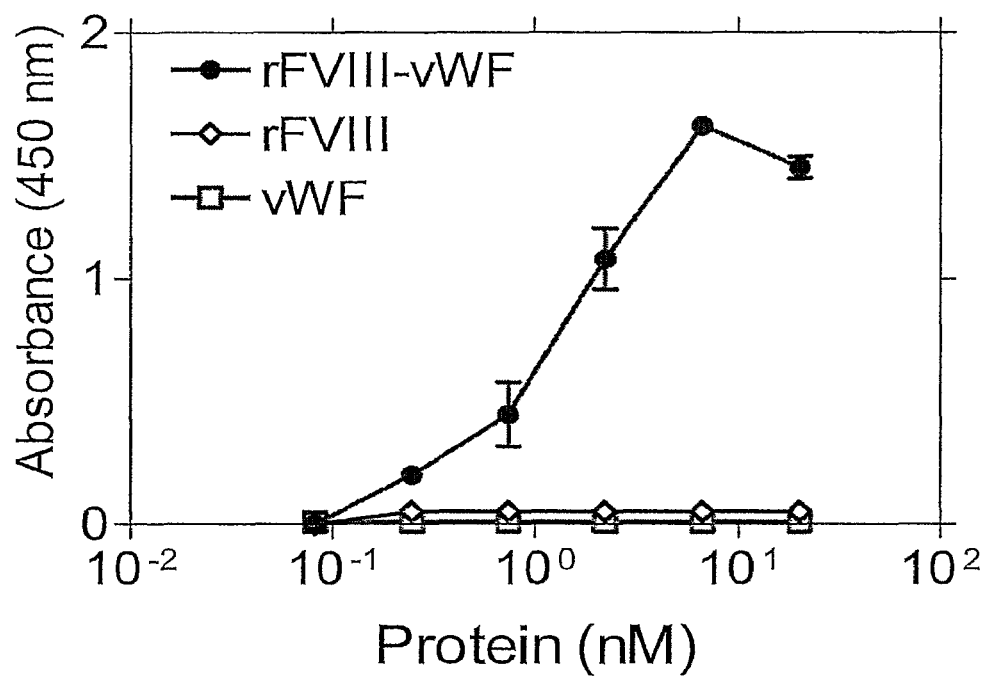
FIG. 4 is a graph illustrating the binding specificity of anti-FVIII-24 mAb according to an embodiment of the invention. FVIII-vWF complex was immobilized on anti-FVIII-24 mAb (Fab)'$_2$ fragment. Binding was probed with anti-vWF mAb and HRP-anti-mouse FC.

Anti-FVIII-24 mAb. The binding specificity of clone 24 was mapped to the FVIII H/L chain. The epitope for this mAb is exposed when FVIII is in complex with vWF. This was demonstrated using an immunoassay in which binding of complexed FVIII-vWF to immobilized anti-FVIII-24 (Fab)'2 fragment was probed using vWF-specific mAb and HRP-anti-FC (FIG. 4). More particularly, FIG. 4 shows the results of an immunoassay in which FVIII-vWF complex was immobilized on anti-FVIII-24 mAb (Fab)'2 fragment and binding was probed with anti-vWF mAb and HRP-anti-mouse FC.

Figure 5A:
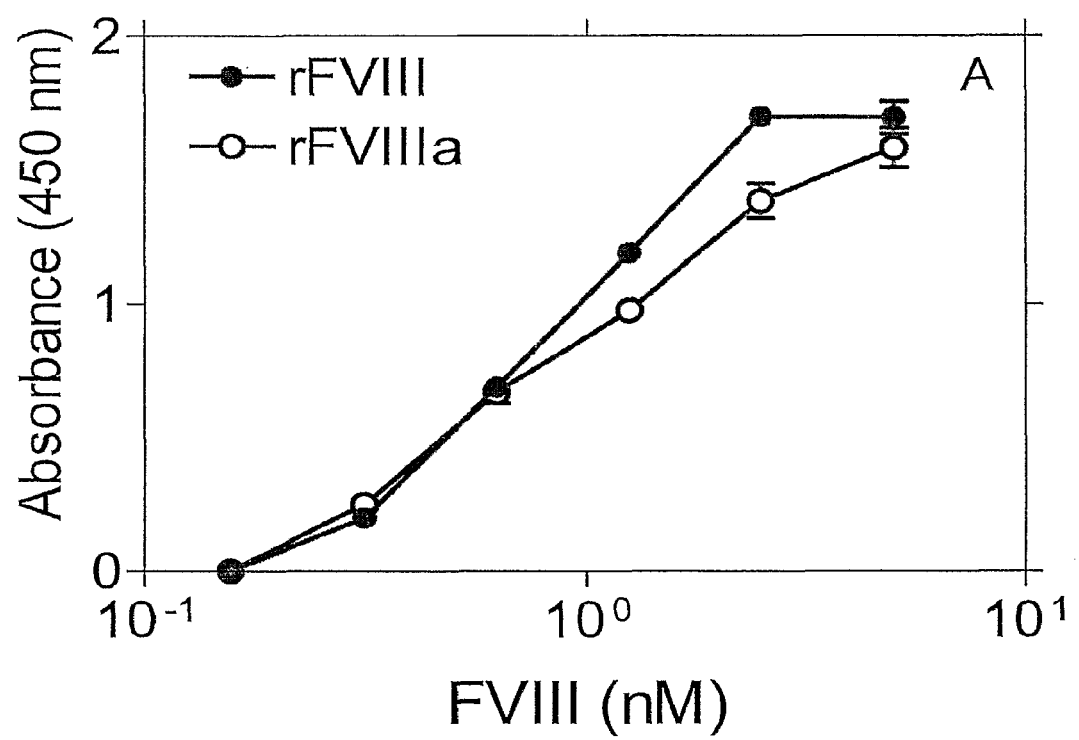
FIG. 5A-B is two graphs illustrating the binding specificity of anti-FVIII-25 mAb in the presence of $CaCl_2$ containing HBS (5A) or PBS (5B), according to an embodiment of the invention. The detecting mAb is anti-FVIII-68.
Figure 5B:
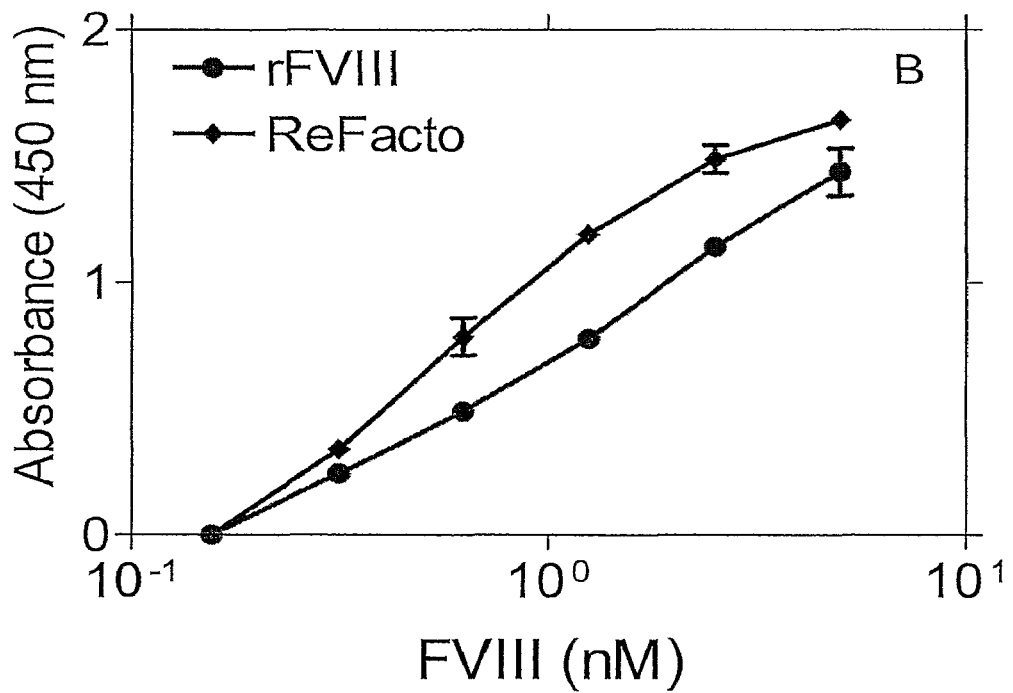

Anti-FVIII-20, -21, and -25 mAbs. As shown in Table II, binding of each of these mAbs to FVIII and FVIIIa protein was indistinguishable. Representative graphs for mAb-25 are shown in FIGS. 5A and 5B. More specifically, FIG. 5 shows results of immunoassays in which rFVIII and rFVIIIa or ReFacto were immobilized on full-length anti-FVIII-25 mAb. Binding was probed with L-chain specific anti-FVIII-68 and HRP-protein A (only mAb 68 binds to protein A, see Table I). Binding in the presence of CaCl$_2$ containing HBS is shown in FIG. 5A. FIG. 5B illustrates binding in the presence of PBS.

The binding region of mAbs-20, 21 and 25 is sterically and spatially different from that of mAbs 23 and 24. Unlike mAb 23, these mAbs do not distinguish between FVIII and FVIIIa. Unlike mAb 24, the epitope for these mAbs is sterically hindered when FVIII is in complex with vWF.

The binding region of these mAbs was tentatively mapped to FVIII H/L-chain due to the fact that both FVIII and ReFacto can be captured by these mAbs and detected using a light chain-specific mAb (i.e., anti-FVIII-68). A representative experiment is shown in FIG. 5B in which binding of immobilized rFVIII or ReFacto on anti-FVIII-25 can be detected using mAb 68 and HRP-protein A.

Example 5

Use of Anti-FVIII mAbs in Immunoassays to Determine Concentration of FVIII in Commercial Products Comprising FVIII Using immunoassays as described above, several approaches were utilized to determine FVIII concentration as follows:

a. Concentration of free FVIII (for example, as found in Recombinate™, ReFacto™, or Kogenate™) was determined using a double mAb sandwich assay in which FVIII was captured by anti-FVIII-24 (Fab)'$_2$ fragment and its binding was probed using a light-chain specific mAb (as shown, for example, in FIG. 4B).

b. Concentration of FVIII in products that contained vWF (for example, Hemofile M™ and Immunate™) was determined by first using thrombin to activate FVIII (i.e., to release FVIII from vWF) and then using a double mAb sandwich immunoassay in which binding of immobilized FVIII on anti-FVIII-24 (Fab)'$_2$ was probed using mAb 23 which binds preferentially to the activated form of FVIII (as illustrated above, for example, in FIG. 3A).

Figure 6:
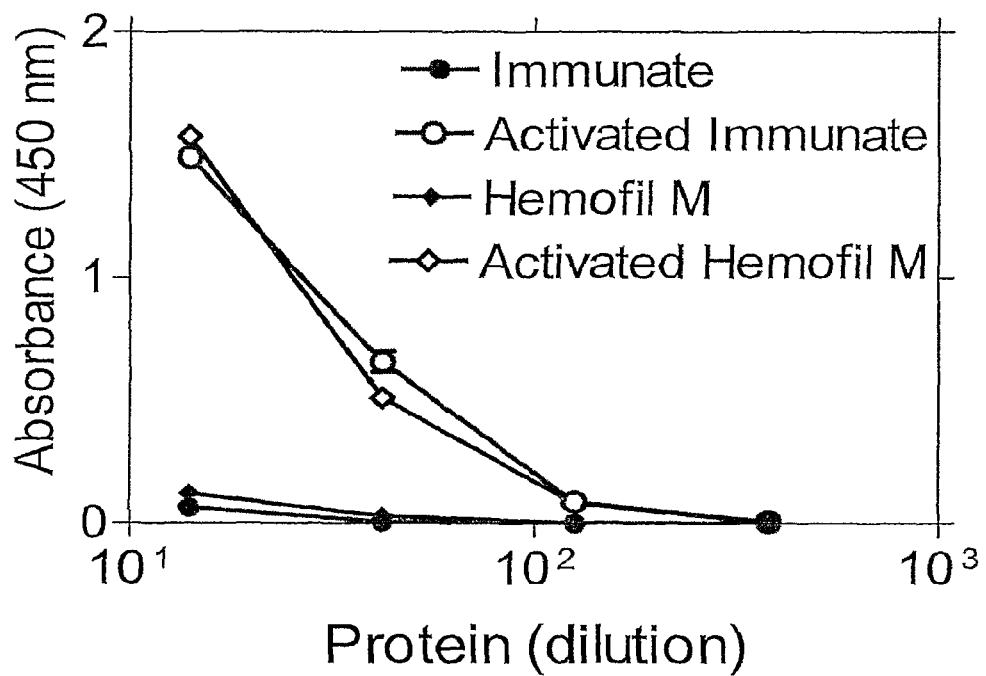
FIG. 6 is a graph showing results of a typical titration curve in which the concentration of FVIII in commercial products containing FVIII-vWF complex was determined by double mAb sandwich immunoassay, according to an embodiment of the invention.

Immunoassay data for commercial products containing FVIII are summarized in Table III infra. A representative titration curve for one batch each of Hemofil M™ and Immunate™ is shown in FIG. 6. More specifically, FIG. 6 shows results of immunoassays used to determine the concentration of FVIII in products which contain FVIII complexed with vWF. In the example shown, Immunate™ or Hemofile M™ were treated with thrombin as described in Materials and Methods. FVIII proteins were immobilized on anti-FVIII-24 (Fab)'$_2$ fragment and binding was detected using anti-FVIII-23 mAb and HRP-anti-mouse FC as probes.

Titration curves similar to that shown in FIG. 6 were generated for each batch of FVIII concentrate shown in Table III. The concentration of FVIII was determined using a standard curve generated for rFVIII, similar to that shown in FIG. 3.

TABLE III

Determination of Specific Activity of FVIII Commercial Products[a]

| Product | ID | Units/ml | Concentration (nM) | Specific activity (units/μg)[b] |
|---|---|---|---|---|
| Recombinate ™ | RAC | 200 | 120 | 5.8 |
| | RAB | 200 | 126 | 5.6 |
| | RAA | 200 | 132 | 5.3 |
| ReFacto ™ | RF9 | 200 | 39 | 30.1 |
| | RF1 | 200 | 50 | 23.5 |
| | RF4 | 200 | 50 | 23.5 |
| Kogenate ™ | K9P | 100 | 77 | 4.5 |
| | K7G | 200 | 176 | 4.0 |
| | KF1 | 400 | 218 | 6.4 |
| Hemofile M ™ | H54EA | 200 | 135 | 5.2 |
| | H44EA | 200 | 131 | 5.3 |
| | H04EB | 200 | 123 | 5.7 |
| Immunate ™ | IM1I | 100 | 129 | 2.7 |
| | IM2K | 100 | 143 | 2.4 |
| | IM1K | 100 | 160 | 2.2 |

[a]FVIII specific activity was determined using two different double mAb sandwich assay. For Recombinate ™, ReFacto ™ and Kogenate ™, FVIII bound to mAb 24 was probed with an L-chain specific mAb as described. For Hemofile M ™ and Immunate ™, activated proteins bound to mAb 24 were probed with anti-FVIII-23 mAb as described. In general, each vial of FVIII was reconstituted with sterile water based on activity (units) reported on the vial to contain 100-400 units/ml.
[b]For determination of specific activity a molecular weight of 170,000 was assumed for ReFacto ™ and 285,000 for all other products specified above.

In summary, as shown in Table II, the epitope specificity of various mAbs of the invention generally divided into three groups; i.e., H/L-chain specific (for example, mAbs 20, 23, 24 and 25), L-chain specific (for example, mAb 68) and B-domain specific (for example, mAb 1). The H/L-chain specific mAbs differed in their fine specificity as evidenced by their different reaction with activated FVIII and FVIII-vWF complex (Table II).

As shown above, these differences among the antibodies enabled double sandwich mAb assays to be designed in which FVIII can be quantitated even when complexed with vWF (see, for example, FIG. 3A and FIG. 6). Availability of a large panel of FVIII mAbs is also useful for quantifying FVIII fragments such as the B-domain-deleted FVIII, ReFacto™. By using a combination of heavy/light- and light-chain specific mAbs, the concentration of ReFacto was determined to be in the range of 50-77 nM in three different preparations (See, for example, Table III).

For FVIII products that contained vWF, a different assay was designed. Two H-chain-specific mAbs were used, one of which preferentially binds to activated FVIII. Thus when FVIII products are activated with thrombin to dissociate FVIII from vWF, activated FVIII can be probed with mAb 23 (FIG. 3A). Using the above-described assay, the concentration of FVIII in Hemofile M™ and Immunonate™ can be assessed (Table III).

From the foregoing, it can be appreciated that the antibodies and immunoassays of the invention can enable precise determination of the concentration of FVIII in various forms of FVIII products, and calculation of the specific activity of these products.

Example 6

Figure 7A:
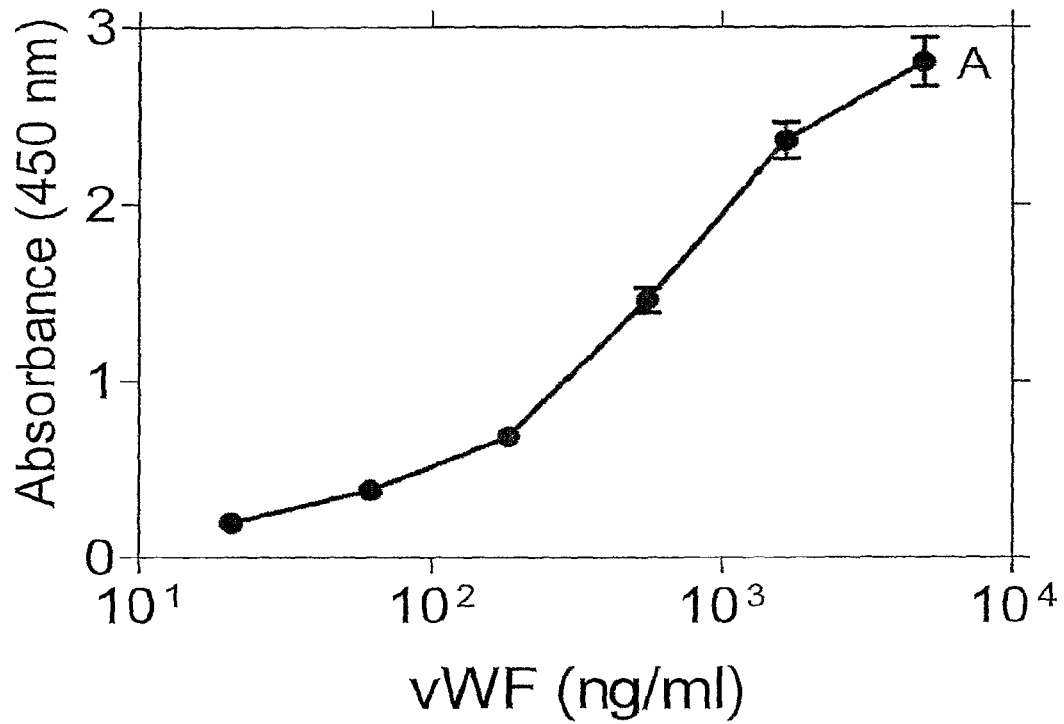
FIG. 7A-B is two graphs illustrating a double sandwich immunoassay for quantifying von Willebrand factor (vWF) in products containing FVIII, according to an embodiment of the invention.

Use of Immunoassays to Determine Concentration of Von Willebrand Factor (vWF) in Commercial Products Comprising FVIII The concentration of vWF in Hemofile M™ and Immunate™ was determined using a double sandwich assay combining mAb and polyclonal antibody in which vWF was immobilized on anti-vWF mAb. Binding to the mAb was probed using goat anti-vWF polyclonal Ab and HRP-antigoat Ig. Representative data is shown in FIG. 7. FIG. 7A shows a standard curve for purified vWF. More particularly, the standard curve was generated by immobilizing the indicated concentrations of purified vWF on an anti-vWF mAb. Detection of binding was achieved using a polyclonal goat anti-vWF antibody and HRP-anti-goat Ig.

For determination of the concentration of vWF in commercial products containing FVIII, the FVIII concentrates were diluted 14-fold, with 3-fold dilutions thereafter. Binding was probed as described for the vWF standard curve (FIG. 7A). Representative results are shown in FIG. 7B.

Figure 7B:
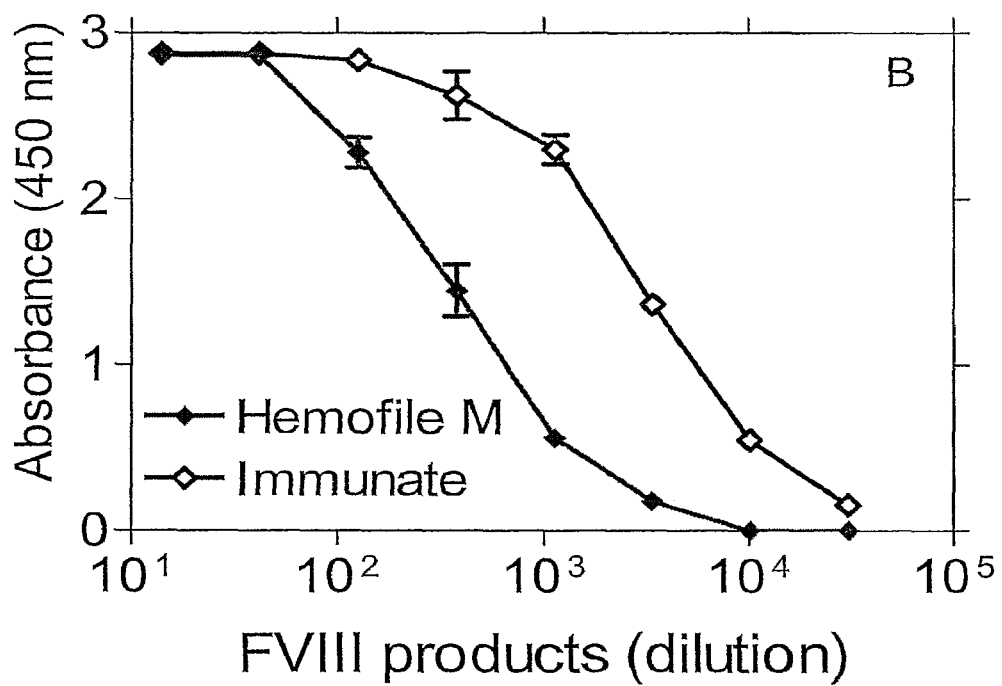

Referring to FIG. 7B, the concentration of vWF in Hemofile M™ was found to be 207 µg/ml, whereas the concentration of vWF in Immunate™ was 1665 µg/ml. These data indicates that Immunate™ contains approximately 8-fold more vWF than Hemofile M™. vWF Results of repeat experiments with three separate batches of these products showed that the concentration of vWF in Hemofile M™ was in the range of 153-207 µg/ml, and in Immunate™ was in the range of 1665-1713 µg/ml.

Example 7

Combined Immunoassay and Biological Assay Method for Improved Quality Assessment in FVIII Products Precise determination of FVIII quality in commercial concentrates is critical in the management of hemophilia A. Currently, two assays are used for the evaluation of FVIII activity in concentrates, i.e., clotting assays (for example, the activated partial thromboplastin time (APTT) assay and chromogenic assays (Kleinveld et al., 1999; Mikaelsson et al., 2001; Barrowcliffe et al., 2002; Mikaelsson and Oswaldsson, 2002). There are significant discrepancies among these activity assays (Lundblad et al., 2000). The discrepant findings in activity assays could arise from the differences in the standards, source of reagents, variations in the protocols or the nature of the FVIII concentrate (Lusher et al., 1998; Mikaelsson et al., 1998; Mikaelsson et al., 2001; Barrowcliffe et al., 2002; Mikaelsson and Oswaldsson, 2002).

Importantly, activity assays describe a complex array of kinetic reactions that could be differ among various plasmas from healthy individuals made immunodeficient for FVIII. For example, it has been shown that the response in "healthy" individuals is significantly influenced by the overall composite of quantitative levels of other hemostatic factors that typically fall within the range of 50-150% (Butenas et al., 1999). Thus when the APTT assay is used to quantify FVIII products, different clotting values could be produced.

One approach to overcome assay discrepancies is the parallel use of more sensitive and reproducible FVIII activity assays combined with the use of analytical approaches for standardization of FVIII concentration in these assays. As discussed, the monoclonal Abs and immunoassays described herein can be used to precisely determine FVIII concentration in a variety of commercial products. Thus improved assays of FVIII product quality are described herein that utilize a combination of sensitive and reproducible immunoassays to precisely determine the physical mass with activity assays by which the FVIII activity in purified concentrates can be assessed. It is important to emphasize that FVIII activity alone, or FVIII concentration alone (for example, as measured by an immunoassay) are unlikely to be sufficient for accurate determination of FVIII quality in concentrates. For example, activity assays do not reflect the presence of degraded or aggregated FVIII that have lost function. Immunoassay alone is not sufficient because the biological activity of the measured FVIII protein is not determined by this method.

We have determined that the anti-FVIII monoclonal antibodies described herein are not inhibitory in a conventional APTT assay at concentrations as high as 56 nM, as evidenced by the finding that the change in clotting time was minimal in the presence of the anti-FVIII mAbs of the invention, as compared to control mAbs. Therefore the mAbs can be used to in assays to determine the specific activity of FVIII products (activity correlated with measured concentration of FVIII).

Example 8

Highly Sensitive Fluorescence-Based Immunoassay Suitable for Detection of FVIII in Human Plasma This example describes a highly sensitive fluorescence-based immunoassay system that integrates FVIII ELISA with multi-analyte platform technology. The method is useful, for example, to determine FVIII concentration in fluids such as human plasma, and is sufficiently sensitive to detect FVIII in the serum of patients with blood clotting disorders such as hemophilia.

1. Design of Fluorescence-Based Immunoassay (FLI)

The design of an exemplary fluorescence-based FVIII assay of the invention is shown schematically in FIG. 8. Referring to FIG. 8, a first anti-FVIII mAb is coupled to microsphere beads having a first selected spectral address, for example, fluorescent bead classification #038). Following binding of rFVIII or plasma FVIII to the mAb-bound microspheres, bound FVIII protein is detected using a second anti-FVIII mAb comprising a detectable label, for example biotin. Detection of the biotinylated antibody is achieved for example using fluorescent streptavidin, such as R-Phycoerythrin(PE)-streptavidin). In the example shown, exemplary first and second anti-FVIII mAbs are shown having the respective characteristics: $IgG_2b$, κ, L-chain specific; and $IgG_1$, κ, H-chain specific. Those of skill in the art will recognize however that the invention is not so limited and that any suitable combination of antibodies can be used.

Referring to the right-hand side of FIG. 8, specificity of the reaction is determined by use of control beads that are included in each assay. Control beads comprise an isotype-matched mAb (in this example, $IgG_2b$, κ) with specificity irrelevant to FVIII, coupled to microspheres having a different spectral address than the FVIII-binding beads (for example, fluorescent bead classification #026).

2. Coupling of Anti-FVIII Capture Antibody to Fluorescent Beads

Systems and general protocols for attaching antibodies to fluorescent beads (also termed "microspheres") are available from commercial sources such as Luminex Austin, Tex.). To achieve the desired coupling and distribution of the capture antibody on the beads, we found that in order to achieve very high levels of FVIII detection sensitivity, significant experimentation and modification of a typical manufacturer's protocol was required when using a particular combination of a capture antibody and a bead with selected spectral properties.

The following is a general discussion of the various modifications that are necessary to achieve the highest levels of sensitivity, as illustrated in Examples below. Additionally, we provide as an illustration a detailed protocol for the preparation of beads used in a preferred embodiment of the invention, described infra.

Vortexing and sonicating. We have found that the use of vortexes and sonicators, for example as recommended by Luminex, are not appropriate in coupling antibodies to microspheres, due to the fact that significant numbers of beads break down and fall into pieces using these methods. This is determined experimentally by comparing the yields before and after the coupling procedures. Specifically, we obtain much greater yields of coupled beads at the end of the procedure if we did not use either a vortex or a sonicator. Furthermore, the assay sensitivity and detection also improves if the use of vortexing and sonicating is avoided.

Centrifugation time and speed. We determined that centrifugation parameters recommended by Luminex result in significant loss of beads. For best yields, we increase the centrifugation time to 3 min (2 min recommended by Luminex) and the speed to 11000-12000 rpm (Luminex recommends 10,000 rpm or 8000×g).

Volumes and pH of activation and coupling buffers. Other changes resulting in increased yield and sensitivity include increasing activation and coupling buffer volumes by 20% over a recommended (Luminex) protocol. This modification results in improved bead activation and enhanced mAb binding to the beads. Another important parameter is the pH of the buffer in which the mAbs are coupled to the beads. A pH of 5.0 is recommended by Luminex. However, we found that a low pH such as 5.0 is not suitable for coupling of our anti-FVIII mAbs to beads. We determined that it is preferable to increase the pH of the coupling buffer to above 6.0.

Antibody concentration. One manufacturer's protocol (Luminex) suggests an antibody concentration of 25 µg/ml or higher. In contrast, we have found that best results regarding sensitivity and FVIII detection levels using much lower concentrations of antibody (for example, 5 µg/ml of anti-FVIII-68 mAb).

Simultaneous detection of specific and non-specific binding in the same sample. A very important aspect of the invention is a built-in control for non-specific binding that has not been described in any commercial protocol, to our knowledge. This is a particularly important step when biological samples such as plasma are used. Because plasma comprises many proteins besides FVIII and heterophilic antibodies that could bind non-specifically to beads or probes and increase the signal, it is extremely important to be able to distinguish between specific and non-specific signals in the assay, for example to screen out spurious, non-specific binding in a patients' plasma sample. This method ensures that the observed signal is specific for FVIII.

As discussed above, an isotype-matched capture mAb with specificity irrelevant to FVIII is coupled to beads that have a different spectral address from that of the anti-FVIII-mAb-coupled beads. For example, we couple anti-FVIII-68 mAb to beads 038, and control mAb to beads 026. In the practice of the assay, identical numbers of the anti-FVIII and control mAb-coupled beads (e.g., 5000 particles of each) are added to each well. After capturing plasma FVIII, secondary (probe) antibody labeled with a detectable label (e.g., biotinylated anti-FVIII-24 and fluorophore-streptavidine) are added. Fluorescence is then measured by a detector (such as a Luminex machine), which determines the signals from 038 (specific) and 026 (non-specific) beads.

A particularly preferred protocol for coupling of beads is provided below:

Buffers and Reagents:
Activation buffer: 0.1M $NaH_2PO_4$ pH 6.2, (Sodium Phosphate monobasic anhydrous) (Sigma S-3139), use 5N NaOH to adjust pH, filter sterilize and store at 4° C.
Coupling buffer: 0.1M MES pH 6.0, (2[N-Morpholino] ethanesulfonic acid) (Sigma M-2933), use 5N NaOH to adjust pH, filter sterilize and store at 4° C.
Wash buffer: 1×PBS/0.05% Tween-20 pH 7.4, (1× Phosphate Buffered saline/0.05% Tween-20) filter sterilize and store at room temperature (Tween-20:_Sigma P-9416).
Blocking/Storage buffer: 1×PBS/1% BSA/0.02% Tween-20/0.05% Azide pH 7.4, (1× Phosphate Buffered Saline/1% Bovine Serum Albumin/0.02% Tween/0.05% Sodium Azide) filter sterilize and store at 4° C. BSA: Sigma A-7888; Tween-20: Sigma P-9416; Sodium Azide: Sigma S-8032
Sulfo-NHS: N-hydroxysulfosuccinimide, store at 4° C. in dessicated container. (Pierce 24510)
EDC: 1-ethyl-3-[3-dimethylaminopropyl]carbodiimide hydrochloride, store at −20° C. in dessicated container. (Sigma E-1769)
Microfuge tubes: 1.5 ml USA Scientific 1415-2500

Coupling Protocol:
Microspheres should be protected from prolonged exposure to light throughout this procedure. All reagents including buffers and microspheres must be warmed up to room temperature before coupling. No vortexing or sonicating procedures should be used in any of the steps below.

1. Mix stock beads at room temperature by rotating for minimum of 30 minutes before starting.

2. Resuspend the microspheres by pipetting for approximately 20 seconds. Pipette the mixture up and down a few times using a sterile disposable pipette.

3. Transfer $5.0 \times 10^6$ (stock $1.25 \times 10^7$ beads in 1 ml) or 400 µl to a macrophage tube.

4. If volume to be coupled is less than 400 µl adjust the volumes of buffers, activation reagents and protein to be coupled. Do not couple more than 400 µl in one microfuge tube.

5. Pellet the microspheres by microcentrifugation at 11,000 rpm for 3 minutes.

6. Remove the supernatant and resuspend the pelleted microspheres in 200 µl of activation buffer (0.1M NaH2PO4 pH 6.2)—mix well by pipetting using 50-200 µl pipette.

7. Repeat step 5, step 6 and again step 5.

8. Remove the supernatant and resuspend the pelleted microspheres in 2000 of activation buffer (0.1M NaH2PO4 pH 6.2)—mix well by pipetting.

9. Weigh and prepare 50 mg/ml Sulfo-NHS in activation buffer and 50 mg/ml EDC in activation buffer.

10. Add 25 µl of 50 mg/ml Sulfo-NHS (diluted in activation buffer) to the microspheres and mix gently by pipetting. For best results make the stock just before use.

11. Add 25 µl of 50 mg/ml EDC (diluted in activation buffer) to the microspheres and mix gently by pipetting. For best results make the stock just before use.

12. Incubate for 20 minutes at room temperature in dark on a shaker.

13. Pellet the activated microspheres by microcentrifugation at 11,000 rpm for 3 minutes.

14. Remove the supernatant and resuspend the pelleted microspheres in 500 µl of coupling buffer (0.1M MES pH 6.0)—mix well by pipetting.

15. Repeat step 13, step 14 and again step 13 two times— total of 3 washes.

16. Resuspend beads in 200 µl of coupling buffer and mix well. Add 800 µl of coupling buffer and spike anti-FVIII-68 mAb to obtain 5 µg/ml mixture (7.50 of 0.66 mg/ml stock)— mix well by pipetting.

17. Incubate for 2 hours with mixing by rotation at room temperature in dark.

18. Pellet the coupled microspheres by microcentrifugation at 11,000 rpm for 3 minutes.

19. Remove the supernatant and add 6000 of blocking/storage buffer (1×PBS/1% BSA/0.05% Tween/0.02% Azide pH 7.4)—mix well by pipetting.

20. Repeat step 18.

21. Resuspend the pelleted microspheres in 6000 of blocking/storage buffer (1×PBS/1% BSA/0.05% Tween/0.05% Azide pH 7.4)-mix well by pipetting.

22. Rotate the microspheres overnight in dark at 4° C.

23. Next day pellet the coupled microspheres by microcentrifugation at 11,000 rpm for 3 minutes. Remove the supernatant. Add 4000 of fresh blocking/storage buffer, mix well by pipetting and record number of beads/ml on the tube.

Other Procedures:

The following procedures are provided as examples of those suitable for performing various aspects of the FVIII assay fluorescent immunoassay and suitable controls, following coupling of the capture and control antibodies to the microspheres. Those of skill in the art will recognize that many other variations are possible and within the scope of the invention.

i. Bead coupling as per above protocol: anti-FVIII-68 (IgG$_2$b) mAb coupled to bead 038 and anti-FXIII 2-4 (IgG$_2$b) mAb coupled to bead region 026 for specificity control.

ii. Individual microcentrifuge tubes containing the desired beads (stored at 4° C. in dark) must be wrapped, e.g. in aluminum foil to prevent exposure to light and warmed to room temperature rotating on a rotor for a minimum of 30 minutes before use.

iii. Mix beads with pipettor for 30 seconds before use.

iv. Make a dilution of beads to be used in the assay (e.g., 100 beads/µl as recommended by Luminex). The final number of beads in 100 µl reaction mixture (500 µl sample+50 µl beads per well) should be about 5000 beads. Buffer: 1× Phosphate buffered saline 0.1% Bovine Serum Albumin/0.05% Tween20—filter sterilized pH 7.4

Total number of samples (wells) to be tested×the volume of bead solution per well=total volume of bead solution needed.

Ex. 48 wells×50 µl/well=2400 µl total bead volume needed

Rotate to prevent bead aggregation and precipitation until ready to load the samples onto the plate.

Preparation of Intermediates i. 1000 mM β-mercaptoethanol:
 a) To a microfuge tube add 276 µl of 1×PBS/0.1% BSA/0.05% Tween20.
 b) From a stock of 12,543 mM β-mercaptoethanol add 24 µl to 276 µl buffer to make a 1000 mM intermediate—mix well by vortexing.
 c) Keep at room temperature. The intermediate must be made fresh each day needed—discard unused solution.

ii. 100 nM rFVIII or 28.5 µg/ml (MW=285,000):
 a) To a microfuge tube add 286 µl of 1×HBS/1% BSA/0.02% Tween 20 buffer.
 b) Thaw a stock vial of rFVIII (stored in −80° C.), spin down and mix with a pipette. Keep on ice if not used immediately.
 c) From a 620 µg/ml (2.17 µM) rFVIII stock add 14 µl to 286 µl buffer-mix well. Store on ice if not immediately frozen.
 d) This intermediate may be aliquoted and frozen at −80° C. for future use Reduction of rFVIII for Standard:
 i. Thaw FVIII immuno-depleted plasma at 37° C. for 10 minutes in a waterbath.
 ii. In a microfuge tube place 475 µl of 1×PBS/0.1% BSA/0.05% Tween20.
 iii. Spike 5 µl of 1000 mM β-mercaptoethanol intermediate into the 475 µl buffer and mix well by vortexing. Final concentration of β-mercaptoethanol will be 10 mM.
 iv. Add 20 µl of FVIII depleted plasma into the tube containing 10 mM β-mercaptoethanol in buffer and mix well by vortexing. Final dilution of FVIII depleted plasma will be 1:25.
 v. Prepare a 10 nM rFVIII from 100 nM rFVIII intermediate stored at −80° C. To 45 µl of 1×PBS/0.1% BSA/0.05% Tween add 50 of 100 nM rFVIII intermediate—mix well.
 vi. Add 1 µl of 10 nM rFVIII intermediate into the 500 µl solution containing 10 mM β-mercaptoethanol and 1:25 diluted FVIII depleted plasma. Final rFVIII concentration will be 20 pM.
 vii. Mix the sample well by vortexing and rotate for two hours at room temperature.
 viii. After two hour reduction, sample may be titrated and tested or stored at −80° C.
 ix. For control sample of FVIII depleted plasma repeat step i, ii, iii, iv, vi and vii in another microfuge tube omitting the addition of rFVIII in step v.

Reduction of FVIII in Plasma Samples:
 i. Thaw plasma samples at 37° C. for 10 minutes in a waterbath.
 ii. In a microfuge tube place 475 µl of 1×PBS/0.1% BSA/0.05% Tween20 buffer.
 iii. Spike 5 µl of 1000 mM β-mercaptoethanol into the 475 µl buffer—mix well by vortexing. Final concentration of β-mercaptoethanol will be 10 mM.
 iv. Add 20 µl of thawed plasma into the tube containing 10 mM β-mercaptoethanol in buffer. Mix well by vortexing. Final plasma dilution will be 1:25.
 v. Rotate for two hours at room temperature.
 vi. After two hour reduction titrate and test or store at −80° C.

Titration of rFVIII Standard and Control FVIII Depleted Plasma (Reduced Samples):
 i. Place multiple (e.g., 9) microfuge tubes in a rack and to each one add 150 µl of IX PBS/0.1% BSA/0.05% Tween20.
 ii. Take 150 µl of the 20 µM reduced rFVIII from step IV and add to the first of the nine tubes containing buffer. Mix well by vortexing. Titrate the rFVIII in the remaining tubes in the same manner.
 iii. The 20 pM reduced sample and the titrated samples will be diluted a further 2-fold with beads in the well of the assay plate. Therefore the actual concentration of rFVIII in the assay will be 10 pM titrated 2-fold. Make these dilutions immediately before addition to the plate containing MAb-bound beads.

Titration of Plasma Samples:
 i. Full titration curve
 a) Place multiple (e.g., 9) microfuge tubes in a rack.
 b) To each tube add 150 µl of 1×PBS/0.1% BSA/0.05% Tween20.
 c) Take 150 µl of the reduced 1:25 plasma sample described above and add to the first of the nine tubes containing buffer. Mix well by vortexing. Titrate the plasma sample in the remaining tubes in the same manner.

d) The 1:25 diluted reduced sample and the titrated samples will be diluted further 2-fold with beads in the well of the assay plate. Therefore the actual dilution factor of the plasma sample in the assay will be 1:50 titrated 2-fold.

e) Make these dilutions immediately before addition to the plate containing beads.

ii. 1:1000 and 1:2000 dilution of plasma without the full titration curve:

a) Place two microfuge tubes in a rack, b) To the first tube add 285 µl of 1×PBS/0.1% BSA/ 0.05% Tween20.

c) To the second tube add 150 µl of 1×PBS/0.1% BSA/ 0.05% Tween20.

d) From the 1:25 reduced plasma sample take 150 and add to the 285 µl buffer containing tube. Mix well by vortexing. The final concentration will be 1:500.

e) From the 1:500 dilution, take 150 µl and add to the 150 µl buffer containing tube. Mix well by vortexing. The final concentration will be 1:1000.

f) The actual dilution factor of the plasma sample in the assay will be 1:1000 and 1:2000 respectively. The 1:500 and 1:1000 dilution from step (d) and (e) will be diluted further 2-fold with beads in the well of the assay plate.

g) Make these dilutions immediately before addition to the plate containing beads.

Assay Setup and Procedure:

i. Pre-wet a multi-well assay plate with 1×PBS/0.1% BSA/ 0.05% Tween buffer for 10 min. Aspirate the liquid before addition of beads using vacuum manifold and in-house vacuum connection.

ii. Add 50 µl of 100 bead/µl ($10^5$ beads/ml) of the bead dilution to each well.

iii. Add 50 µl of FVIII-containing samples to the wells containing bead solution.

iv. Cover the plate with an adhesive tape and place on a shaker.

v. Cover the plate with aluminum foil and set the shaker at 500 rpm for 3 hours.

vi. Wash the plate 3 times with 1×PBS/0.05% Tween using vacuum manifold and strong in-house vacuum connection.

vii. Prepare a 10 µg/ml dilution of biotinylated anti-FVIII-24 mAb in 1×PBS/1% BSA/0.05% Tween (must be warmed to room temperature); add 100 µl to each well.

viii. Set the plate on a shaker, cover and incubate for 1 hour.

ix. Wash the plate 3 times with 1×PBS/0.05% Tween.

x. Prepare a 5 µg/ml dilution of R-phycoerythrin-streptavidin fluorophore in 1×PBS/1% BSA/0.05% Tween; add 100 µl to each well.

xi. Set the plate for 10 minute incubation.

xii. Wash the plate 3 times with 1×PBS/0.05% Tween.

xiii. Add 100 µl of 1×PBS/0.05% Tween to each well and collect the samples (keep samples in covered boxes to prevent light exposure.)

xiv. Read the samples immediately after collection.

Example 9

Detection of rFVIII in the Picomolar Concentration in Immunodepleted Human Plasma Using Fluorescence-Based Immunoassay 1. Materials and Methods:
Preparation of FVIII-Immunodepleted Plasma Plasma (pooled from 5 donors) was spiked with 35 mM (-mercaptoethanol and incubated for 2 hours at room temperature using end-over-end mixing, as described in Methods above. After dialysis in phosphate-buffered saline (pH 7.2), the plasma was immunodepleted on mAb-coupled Sepharose (anti-FVIII-24, 23 and 25 mAbs, H-chain specific). FVIII depletion of the plasma was confirmed using a fluorescence-based immunoassay as described in Example 9.

Generation of Physiologically Relevant Standard Curve for Quantitation of Plasma FVIII Undiluted FVIII-immunodepleted plasma was spiked with various concentrations of rFVIII as described. A mixture of anti-FVIII-68 mAb beads and isotype matched control mAb beads, prepared as described in Example 9 supra, was incubated with rFVIII-containing plasma in order to simultaneously measure specific and non-specific binding. Binding was probed using biotinylated anti-FVIII-24 mAb and PE-streptavidin.

Figure 9:
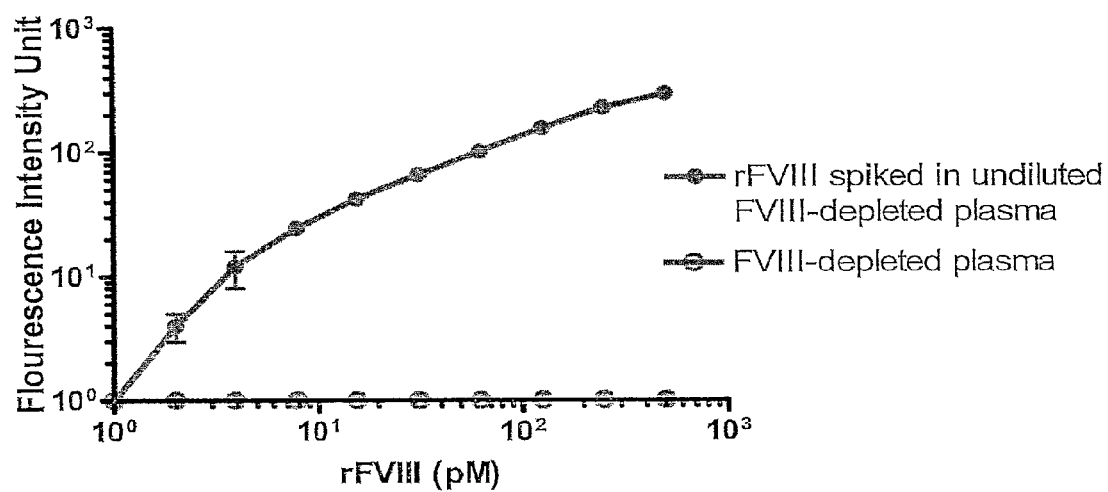
FIG. 9 is a graph showing detection of recombinant FVIII (rFVIII) in FVIII-depleted plasma spiked with using a fluorescence-based immunoassay (FLI) according to an embodiment of the invention. FVIII is not detected in control plasma without addition of rFVIII.

2. Results:
Detection of FVIII in Standard Curve Using FVIII-Immunodepleted Plasma Spiked with rFVIII Confirmation of FVIII depletion was confirmed by the fluorescence-based immunoassay (FLI), as shown in FIG. 9. More specifically, human plasma was immunodepleted as described above, and the depleted plasma was spiked with rFVIII and serially diluted, or tested without addition of rFVIII. Referring to FIG. 9, the results show that FVIII is not detectable by the FLI in immunodepleted plasma lacking FVIII, and is detected by increasing levels of fluorescence in samples spiked with increasing amounts of rFVIII.

Figure 10:
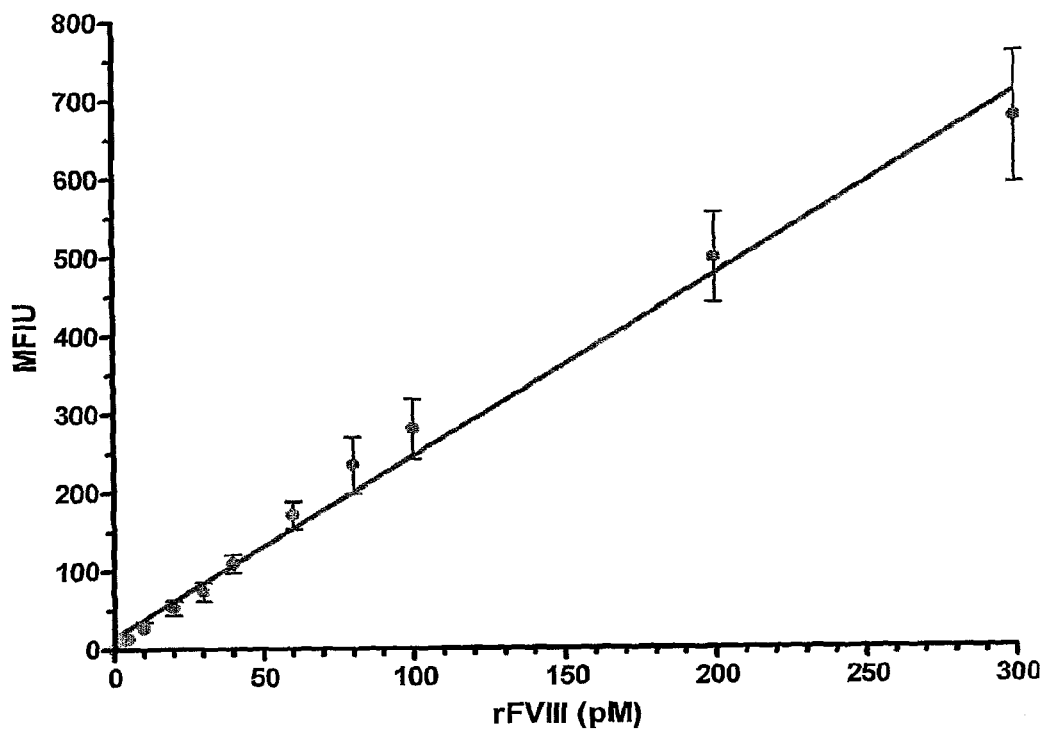
FIG. 10 is a graph showing quantification of FVIII in two different FVIII-immunodepleted plasmas in the picomolar range in a concentration-dependent manner, using a FLI according to an embodiment of the invention.

A typical assay is illustrated in FIG. 10. In this experiment, decreasing concentrations of rFVIII (20-0.04 pM) was spiked in undiluted FVIII immuno-depleted plasma and subjected to FLI. In this assay, anti-FVIII-68 mAb was used for capturing FVIII and biotinylated anti-FVIII-24 mAb and PE-streptavidin was used for detection. FIG. 10 shows that an anti-FVIII mAb such as anti-FVIII-68 mAb coupled to a fluorescent bead can capture rFVIII in a concentration-dependent manner, and that the binding can be detected with a biotinylated-anti-FVIII mAb (in this case anti-FVIII-24 mAB) and PE-streptavidin. The detection level in this assay is in the picomolar range (1 pM) assuming a molecular mass of 285 kDa for rFVIII.

Example 10

Highly Sensitive Quantitation of FVIII in Plasma from Human Subjects Using Fluorescence-Based Immunoassay (FLI)

This Example demonstrates that the FLI of the invention can be used to quantitate FVIII contained in plasma from human subjects following reduction with a reducing agent such as mercaptoethanol.

In these experiments, plasma from healthy human subjects was reduced using 1 or 10 mM β-mercaptoethanol. For generation of concentration curves, the reduced plasma was serially diluted in undiluted FVIII-depleted plasma, prepared as described above for the standard curve using rFVIII, then subjected to FLI. The concentration of FVIII detected in the human plasma was determined by comparison with a standard curve such as that shown in FIG. 10.

Figure 11A:
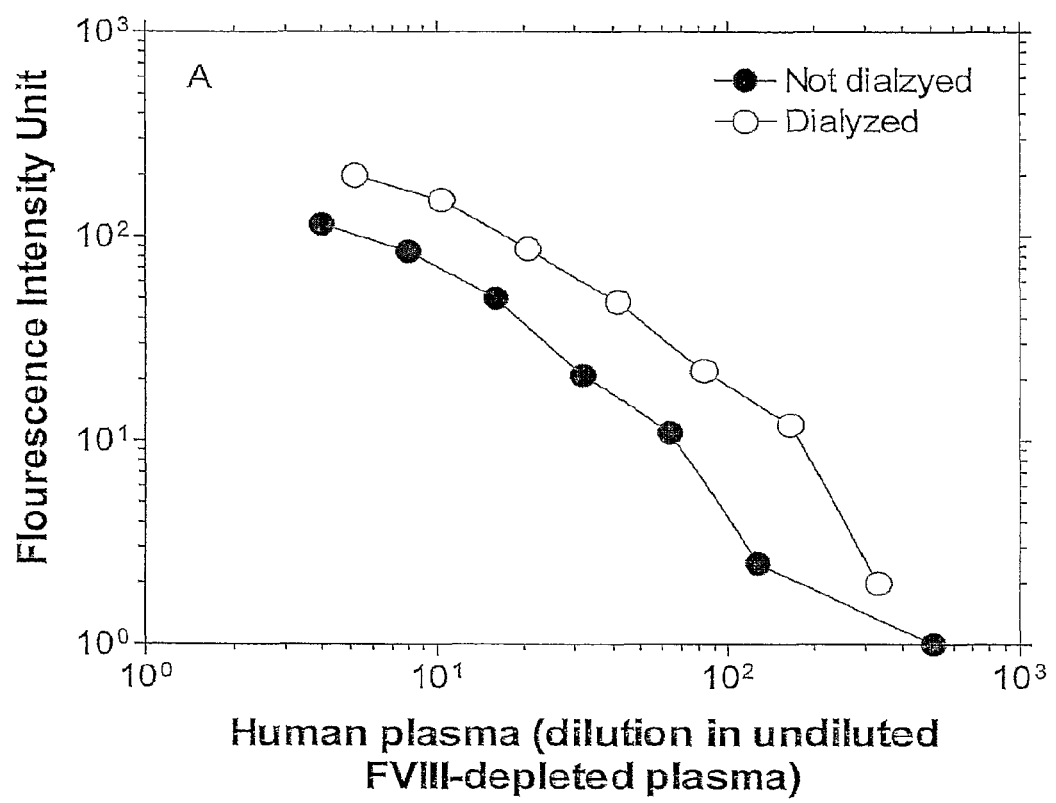
FIG. 11A-B is two graphs showing quantification of FVIII in human plasma treated with a reducing agent (mercaptoethanol) at 1 mM (11A) or 10 mM (11B) concentration, and subjected to FLI according to an embodiment of the invention.
Figure 11B:
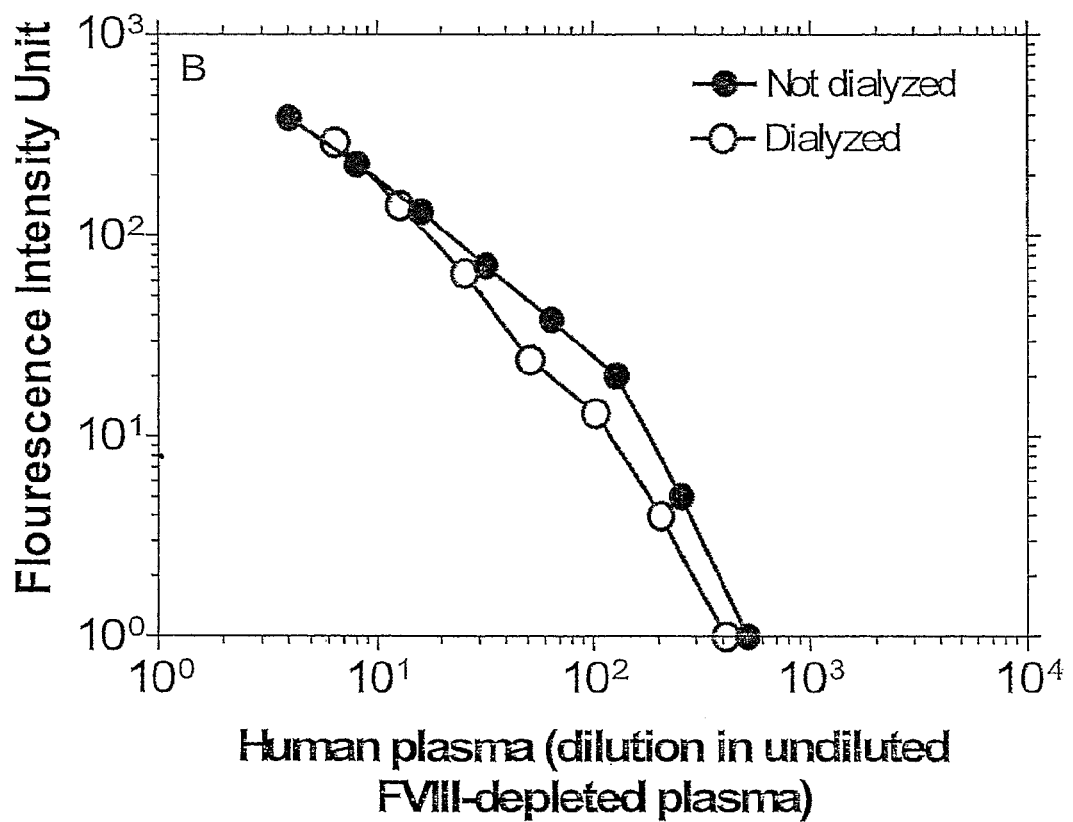

Referring to FIG. 11A, the concentration of FVIII antigen in plasma that was treated with 10 mM β-mercaptoethanol without dialysis was found to be 1.2±0.17 nM using the standard curve shown in FIG. 10. Referring to FIG. 11B, FVIII concentration for plasma treated with 1 mM β-mercaptoethanol was determined to be 0.4 nM. Thus, addition of 10 mM mercaptoethanol improved assay sensitivity and detection levels. Consistent with this, we have also shown that plasma FVIII depletion on a mAb column is much more successful when plasma is reduced with 35 mM β-mercaptoethanol.

It appears that 10 mM β-mercaptoethanol is best for use to determine plasma FVIII concentration. The mechanisms by which β-mercaptoethanol improves assay sensitivity and detection levels are not known. Without intending to be bound by any particular theory, one explanation is that use of this reducing agent results in irreversible dissociation of FVIII from vWF (Lollar, Fay and Fass, Methods in Enzymology, 1993). Thus the FVIII epitopes recognized by the FVIII mAbs may become more accessible for binding to the antibodies.

Figure 12:
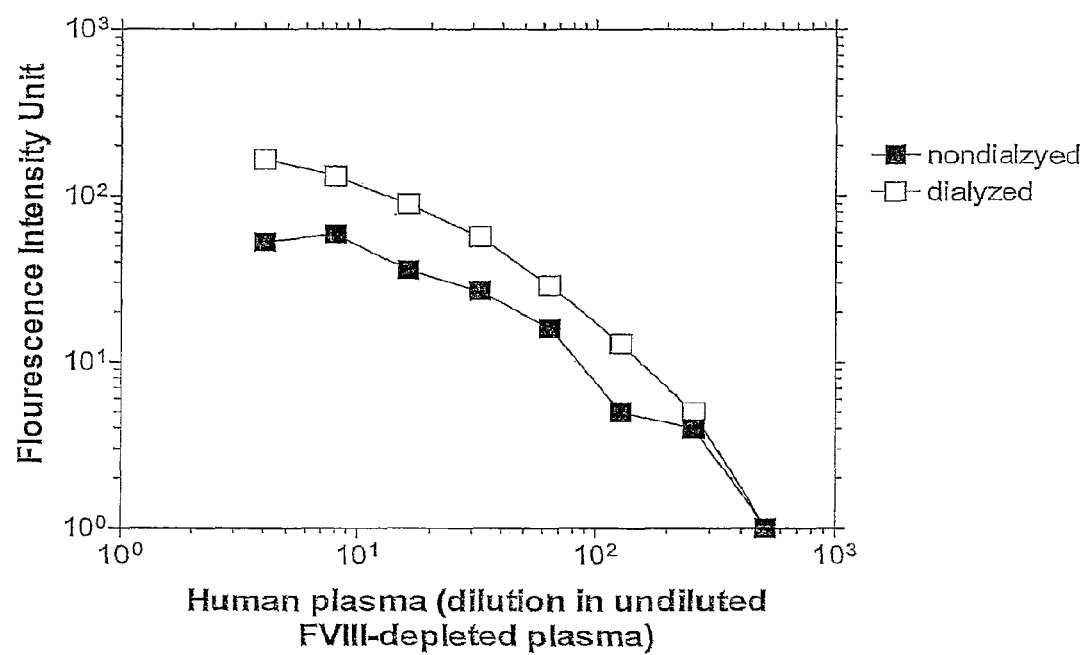
FIG. 12 is a graph showing the effect of dialysis of human plasma on the sensitivity of detection of FVIII in the plasma, using a FLI according to an embodiment of the invention.

We have further determined that there is a significant difference between antibody binding to FVIII both in mercaptoethanol-treated plasma (FIGS. 11A, 11B) and in untreated plasma (FIG. 12) depending upon whether the plasma is dialyzed before immunoassay. The pattern of antibody binding of untreated normal plasma is shown in FIG. 12 and is compared to dialyzed normal plasma. Without intending to be bound by theory, one explanation is that improved performance of the assay results not from the dialysis itself, but from buffering of the plasma with phosphates. Another explanation is that dialysis removes some inhibitors.

Figure 13:
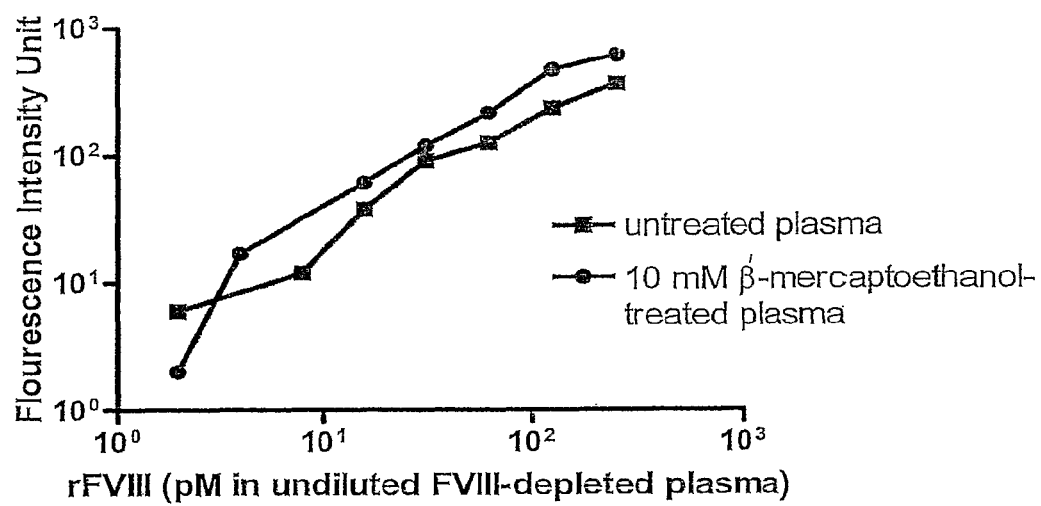
FIG. 13 is a graph showing that treatment of human plasma with a reducing agent improves the binding of anti-FVIII mAbs in a FLI of FVIII according to an embodiment of the invention.

Tests were also conducted to determine whether (-mercaptoethanol treatment can interfere with mAb binding. For these assays, 10 mM β-mercaptoethanol was added to undiluted FVIII-depleted plasma containing rFVIII, and incubated for 2 hours at room temperature. The control was untreated FVIII-depleted plasma spiked with rFVIII. As seen in FIG. 13, the results showed that the addition of β-mercaptoethanol does not interfere with the binding of anti-FVIII mAb beads to rFVIII. Thus the binding of FVIII antibodies to FVIII is not compromised by the presence of this reducing agent in the immunoassay. From the foregoing, it appears that assay sensitivity and detectability can be improved by addition of a reducing agent, dialysis of the sample, or both.

Figure 14:
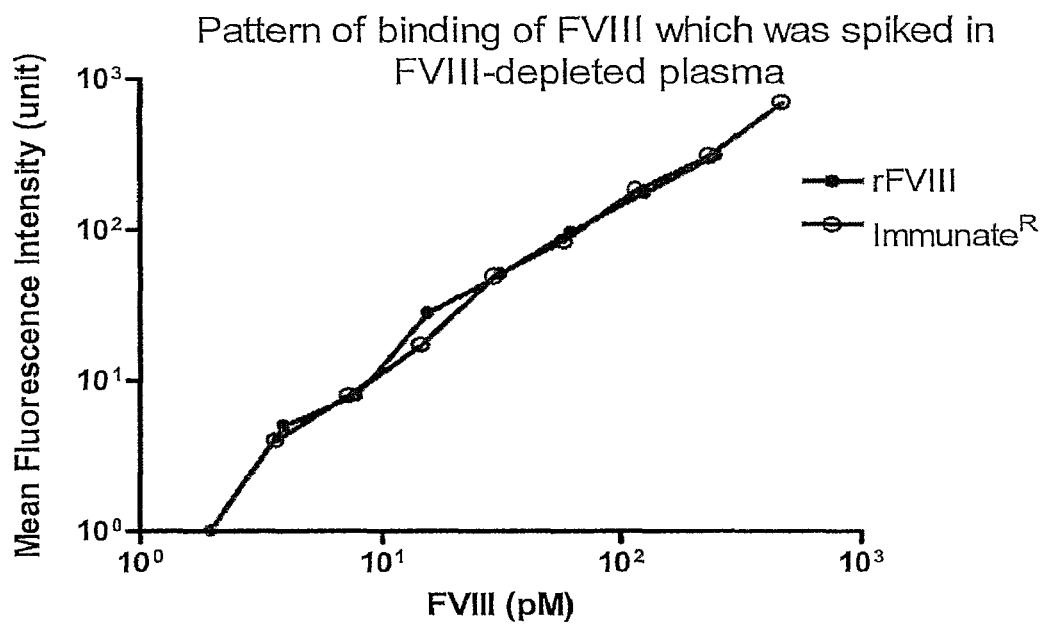
FIG. 14 is a graph showing the detection of FVIII in FVIII-depleted plasma spiked with recombinant FVIII (rFVIII) or with a commercial FVIII product enriched in vWF (Immunate) using a FLI according to an embodiment of the invention.

Using the highly specific and sensitive double monoclonal antibody (mAb) fluorescence-based immunoassay (FLI) integrated into Luminex Multi-Analyte Platform technology as described herein, free- and von Willebrand factor (vWF)-bound plasma FVIII can be recognized equally well. This is shown for example in FIG. 14, as determined by spiking rFVIII or Immunate™ (plasma-derived FVIII containing excess molar concentration of vWF) into FVIII-immunodepleted plasma using methods described above.

Figure 15:
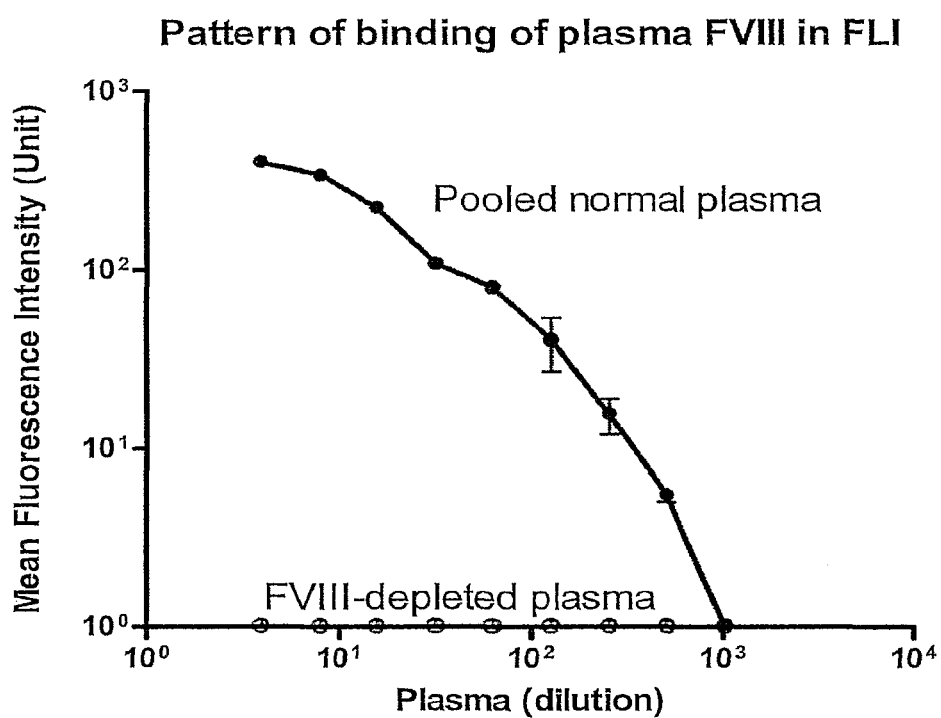
FIG. 15 is a graph showing detection sensitivity of the FVIII FLI. Plasma of healthy individuals can be diluted several thousand fold and picomolar concentrations of FVIII can be quantified in plasma of human subjects by a FLI according to an embodiment of the invention.

Importantly, the fluorescence-based assay of FVIII as described herein can detect FVIII at concentrations significantly lower than 1% mean physiologic concentration. This calculation is based on previous literature reporting that FVIII concentration in normal subjects is about 700 pM. We have determined that concentrations as low as 1-2 pM can be reliably detected using this assay. FIG. 15 shows the results of several independent experiments in which the concentration of FVIII was measured in pooled plasma from healthy individuals using the FLI of the invention, and was found to be detectable in the range of 1.7-2.5 nM.

Figure 16:
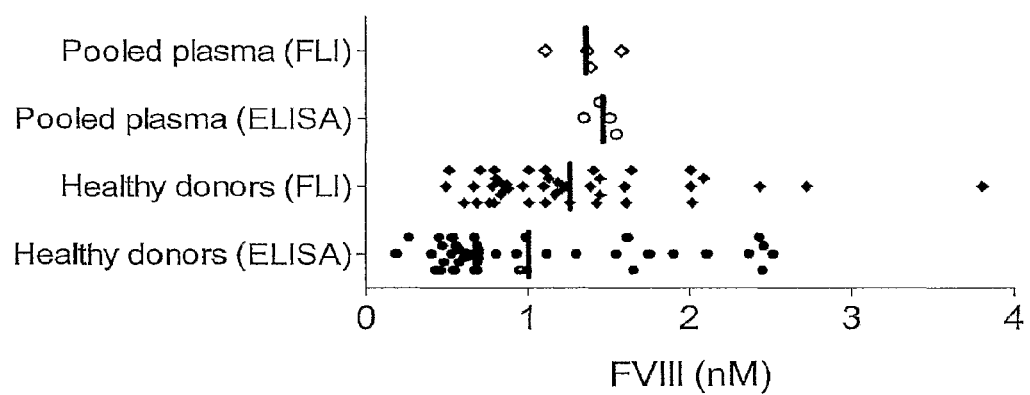
FIG. 16 is a graph showing a comparison of FVIII antigen levels as determined by ELISA and FLI, according to an embodiment of the invention, in plasma of a healthy human population.

It has been determined that the FLI can detect FVIII at concentrations at least about 3500-fold below normal physiological concentrations, and is about 300-fold more sensitive than ELISA. FIG. 16 shows a comparison of plasma FVIII antigen levels determined by ELISA and FLI in a healthy human population. More particularly, plasma FVIII concentrations were determined for 44 healthy blood bank donors in two double mAb immunoassays (ELISA and FLI) and compared. Vertical lines in FIG. 16 define the mean of FVIII concentration in the population tested. Pooled plasma was from 6 healthy individuals. Each point is the mean of duplicate determinations.

Detection of FVIII in human plasma at the level of sensitivity now achievable with the immunoassays of the invention should be sufficient to distinguish between the FVIII protein deficiency in hemophilia and non-functional FVIII mutants in which the mutations do not alter the epitope recognized by the mAb.

Figure 17:
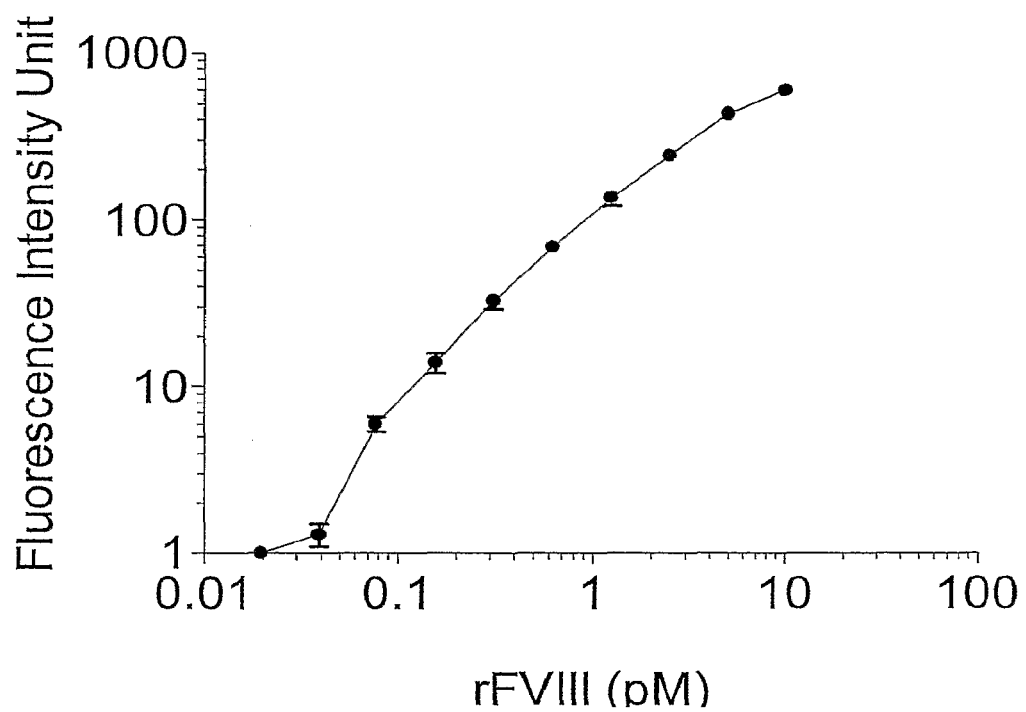
FIG. 17 is a graph showing highly sensitive detection of FVIII in a FLI according to an embodiment of the invention. Recombinant FVIII is detectable in the range of 1 pM and below.

FIG. 17 shows results of another high sensitivity FLI study in which the pattern of binding of rFVIII was measured in a double mAb fluorescence-based immunoassay. More particularly, rFVIII was spiked into FVIII-immunodepleted plasma and incubated in the presence of 10 mM β-mercaptoethanol for 2 hrs at RT. Binding of 50 ml of various concentrations of rFVIII (0.02-10 pM) diluted in buffer (PBS containing 0.1% BSA and 0.05% Tween 20) to anti-FVIII-68 beads (spectral address 038) and isotype matched control mAb-beads (spectral address 026) was determined simultaneously after probing of beads with biotinylated anti-FVIII-24 mAb and fluorophore-streptavidin. Specific signal was calculated after subtracting non-specific binding. Each point is the mean of 5 independent determinations.

Example 11

ELISA Assay for Measurement of Plasma Factor VIII and Use Thereof to Determine Factor VIII Concentration in Plasma from Healthy Individuals As discussed, the precise measurement of factor (F) VIII concentrations in human plasma is essential for diagnosis and classification of FVIII deficiencies and prothrombotic conditions. Bio-assays measure FVIII concentration indirectly and rely on the generation of activated FVIII (FVIIIa) via complex kinetic reactions in an individual substrate plasma.

In this Example we describe the development and use of an ELISA immunoassay that measures the FVIII antigen concentration in plasma in absolute quantitative terms not relying on other hemostatic components in plasma. The immunoassay is based upon the dissociation of FVIII and von Willebrand factor (vWF) by a reducing agent and the use of a calibrator generated by spiking a well defined, albumin free recombinant factor VIII into FVIII-immunodepleted plasma.

This Example further describes results of the ELISA assay performance evaluated by determining plasma FVIII antigen concentrations for healthy individuals and comparing the results to FVIII concentrations obtained by bioassays (activated partial thromboplastin time, APTT and chromogenic assays). The reliable detection limit of FVIII by our ELISA is ~60 pM. The assay gives equivalent results with natural FVIII including those containing vWF and with recombinant full-length FVIII products and concentrates.

Briefly, immunoassay data give a mean plasma concentration of 1.2±0.6 nM FVIII. This value is significantly higher than that obtained by APTT (0.65±0.6 nM) or chromogenic (0.5±0.2 nM) methods. The FVIII ELISA can quantitate FVIII concentrations as low as 5% of the mean physiological concentration. and is suitable for precise determination of FVIII antigen concentration in healthy individuals, mild and moderate hemophilia patients and for FVIII concentrates including those containing vWF. Details of these experiments are presented below.

Introduction

Factor VIII (FVIII) activity assays (bio-assays) are utilized for identification of FVIII deficiency/hemophilia and as monitors of an individual response to FVIII replacement therapy. However, the precision and reproducibility of these assays are a source of controversy [1,2]. Currently, one-stage clotting (APTT) and chromogenic (generation of FXa) assays are used for FVIII activity in plasma. Both assays measure FVIII concentration indirectly [1,3-14]. The significant discrepancies among these activity-based assays [1] arise from the differences in the sensitivity, specificity, standards, source of reagents, variations in the protocols, the nature of FVIII concentrates [12-16] and the instability of activated FVIII (FVIIIa) [17]. More importantly, activity assays involve a complex array of kinetic reactions that rely upon the plasma composition of FVIII congenitally deficient plasma and/or plasma from healthy individuals made chemically deficient for FVIII. Assay expression involves complex kinetic reactions which are influenced by the overall composite and qualitative levels of other plasma factors [18]. Thus, when an APTT assay is used to quantify FVIII products, different clotting values could be produced which results in reduced assay reproducibility and precision.

The FVIII concentration in normal plasma is assigned to be 1 unit $mL^{-1}$ (0.7 nM, 0.2 µg $mL^{-1}$) [7]. This concentration of FVIII is sufficient for procoagulant function in healthy individuals [7]. Substantial reduction or absence in circulating FVIII concentration leads to the bleeding disorder, hemophilia A. Hemophilia affects approximately 1 in 5000 males [19-21]. FVIII circulates in the plasma with the binding protein, von Willebrand factor (vWF) [7,8,22,23]. This non-covalent binding enhances FVIII synthesis, protects FVIII from proteolysis and concentrates FVIII at sites of active hemostasis [21]. However, the association of FVIII with vWF has hampered efforts related to immunoassay development for quantitative analysis of FVIII antigen concentration in plasma. Precise determination of FVIII antigen concentration and its relation to specific activity is critical for the diagnosis of individuals with pro-thrombotic conditions, FVIII deficiency, and for predictions of the bleeding episodes and management of hemophilia A.

Current immunoassays of FVIII use polyclonal antibodies (Abs) to bypass steric hindrance of FVIII epitopes by vWF. One major problem with such poly-specific Abs is the lack of specificity. Assays that utilize monoclonal Abs (mAbs) and can quantify plasma FVIII protein directly and in absolute quantitative terms are therefore highly desirable.

As described in Examples above, we have developed a double mAb immunoassay system for the determination of FVIII concentration in absolute quantitative terms. This assay relies on irreversible dissociation of FVIII from vWF using 10 mM β-mercaptoethanol (BME) [24]. In studies described in this Example, we evaluated assay performance by determining the concentration ranges of total FVIII for healthy individuals (n=44) using an immunoassay of the invention. The results were compared with those of conventional one-stage clotting (APTT) and chromogenic assays. In all assays, we used a batch of highly pure albumin-free recombinant FVIII (rFVIII) as calibrator. The concentration of this rFVIII had been confirmed by absorbance at 280 nm, by its 1:1 binding stoichiometry with factor IXa (FIXa) and by SDS-gel analysis. Our results define real plasma FVIII protein concentration in absolute quantitative mass.

Materials and Methods.

Proteins

Albumin-free recombinant (r) FVIII (MW 285 kDa, stock concentration 2.2 µM, 3143 U $mL.-^1$, 5000 units $mg^{-1}$, a gift from Dr. R. Lundblad, Hyland Division, Baxter Healthcare Corporation, was used as calibrator in all immunoassays and bio-assays. Immunate® (plasma-derived FVIII containing 40-fold molar excess of vWF established by ELISA, stock concentration contained 95 nM FVIII, established by ELISA, or 100 units $mL^{-1}$ reported by the manufacturer) and Refacto® (B-domain-deleted rFVIII, MW 170 kDa, stock concentration contained 68 nM protein established by 1:1 functional binding stoichiometry with activated factor IX (FIXa) [25], or 200 units $mL.-^1$ reported by the manufacturer) were obtained from Baxter Healthcare Corporation (Westlake Village, Calif.). Immunate and ReFacto were used for partial epitope mapping and their concentrations were determined by ELISA using albumin-free full-length rFVIII as calibrator and by their 1:1 binding stoichiometry with FIXa ([25], see below).

Production of FVIII-Specific Monoclonal Antibodies (mAbs)

As described in Examples above, a series of monoclonal antibodies (mAbs) directed against human factor VIII (FVIII) were produced in Balb/c mice. Immunization protocols and mAb production methods were similar to those reported previously [26]. Production and characterization of FVIII light-chain specific mAb clone 68 was reported previously [27]. All FVIII clones exhibited apparent affinities in the range of 49-160 nM and two clones 1 and 68 could be used in immunoblotting for structural analysis of full-length FVIII and FVIII fragments and epitope mapping. Epitope mapping using various forms of FVIII such as full-length rFVIII, activated rFVIII (rFVIIIa), ReFacto (B-domain deleted FVIII), FVIII-von Willebrand factor (vWF) complex (Immunate) in conjunction with immunoblotting indicated that anti-FVIII-1 mAb recognizes an epitope in the FVIII B-domain but anti-FVIII-68 recognizes a region in FVIII light chain. Clone 24 binds to full-length FVIII, FVIIIa, ReFacto, and Immunate equally well, but it does not blot with FVIII, thus epitope specificity of this mAb could not be assessed. Clone 23 recognizes activated FVIII preferentially as compared to full-length rFVIII. Anti-FVIII mAbs 20, 21, 23 and 25 all reacted with ReFacto (B-domain depleted FVIII) thus their epitope specificity was mapped to FVIII heavy or light chain. Because these mAbs do not react with FVIII in immunoblotting, we could not map their epitopes any further.

Plasma FVIII

Freshly frozen citrated plasma from Red Cross blood bank donors at the Fletcher Allen Health Center, University of Vermont was used for immunoassays of FVIII. The donors were Caucasian, reflecting the population in Burlington, Vt. Human studies were approved by the Institutional Review Board at the University of Vermont. For FVIII immunoassays, plasma was diluted 2-fold in PBS buffer (0.1 M sodium phosphate, 0.15 M NaCl, pH 7.2) containing 0.1% BSA (bovine serum albumin) and 0.05% Tween 20 (Sigma, St. Louis, Mo.) and reduced with 10 mM β-mercaptoethanol (BME, Sigma) for 2 hrs at room temperature (RT). Various dilutions were made in PBS buffer and added to the wells of microtiter plate pre-coated with capture mAb (described below).

FVIII-Deficient Plasma

FVIII-immunodeficient plasma was prepared in house by reduction of citrated pooled plasma from healthy individuals with 10 mM BME for 2 hrs at room temperature followed by FVIII depletion using anti-FVIII mAb columns. Performance of our in-house immunodepleted plasma was compared to that of commercially available immunodepleted plasma (purchased from PrecisionBiologic, Lot# D8-09, Dartmouth, Canada). Preliminary studies determined that patterns of binding of mAbs to increasing concentrations of rFVIII (0-4 nM) in both plasmas were indistinguishable as determined by ELISA. For FVIII bio-assays (APTT and chromogenic Coatest), congenitally FVIII deficient plasma was purchased (Lot # GK 0884-N8d1, George King Bio-Medical Inc., Overland Park, Kans.).

Validation of Albumin Free rFVIII

The titration behavior of the rFVIII (used as standard in all assays) in an intrinsic FXase assay is described elsewhere [25,28]. This albumin free rFVIII was used as standard in immunoassays and bio-assays. The concentration of rFVIII was ascertained by absorbance at 280 nm (using an extinction coefficient of 1.3) [29,30], by its 1:1 functional stoichiometry with factor IXa (FIXa) (calculated from the Scatchard plot of bound FVIIIa (nM) vs. bound/free) [25,28] and by SDS-gel and immunoblot analyses.

Figures 18A, 18B:
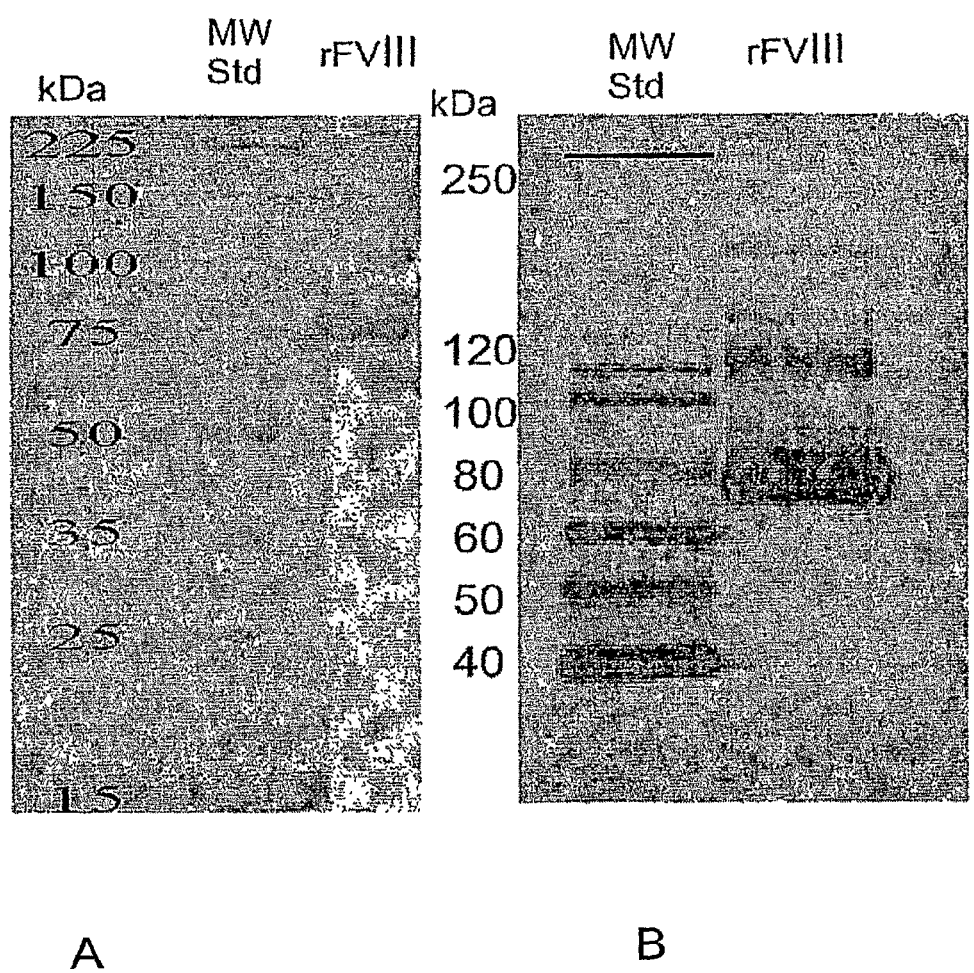
FIG. 18A-B is two photographs showing SDS-gel electrophoresis (18A) and immunoblot (18B) analysis of rFVIII used as calibrator in FLI and ELISA.

FIG. 18 shows SDS-gel electrophoresis (18A) and immunoblot analysis (18B) of rFVIII. Referring to FIG. 18A, twenty μg rFVIII was subjected to SDS-PAGE under reducing conditions. rFVIII dissociated into several high molecular weight fragments with apparent molecular masses of 225, 150, 100, 85 and 75 kDa corresponding to heavy and light chain fragments [45]. The absence of the degradation products (<75 kDa) indicates that the protein is pure. FIG. 18B illustrates the corresponding immunoblot of rFVIII under non-reducing condition. FVIII fragments were detected using mAb clones 1 (B-domain specific) and 68 (light chain specific).

Immunoassays

Enzyme-Linked Immunosorbent Assays (ELISA) of FVIII

Solid-phase direct binding assays were used to evaluate binding of anti-FVIII mAbs to FVIII and to determine the mAb binding region [31]. Purified mAb solutions were added to the wells of microtiter plates (U bottom Falcon plates, Becton Dickinson Labware, NJ, USA) pre-coated with rFVIII, activated FVIII (FVIIIa) and ReFacto. Binding was probed using horseradish-peroxidase (HRP)-anti-mouse IgG (Sigma) and detected by a chromogenic substrate (KPL, Gaithersburg, Md.).

Competition ELISA were performed in the absence or presence of rFVIII (0-200 nM) as previously described [31]. The relative affinity ($IC_{50}$) is the FVIII concentration that inhibits 50% of the binding of a mAb to immobilized FVIII.

For the double mAb ELISA, anti-FVIII-68 mAb (IgG$_2$b, κ, $IC_{50}$=60 nM) was immobilized in the wells of PVC microtiter plate (50 μl/well of 5 μg mAb mL$^{-1}$ PBS) [31]. Plasma from healthy individuals were spiked in FVIII immunodepleted plasma containing 10 mM BME (final concentration), mixed for 2 hrs at room temperature, diluted in PBS and 50 μl of each dilution was added to the pre-coated wells. Binding was probed with biotin-labeled anti-FVIII-24 mAb (IgG1, κ, $IC_{50}$=103 nM, 50 μl, 5 μg mL$^{-1}$) and detected using HRP-streptavidin (Sigma, 0.5 μg/ml, 50 μl) and a chromogenic substrate.

Plasma FVIII concentrations were determined using a calibration curve of rFVIII. rFVIII (10 nM) was spiked into FVIII immunodepleted plasma in the presence of 10 mM BME, diluted in buffer (0-4000 pM) and subjected to double mAb immunoassay as described above.

Immunoblotting

Immunoblotting was utilized as a complementary approach to assess the blotting capabilities and epitope specificity of each mAb. Various FVIII products were subjected to electrophoresis on a gradient SDS-PAGE (5-15%) and blotted using different anti-FVIII mAbs [31] FIG. 18 illustrates a selected immunoblot for rFVIII probed with a mixture of two mAbs, clone 1, B-domain specific, and clone 68, light chain specific).

Bioassays

Activated Partial Thromboplastin time (APTT) was performed using a kit from bioMérieux (Durham, N.C.).

Coatest® factor VIII (Chromogenix, Lexington, Mass.) was used for the determination of FVIII activity in citrated plasma as described by the manufacturer. Plasma FVIII activity (nM) in both APTT and chromogenic assay was calculated from their corresponding calibrators generated by spiking various molar concentrations of rFVIII into congenitally FVIII deficient plasma (Lot # GK 884-N8d1). In both assays, plasmas were diluted 5- to 40-fold in the same FVIII deficient plasma.

Results.

Evaluation of FVIII ELISA

Addition of 10 mM BME to plasma results in the exposure of FVIII epitopes for mAb binding [24]. This concentration of BME does not interfere with Ab binding to FVIII as assessed by comparing the binding pattern of albumin-free purified rFVIII in the absence or presence of BME which proved to be comparable (data not shown). The optimum concentration of BME was established following extensive analyses of the FVIII ELISA assay performance in the presence of various concentrations of BME (0-35 mM). All immunoassay experiments reported herein were performed in the presence of 10 mM BME during assay.

Figure 19:
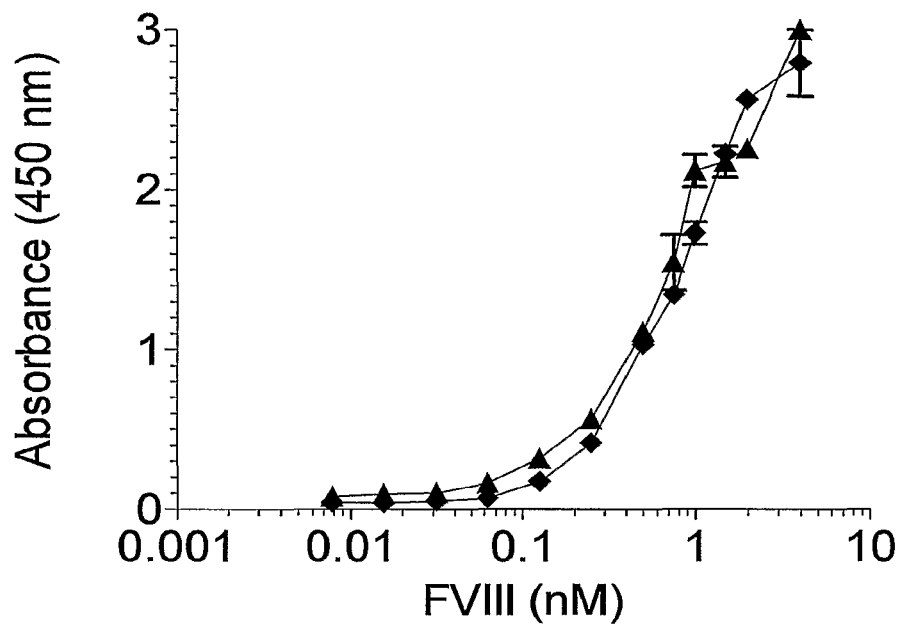
FIG. 19 is a graph showing comparison of binding patterns of equimolar concentrations of rFVIII and Immunate, according to an embodiment of the invention.

For the double mAb ELISA, anti-FVIII-68 mAb was immobilized in the wells of microtiter plates. Binding of rFVIII, Immunate or human plasma FVIII was probed using biotinylated anti-FVIII-24 mAb and HRP-streptavidin. FIG. 19 illustrates a calibration curve for rFVIII from seven independent experiments. More particularly, FIG. 19 shows a comparison of binding patterns of equimolar concentrations of rFVIII and Immunate. Four nM rFVIII (▲), or Immunate (♦) was spiked into FVIII-immunodepleted plasma, diluted 2-fold with PBS buffer containing 0.1% BSA and 0.05% Tween 20 and reduced with 10 mM BME for 2 hrs. Proteins were diluted further in the same buffer and subjected to immunoassay as described in Materials and Methods.

The results show that anti-FVIII-68 and 24 mAbs, which bind to spatially and structurally distinct epitopes on FVIII, can capture (anti-FVIII-68 mAb) and detect (anti-FVIII-24 mAb) rFVIII in a concentration-dependent manner. The reliable detectability limit of this assay is in the 60 pM (17 ng mL$^{-1}$) range, assuming an average molecular mass of 285 kDa for rFVIII [9]. The coefficient of variance (CV %) for 7 independent experiments performed over a period of 4 weeks was 12±5% for FVIII concentrations between 0.06-4 nM.

FIG. 19 also illustrates that the presence of excess molar concentration of vWF does not interfere with FVIII binding, as the binding patterns of equimolar concentrations of Immunate (contains >40-fold molar excess of vWF) and rFVIII (no vWF) are similar.

Figure 20:
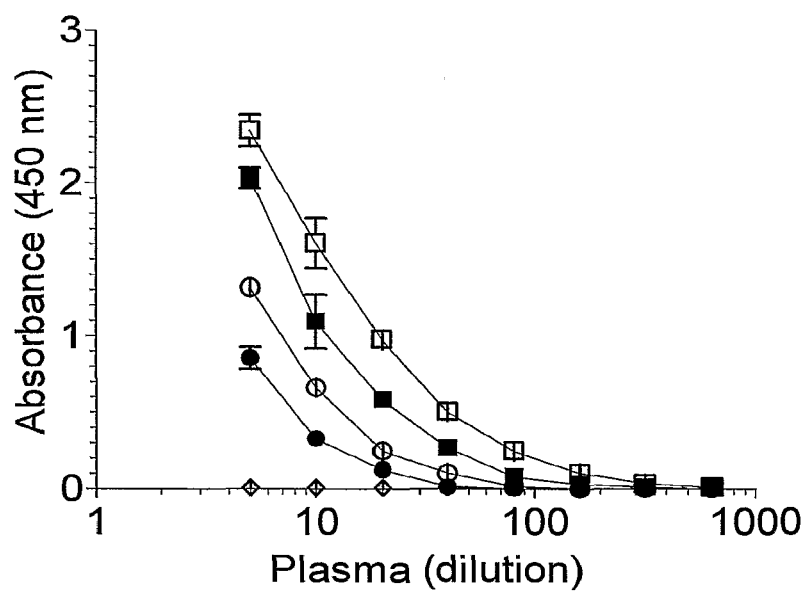
FIG. 20 is a graph demonstrating the ability to detect different molar concentrations of rFVIII that have been added to plasma from normal human donors, according to an embodiment of the invention.

Assay reproducibility and precision were further confirmed by a quality control that included repeated measurements of FVIII concentration in plasma that was pooled from five healthy donors (FIG. 20). More specifically, FIG. 20 shows the additive effect of spiking various molar concentrations of rFVIII in plasma pooled from five donors. Plasma was spiked with 0 (●), 1.0 (○), 3.0 (■) or 6.0 (□) nM rFVIII, diluted 2-fold in buffer and reduced with 10 mM BME and the various dilutions were subjected to immunoassay. FVIII immunodepleted plasma (◇) was used as specificity control. Each point shown in FIG. 20 is the mean of duplicate determinations±SD. FVIII concentration was determined from a calibration curve of rFVIII similar to that used in FIG. 19.

The concentration of FVIII in this plasma was determined to be 1.2±0.1 nM (CV %⁻8%), calculated from a calibration curve of rFVIII similar to that shown in FIG. 19. In addition, it was found that the assay was sensitive to variations in FVIII concentration, as spiking various rFVIII concentrations into normal plasma resulted in an additive effect on plasma FVIII concentration proportional to the amount of FVIII added to plasma (FIG. 20). Plasma FVIII concentration following spiking of 1.0, 3.0 and 6.0 nM rFVIII was 2.0, 4.0 and 7.6 nM, respectively, which approximates the plasma FVIII concentration (1.2 nM) plus the FVIII concentration added.

FVIII Antigen Levels in a Healthy Population

Figure 21:
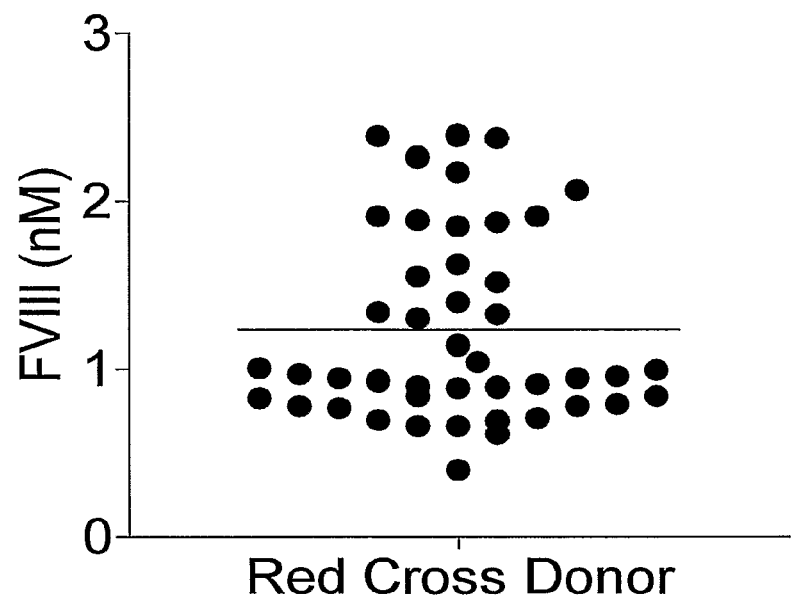
FIG. 21 is a plot showing FVIII concentration and ranges in a healthy human population, determined in accordance with an embodiment of the invention.

To evaluate the mean FVIII antigen concentrations, and concentration ranges in a healthy population, antigen levels were determined for 44 individual blood donors. The results are shown in FIG. 21. Plasma was diluted 2-fold with buffer, reduced with 10 mM BME and subjected to immunoassay as described above. Concentration of FVIII was determined as described for FIG. 20. Each point represents the mean of two independent determinations. FIG. 21 illustrates that normal FVIII concentration ranges are between 0.4 and 2.5 nM, with a mean value of 1.2±0.6 nM. These data indicate that there are significant variations in FVIII concentration among healthy individuals, and that the FVIII immunoassay of the invention is sensitive to these variations (FIG. 21).

Figure 22:
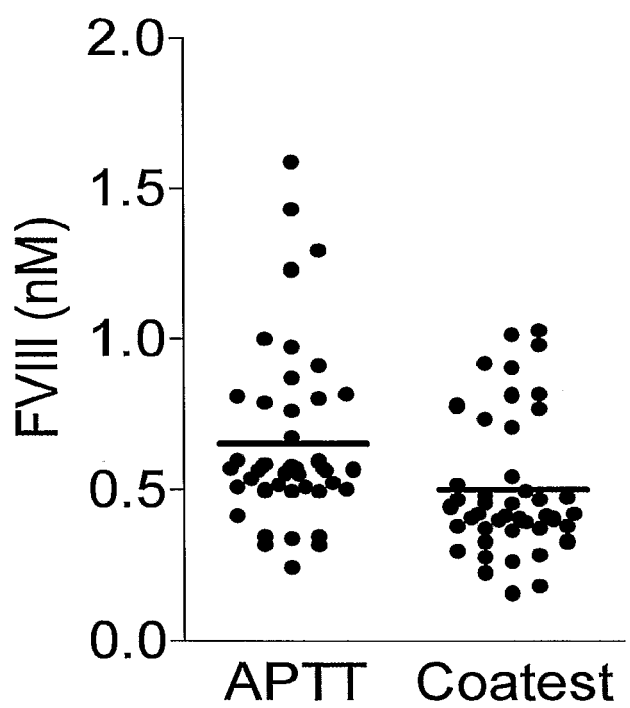
FIG. 22 is a plot showing the concentration and ranges of plasma FVIII as determined by prior art APTT and chromogenic assays.

FVIII Concentration in the Healthy Population Determined by APTT and Chromogenic Assay FIG. 22 shows determination of the concentration of plasma FVIII as assessed by APTT and chromogenic assay. The calibrators for both APTT and chromogenic assays were generated by spiking rFVIII into FVIII congenitally deficient plasma and used to calculate FVIII concentrations. For each individual, clot time and generation of FXa were determined in duplicates. Calibration curves were generated by spiking various molar concentrations of rFVIII (0-700 nM) into FVIII congenitally deficient plasma and subjected to assay by APTT and Coatest.

Referring to FIG. 22, the plasma FVIII concentration for the same healthy individuals using the APTT assay was determined to range from 0.24-1.6 nM, with a mean value 0.65±0.3 nM. With the assumption that the pooled normal plasma contains 100% FVIII activity, this molar concentration is equivalent to 97±44% FVIII activity in the healthy individuals.

With the Coatest chromogenic assay, FVIII concentration range was between 0.16 and 1.0 nM, with a mean value of 0.5±0.2 nM (FIG. 22). In the chromogenic assay, this molar concentration of FVIII corresponds to 72±30%, based on activity.

Figure 23A:
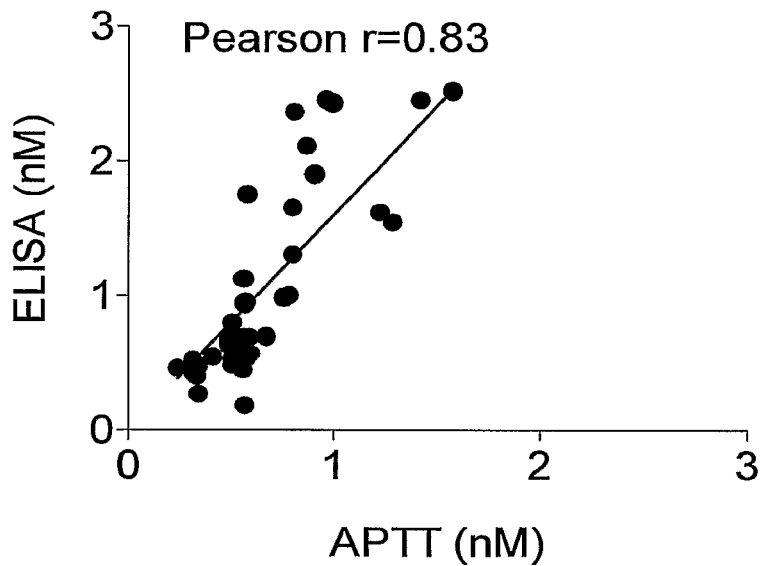
FIG. 23A-D is four graphs showing correlations of FVIII antigen concentration as determined by immunoassay in accordance with the invention and as determined by APTT and chromogenic assays.
Figure 23B:
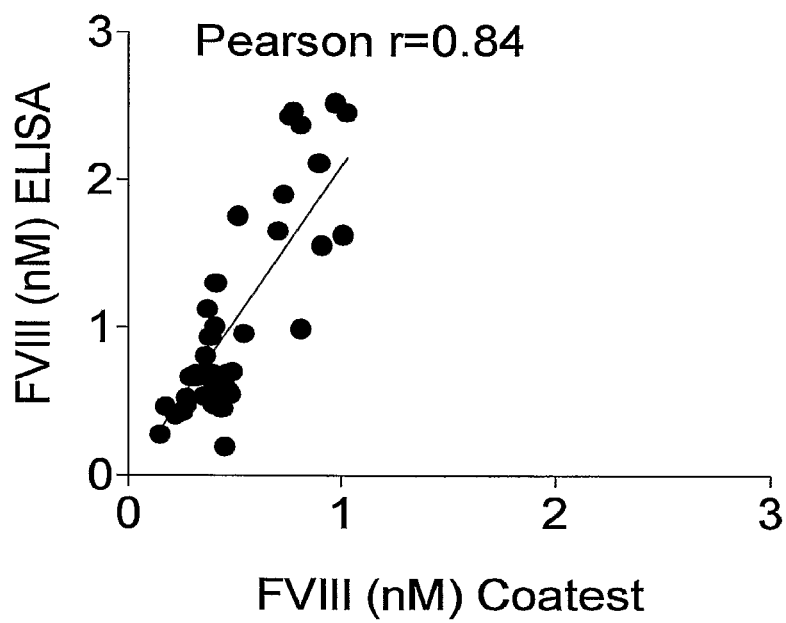
Figure 23C:
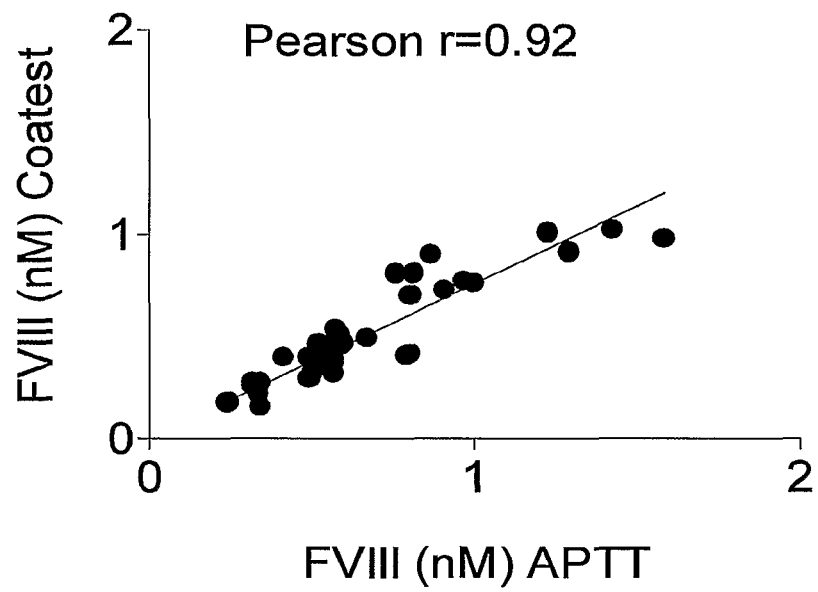

FIG. 23 shows correlation of FVIII antigen concentration by immunoassay with concentration determinations by APTT (FIG. 23A) and chromogenic assay (FIG. 23B). FIG. 23C illustrates the correlation between APTT and chromogenic assay, and FIG. 23D compares the FVIII concentration of each individual determined by immunoassay with that determined by the chromogenic assay. These results show that despite the higher plasma FVIII antigen concentrations obtained by ELISA, comparison of FVIII antigen concentration by ELISA and by APTT demonstrates a linear correlation with Pearson r value of 0.83 and r squared value of 0.69 (FIG. 23A). A similar linear correlation was observed upon comparison of FVIII antigen concentration determined by ELISA and by the Coatest chromogenic assay (Pearson r value, 0.84 and r squared value of 0.7) (FIGS. 23B and 23D). The Pearson r value of 0.92 was obtained when FVIII concentrations were compared between APTT and Coatest (FIG. 23C).

Overall FVIII antigen immunoassay data demonstrate that the FVIII antigen molar concentration in plasma is higher than that obtained either by APTT or by the Coatest chromogenic assay, suggesting that some FVIII is circulating in an inactive form.

Advantageous Features of Immunoassay System for FVIII.

We have developed a specific and sensitive double mAb immunoassay format by which plasma FVIII concentrations can be quantified at concentrations as low as 60 pM. One advantageous feature of the immunoassay is the use of 10 mM BME, which results in the irreversible dissociation of vWF from FVIII. This is thought to eliminate the binding interference by vWF (FVIII binding protein) that might otherwise sterically hinder FVIII epitopes involved in mAb binding.

The invention provides for the first time an assay of plasma FVIII concentrations in absolute quantitative terms. This was achieved using a rFVIII calibrator that contained only FVIII protein and exhibited 100% activity based on a 1:1 functional stoichiometry with FIXa [25,28].

The mean values for the concentration of total FVIII and that of active FVIII were determined by immunoassay and two activity-based assays for 44 healthy individuals. The results demonstrated that while FVIII concentration values based upon activity assays are consistent with the commonly accepted mean value for plasma FVIII (0.7 nM or 1 unit mL$^{-1}$ or 0.2 μg mL$^{-1}$ or 100%) [7,21,32-34], immunoassay data indicated that the FVIII antigen concentration is significantly higher (1.2±0.6 nM) than that observed in either APTT or chromogenic assay (0.65±0.3 and 0.5±0.2 nM, respectively). These data suggest that a fraction of the FVIII protein in citrated plasma is not detected by either bio-assay. It must be emphasized that FVIII concentrations in all three assays were estimated using a well characterized rFVIII standard [25,28]. This has minimized assay variations that could occur due to the use of different plasma pools as calibration curves and provided an opportunity to determine FVIII concentration in absolute quantitative mass. Variations between APTT and chromogenic assays were further minimized using a single lot of FVIII congenitally deficient plasma.

Figure 23D:
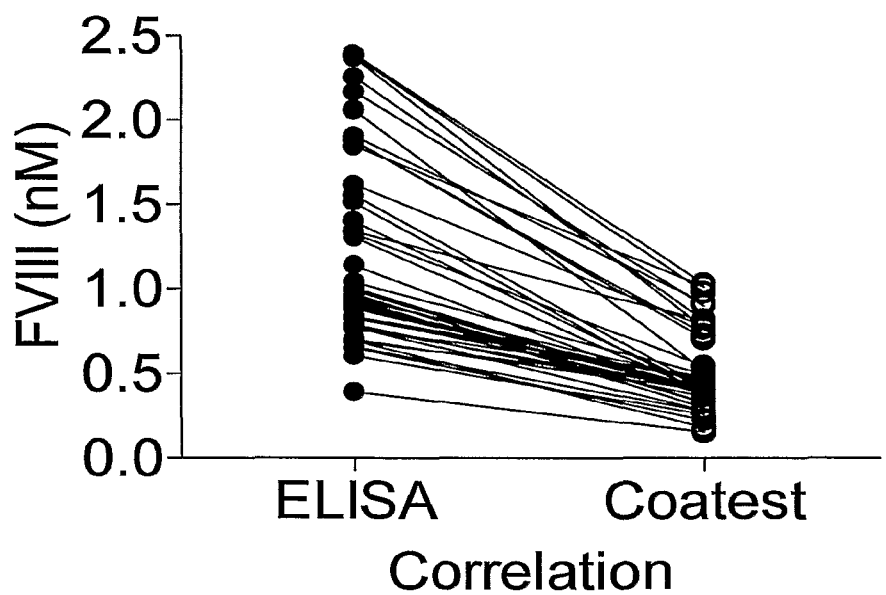

Comparative analyses between results of the immunoassay and APTT indicated that 38 out of 44 plasmas (86%) had higher FVIII antigen levels than activity. Similarly, when immunoassay results were compared to the results of the chromogenic assay, 43/44 plasmas (97%) showed higher FVIII antigen and only 1/44 plasma had higher FVIII activity than antigen (FIGS. 23B and 23D). The observation that the vast majority of plasmas contain higher levels of FVIII antigen than activity is consistent with the notion that a significant fraction (35-50%, based on comparison of FVIII concentration in immunoassay with that in APTT or chromogenic assay) of FVIII is not quantitatively represented in either activity assay.

Without intending to be bound by theory, one possible explanation is that in activity assays, human FVIIIa heterodimer, which is unstable, rapidly loses activity due to the spontaneous dissociation of the A2 fragment from the A1/A3-C1-C2 dimer [35-37]. While FVIIIa is produced during the initiation phase of thrombin (IIa) generation [38,39], it continuously dissociates from FIXa. Therefore, FVIIIa concentration as determined by APTT will not reach the actual FVIII concentration in plasma, and thus activity-based assays are unable to measure the actual FVIII concentration in plasma of healthy individuals. Alternatively, it is possible that a fraction of FVIII may be inactive in plasma.

A double mAb immunoassay for the quantitation of FVIII in plasma has been reported which requires that the capture mAb be in a form of an $(Fab')_2$ fragment to minimize cross-reactivity with rheumatoid factor [32]. The international standard plasma was taken as reference and considered as 1 unit $mL^{-1}$ (0.7 nM) both for FVIII activity and antigen in that study. Plasmas from normal donors compared to this reference plasma contained 1.2 U $mL^{-1}$ by activity assay and 1.01 unit $mL^{-1}$ antigen by immunoassay. Thus, the concentration of FVIII antigen calibration curve was based on the activity, whereas the FVIII antigen concentrations reported herein are based on measurements of FVIII mass and stoichiometry of FIXa binding.

Elevated plasma FVIII concentration is implicated in some prothrombotic states [40-42]; thus it is important to evaluate plasma FVIII concentrations by an immunoassay which bypasses the interferences associated with variations in coagulation profiles of substrate and patients' plasmas, and variations in the levels of FVIII activation. In addition, immunoassays of the invention are an important tool for FVIII concentration determinations in plasma of patients who have prolonged APTTs due to the presence of other anti-coagulant antibodies such as lupus erythematosus [43,44].

Example 12

Use of Fluorescence-Based Immunoassay (FLI) to Determine Plasma Factor VIII Concentration in Hemophilia Patients This Example describes the use of a highly sensitive fluorescence-based assay in accordance with the invention and as described above (see, for instance, Examples 8 and 9) to detect very low levels of Factor VIII present in the plasma of patients with blood clotting disorders such as hemophilia, as well as levels of Factor VIII found in healthy subjects.

Introduction.

Hemophilia A is a clinically heterogeneous disorder due to the large number of different molecular defects in the factor (F) VIII gene. In severe Hemophilia A patients, this heterogeneity is amplified due to variations in FVIII concentration below 1% physiological concentration. This is evident from considerable differences in bleeding tendency among these patients. As discussed, the clinical diagnosis of hemophilia A relies on the bio-assays that are not sensitive at FVIII concentrations<1% physiological concentration. Bio-assay measurements are complicated by many variables including differences in plasma coagulation factor concentrations among individuals, substrate plasmas, presence of inhibitors of coagulation proteins including lupus antibodies, and complications related to the labiality of activated FVIII (FVIIIa). As described above, we have developed a fluorescence-based immunoassay (FLI) that can measure FVIII antigen concentration in plasma in absolute quantitative terms that do not rely on other hemostatic components in plasma. The reliable detection limit of FLI is 2 pM, which is significantly lower than 1% mean physiologic FVIII concentration (~1.2 nM).

The human factor VIII (FVIII) glycoprotein plays a key role in conversion of factor X (FX) to activated FX (FXa) in the intrinsic pathway of blood coagulation. In plasma, FVIII circulates at low concentration and is bound to von Willebrand factor (vWF) (Hoyer, 1981; Kane and Davie, 1988; Sadler and Davie, 1987). Concentration of FVIII in plasma of healthy individuals is reported to be in the range of 1 unit/ml (usually translates into 0.7 nM or 0.2 µg $mL^{-1}$) (Hoyer, 1981; Hoyer, 1994; Tackaberry et al., 1987). By comparison to FVIII concentration in healthy individuals, FVIII deficiencies are classified as severe (<1%), moderate (1-5%), and mild (>5%). In severe hemophiliacs, FVIII concentration is less than 1% physiological concentration (>0.01% unit $mL^{-1}$ or <7 pM/0.002 µg $mL^{-1}$).

Management of severe hemophilia is particularly challenging due to lack of sensitive and reproducible assays that can quantify FVIII concentrations at below 1% normal physiological concentration in plasma. This is increasingly important as new modes of therapy such as continuous FVIII infusion, gene therapy, FVIII mutation correction and other prophylactic approaches are developed (Chuah et al., 2004; Gilchrist et al., 2001; Hawkins et al., 1995; Hurst et al., 1998).

As discussed above, most common quantitative assays of plasma FVIII and FVIII concentrates are based on bio-assays such as one stage clotting (APTT) and chromogenic (generation of FXa) assays that measure FVIII concentration indirectly (Chavin and Fay, 1989; Hoyer, 1981; Kane and Davie, 1988; Kemball-Cook et al., 1993; Langdell et al., 1953; Lenting et al., 1998; Niemetz and Nossel, 1969; Over, 1986). FVIII concentration in bio-assays is estimated from a reference calibration curve generated from normal plasma pools of healthy individuals. This leads to discrepancies and inconsistencies in the assay results, presumably due to variability in plasma FVIII and other components of different plasma pools. In addition, bio-assays are less sensitive with respect to differentiating among severe hemophilia patients (FVIII concentration of <1% physiological concentration). This is important because plasma FVIII concentration in severe hemophilia patients can vary between 0-12 pM, compared with an average of 1.2 nM concentration for a healthy population. It is reported that this variability in FVIII concentration plays an important role in the bleeding tendency and requires a different treatment strategy among hemophiliac patients. Petrini et al reported that prophylactic treatment in patients with severe hemophilia A (concentrations of FVIII below 0.01 IU $mL^{-1}$; <1% physiological concentration) can protect against bleeding (Petrini, 2001). Similarly, recent clinical trials of FVIII and FIX gene therapy have shown clinical efficacies at very low factor levels (Roth et al., 2001).

Accordingly, there is an unmet need for reliable and sensitive assays that can quantify plasma FVIII at concentrations significantly lower than 1% mean physiologic concentration. Such assays are needed in pharmacokinetic studies of FVIII replacement therapy, gene therapy and monitoring of FVIII antigen levels during infusion in order to avoid excess FVIII administration which could elicit neutralizing antibodies (Abs) to FVIII (El Alfy et al., 2000; Klinge et al., 2001; Lindgren et al., 2002; Scandella et al., 1998).

Example 11 above describes development and evaluation of an ELISA FVIII with reliable detection limit in the 60 pM range. This FVIII ELISA is useful for quantitative analysis of plasma FVIII in healthy individuals, as well as in mild and moderate hemophilia and FVIII concentrates. In order to increase assay sensitivity and the reliable detection limit, the FVIII ELISA was converted to a fluorescence immunoassay (FLI) and was integrated into the Luminex Multi-Analyte Platform to develop a sensitive and high throughput fluorescence-based FLI for detection and quantitation of FVIII in human plasma, as described, e.g., in Examples 8 and 9 above. This Example describes additional data from FLI assays regarding sensitivity, specificity, and detection limits both for normal plasma and that of hemophilia patients and patients with various pathological conditions including autoimmune diseases.

Materials and Methods

Proteins

Albumin-free recombinant (r) FVIII (MW 285 kDa, stock concentration 2.2 µM, 3143 U mL$^{-1}$, 5000 U mg$^{-1}$, a gift from Dr. R. Lundblad, Hyland Division, Baxter Healthcare Corporation), was used as calibrator in all immunoassays and bioassays. Immunate® (plasma-derived FVIII containing 40-fold molar excess vWF established by ELISA, stock concentration contained 95 nM FVIII, established by ELISA or 100 units mL$^{-1}$ reported by the manufacturer, Baxter Healthcare Corporation, Westlake Village, Calif.).

Production of FVIII-Specific Monoclonal Antibodies (mAbs)

A series of monoclonal antibodies (mAbs) directed against human FVIII were produced in Balb/C mice. Immunization protocols and mAb production methods were similar to those reported previously (Foster et al., 1983). FVIII light-chain specific mAb clone 68 has been described previously (Precup et al., 1991). Other mouse monoclonal antibodies were generated and immunochemically characterized as described, e.g., in Examples 1-4, supra.

FVIII-Deficient Plasma

FVIII-immunodeficient plasma was either purchased from PrecisionBiologic (Lot # D8-09, Darmouth, Nova Scotia, Canada) or prepared in house by reducing citrated pooled plasma from 5-6 healthy individuals with 10 mM β-mercaptoethanol for 2 hrs. FVIII was depleted using anti-FVIII mAb columns.

Validation of Albumin Free rFVIII and Generation of Calibration Curve

Albumin free recombinant (r) FVIII (stock solution of 2.2 µM in HBS buffer (HEPES 20 mM, NaCl 150 mM, pH 7.3) was used as calibrator in all immuno- and bio-assay experiments. Concentration of rFVIII was ascertained by absorbance at 280 nm (using an extinction coefficient of 1.3) (Kumar et al., 2003; Pace et al., 1995), 1:1 functional stoichiometry with activated factor IX (FIXa, calculated from the Scachard plot of bound FVIIIa (nM) vs. bound/free) (Butenas et al., 2005; Parhami-Seren et al., 2004) and by SDS-gel and immunoblot analyses.

For preparation of the FVIII calibration curve, rFVIII (1 nM) was spiked into FVIII-immunodepleted plasma and diluted 2-fold in PBS buffer (0.1 M sodium phosphate, 0.15 M NaCl, pH 7.2) containing 0.1% BSA and 0.05% Tween 20. Following addition of 10 mM β-mercaptoethanol (BME) for 2 hrs, the sample was diluted further in FVIII-immunodepleted plasma (containing 10 mM BME). FVIII containing plasma samples were subjected to FLI (see below).

Plasma FVIII

For FVIII FLI, freshly frozen citrated plasma from Red Cross blood bank donors at the Fletcher Allen Health Center, University of Vermont, was used. The donors were Caucasian, reflecting the population in Burlington, Vt. Plasma from hemophilia patients were obtained from Dr. George E. Rivard (The Hopital Saint-Justine, Montreal, Canada) and Dr. Edward Gomperts (The Childrens Hospital, Los Angeles). Human studies were approved by the Institutional Review Board at the University of Vermont, Saint-Justine hospital and Childrens Hospital.

For FLI, plasma was diluted 2-fold in PBS buffer containing 0.1% bovine serum albumin (BSA) and 0.05% Tween 20 and reduced with 10 mM BME for 2 hrs at room temperature. Various dilutions were made in FVIII-immunodepleted plasma (also reduced with 10 mM BME to prevent vWF binding to FVIII), and added to the wells of microtiter plate containing mAb-beads as described below.

Fluorescence Immunoassay (FLI)

FLI FVIII ELISA was integrated into the Luminex Multi-Analyte Platform (LMAP) as described above. Briefly, microsphere beads with predefined 658:712 nm emission ratios (Luminex classification #038) were coupled to anti-FVIII-68 mAb (IgG2b, κ) according to the manufacturer's instructions (Luminex Corporation, Austin, Tex., USA). The binding of FVIII to mAb-beads was probed with biotinylated anti-FVIII-24 mAb (IgG1, κ) and detected using R-Phycoerythrin (PE) coupled-streptavidin as described above. Briefly, fifty µl of anti-FVIII-68 mAb-beads (5×10$^3$ beads, 50 µl) were added to the wells of a microtiter plate (wells were covered with 1.2 µm PVDF membrane, Multi-Screen filter plates, part # MABV-N1250, Millipore Corporation, Billerica, Mass.). Fifty µl of various concentrations of rFVIII or plasma dilutions in FVIII-immunodepleted plasma were added to the beads. Following a 3-hr incubation at room temperature, excess antigen was removed. One hundred µl of biotinylated anti-FVIII-24 mAb (10 µg mL$^{-1}$ PBS-1% BSA-0.05% Tween 20) was added for an additional 1 hr. Following three more washes, the beads were reacted for 30 min with PE-streptavidin (100 µl of 5 µg mL–$^1$ probe in PBS-1% BSA-0.05% Tween 20).

Non-specific binding controls were performed by using an isotype-matched mAb with a specificity irrelevant to FVIII, coupled to microsphere beads with a different 658/712 nm emission ratios (Luminex classification #027) than those used for anti-FVIII-68. The Luminex technology permits the specific and non-specific binding signal to be determined simultaneously in real time. Data are reported as Δ mean fluorescence intensity units, representing intensity for anti-FVIII mAb-beads minus that measured for control mAb-beads.

Bioassay

Activated Partial Thromboplastin time, APTT (bioMérieux, Durham, N.C.) was performed as described by the manufacturer. APTT calibrator was generated by spiking increasing concentrations of rFVIII into FVIII-immunodepleted plasma (PrecisionBiologic, Lot# D8-09) followed by clot time determination. In all immunoassays and bioassays, a single lot of FVIII-deficient plasma was used and plasmas were diluted 1 to 40-fold in the same FVIII-deficient plasma.

Results

Evaluation of FLI

The success of this FLI relies in part on the addition of 10 mM BME to plasma to expose FVIII epitopes for mAb binding (Lollar et al., 1993). We have determined that this concentration of BME does not interfere with antibody binding. All immunoassay experiments described in this Example were performed in the presence of 10 mM BME during assay.

Figure 24A:
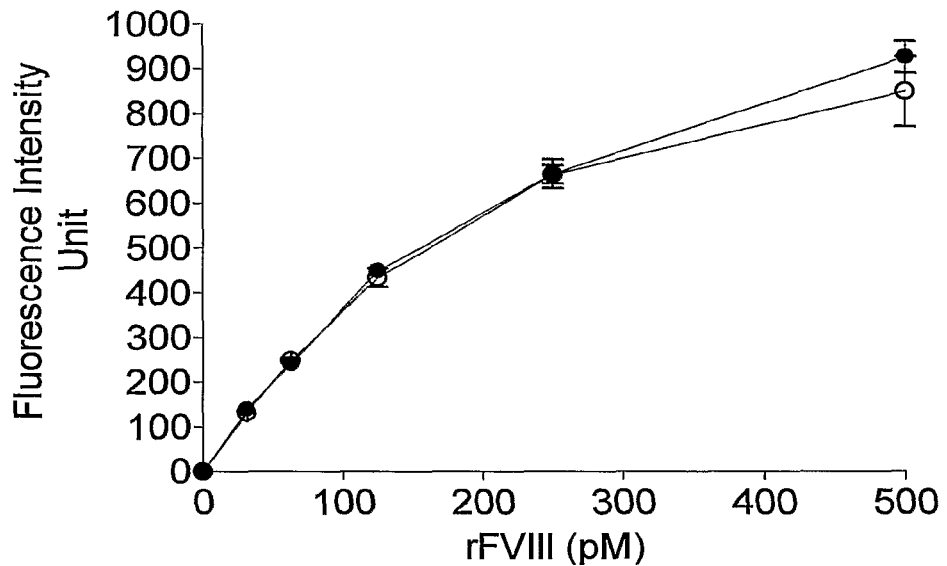
FIG. 24A-B is two graphs showing high (24A) and low (24B) calibration curves of recombinant FVIII, according to an embodiment of the invention.
Figure 24B:
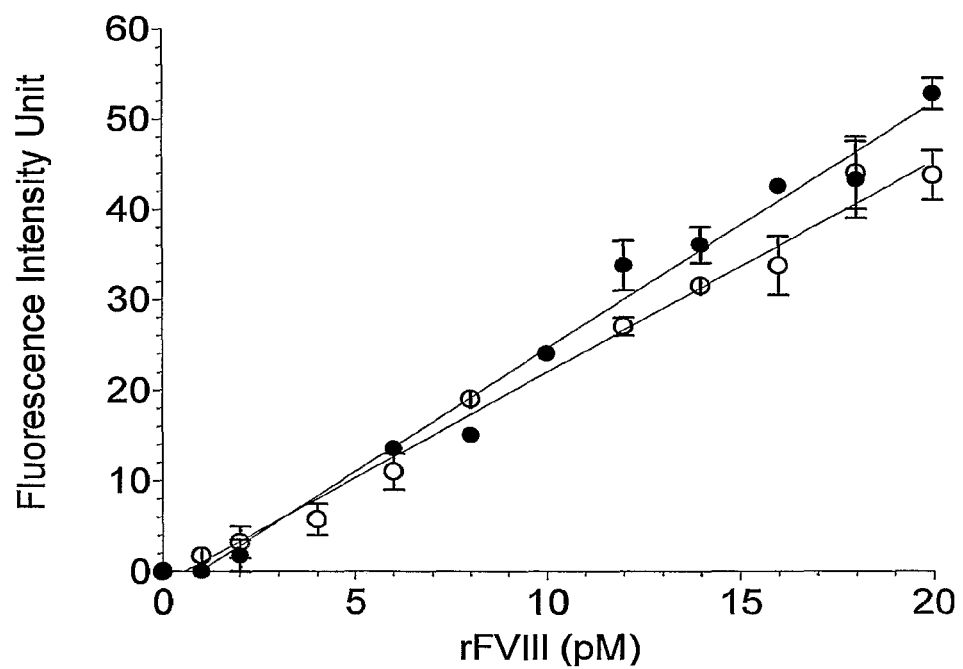

FIG. 24A shows a high range and FIG. 24B shows a low range calibration curve of rFVIII in immunodepleted plasma. rFVIII (0-500 pM) or (0.25-20 pM) was spiked into our in house (○) or commercial source (●, Pricision Biologic) FVIII-immunodepleted plasma. Plasma was reduced with 10 mM BME and subjected to FLI. Each point is the mean of 2-4 independent determinations±SD.

There is no significant difference between the calibration curve generated in our in house FVIII immunodepleted plasma and that generated in the FVIII-immunodepleted plasma from the commercial source (PrecisionBiologic). The difference between these two FVIII deficient plasmas is that our in house immunodepleted plasma is reduced with 10 mM BME before depleting FVIII with anti-FVIII mAbs and it also contains physiological concentrations of vWF. The Commercial plasma is depleted of FVIII using anti-vWF Abs; thus there is no detectable FVIII (established by ELISA and FLI) or vWF (established by ELISA).

We next tested the assay reliable detection limits in plasma. rFVIII concentrations ranging from 0.25-20 pM were spiked into FVIII-immunodepleted plasma and subjected to FLI. The reliable detection limit in whole plasma was in the 2 pM range. Overall assay coefficient of variation at concentrations between 2-20 pM was between 12-16%. Thus this FLI can measure FVIII concentrations significantly below 1% physiological concentration in plasma (FIG. 24B).

Figure 25A:
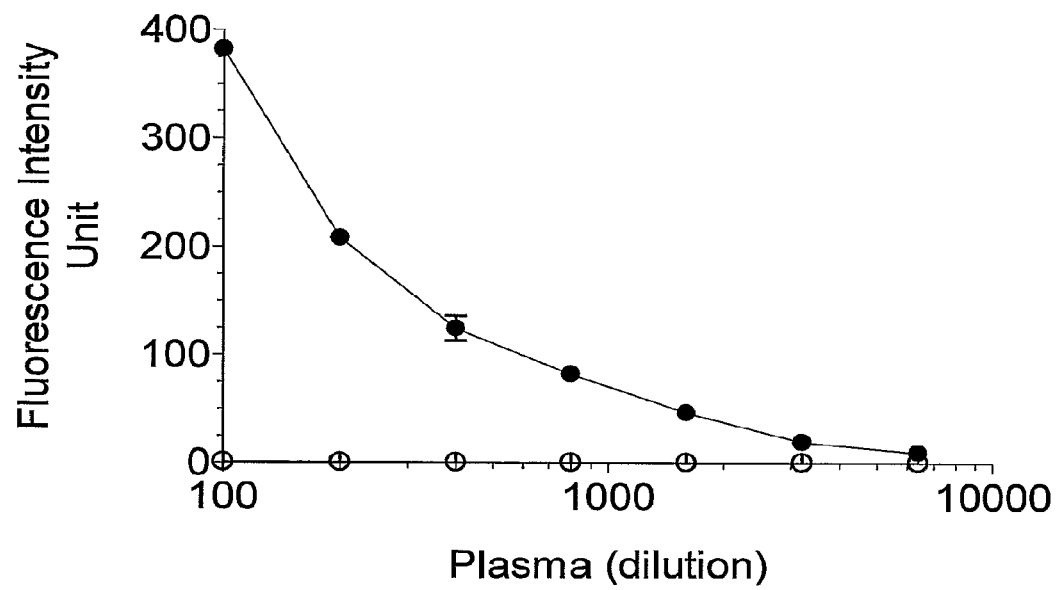
FIG. 25A is a graph showing the pattern of binding of pooled plasma from healthy donors as determined by a fluorescent immunoassay (FLI) in accordance with an embodiment of the invention.

The binding pattern of plasma FVIII pooled from 6 healthy individuals was evaluated to determine the physiological concentration of FVIII in plasma by FLI (FIG. 25A). Referring to FIG. 25A, pooled plasma from 6-donors (●) was diluted in immunodepleted plasma (1:1) and then in PBS buffer (2-fold), was reduced with 10 mM BME. Several dilutions were made in FVIII-immunodepleted plasma and subjected to FLI. Immunodepleted plasma (○) similarly treated was used as negative control. FVIII antigen concentration was determined from a calibration graph of rFVIII similar to that shown in FIG. 24A. Each point is the mean of duplicate determinations±SD.

A mean concentration of 1.3±0.2 (CV %=15%) was obtained from 4 independent experiments using a standard curve similar to that shown in FIG. 24B. This value is generally consistent with FVIII concentration obtained by ELISA (1.2±0.1 nM).

Figure 25B:
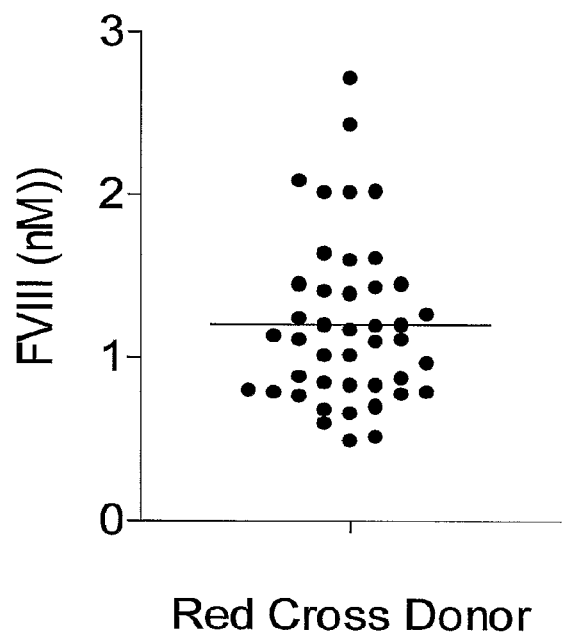
FIG. 25B is a plot showing plasma FVIII concentrations and ranges in a healthy donor population, measured by FLI.

We further evaluated FLI by measuring plasma FVIII concentration and ranges in the same 44 healthy individuals for which FVIII concentrations had been determined by ELISA, as described above. Data are illustrated in FIG. 25B. Plasma from red-cross donors (●) were diluted 2-fold in immunodepleted plasma and an additional 2-fold in PBS buffer, reduced with 10 mM BME and various final dilutions (500- and 1000-fold) were made in immunodepleted plasma and subjected to FLI. Mean FVIII concentration for healthy population was 1±0.4 nM. FVIII concentrations were determined from a calibration graph of rFVIII similar to that shown in FIG. 24A. Each point in FIG. 25B is the mean of concentrations obtained for 4-8 independent determinations±SD. The data indicate that there are significant variations in FVIII concentration among healthy individuals ranging from 0.3-2.1 nM, with a mean value of 1.0±0.4 nM. These data are generally consistent with FVIII concentration obtained by ELISA (FVIII concentration range 0.4-2.5 nM, with mean concentration of 1.2±0.6 nM). Overall, the results of FVIII FLI confirms our previous finding that the mean FVIII antigen concentration in plasma is significantly higher (30%) than that reported by the activity-based assay (0.7 nM) (Girma et al., 1998; Hoyer, 1981; Hoyer, 1994; Hubbard and Heath, 2004; Ingerslev et al., 2004).

Figures 26A, 26B:
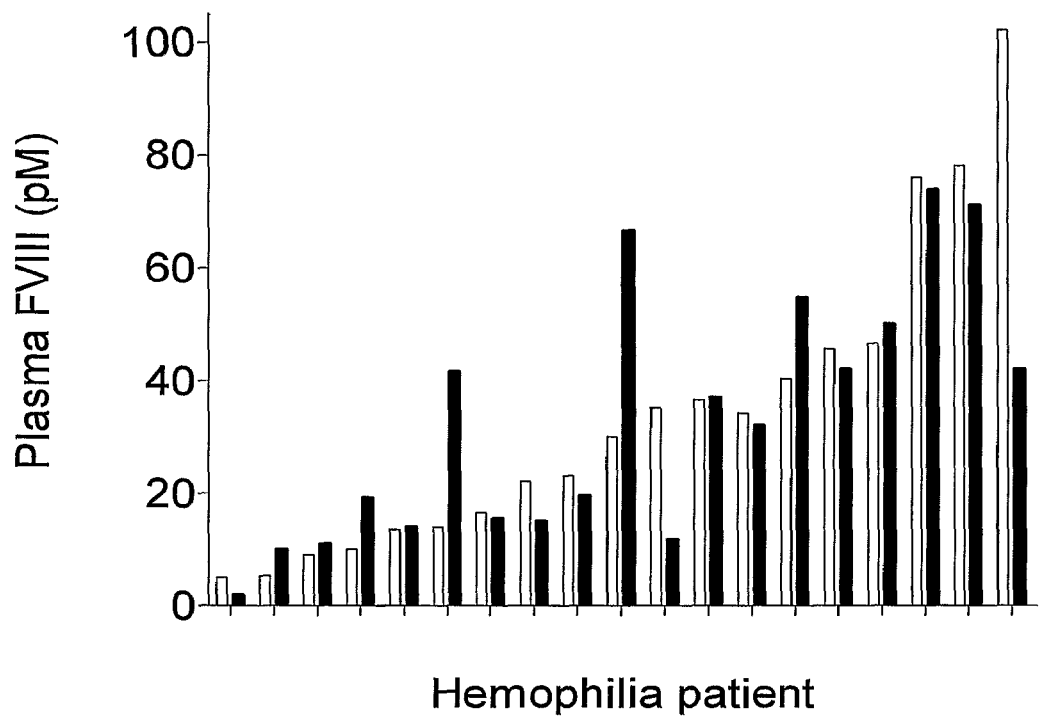
FIG. 26A is a bar graph showing a comparison of plasma FVIII concentrations in patients with hemophilia, as measured by FLI and APTT assay.
FIG. 26B is a graph showing the relationship between FVIII antigen concentration in hemophilia patients as measured by FL and APTT.

To determine the assay dynamics and sensitivity to variations in FVIII concentration, plasma FVIII concentrations were determined for plasmas from severe, moderate and mild hemophilia patients (n=19) with wide ranges of FVIII concentration. FIG. 26A illustrates the results of FVIII antigen concentration in hemophilia in comparison to that obtained by our in house APTT assay. Comparison of plasma FVIII concentrations of hemophilia patients is indicated by FLI (□) and APTT (■). For FLI, plasmas were diluted 2-fold in immunodepleted plasma, reduced with 10 mM BME and subjected to FLI. FVIII antigen concentrations were determined from a calibration graph of rFVIII similar to that shown in FIG. 24B. For APTT, plasmas were used undiluted. APTT calibrator was generated by spiking rFVIII into FVIII-immunodepleted plasma (Precision Biologics). FIG. 26B illustrates relationships between FVIII antigen concentration as determined by FLI and APTT (4 patients whose APTT and FLI did not correlate were excluded).

In both assays calibration curves were generated by spiking rFVIII into a single lot of FVIII-immunodepleted plasma from the commercial source (Precision Biologic). Comparison of FLI results with the results of APTT indicated that in general there is a good correlation between FVIII concentration determined by FLI and that determined by APTT in hemophilia patients. However, in two patients (10%), antigen concentration appeared to be significantly higher (>2-fold) than FVIII concentration by APTT and in two patients (10%), FVIII concentration by APTT was significantly higher (>2-fold) than FVIII antigen (FIG. 26A). With the exception of these four patients, there was a linear correlation between FVIII antigen concentration (FLI) and FVIII activity (APTT) (Pearson r>0.97, R squared 0.94) (FIG. 26B).

Figure 27:
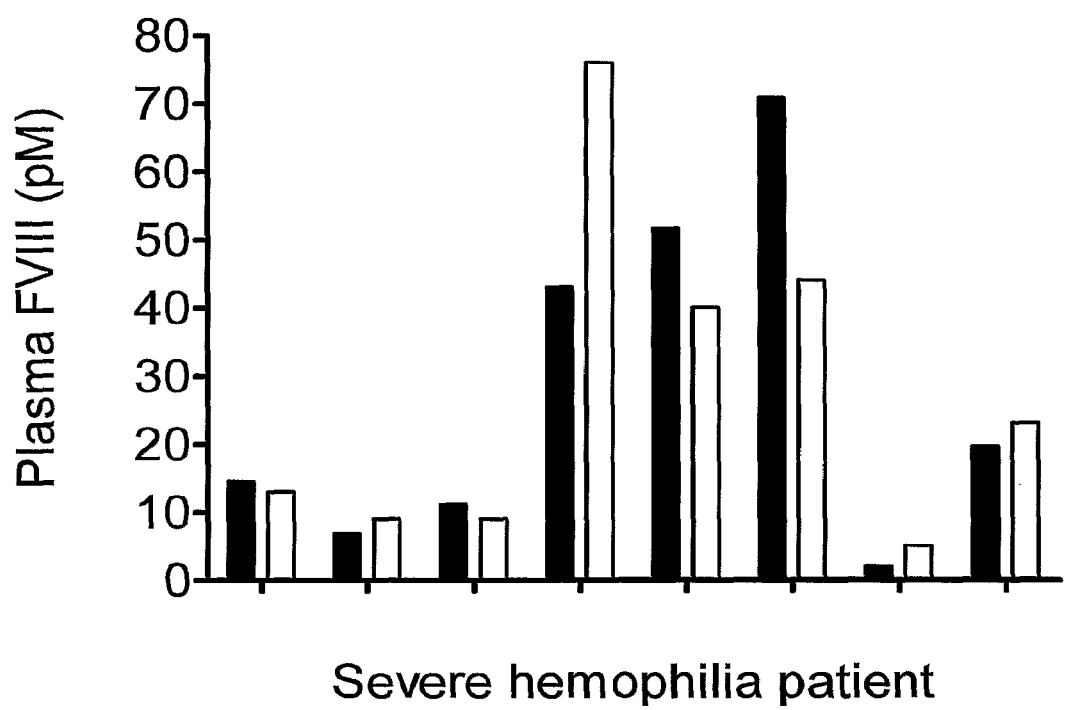
FIG. 27 is a bar graph showing correlation between FVIII antigen concentration in severe hemophilia patients (n=8) as measured by FLI and APTT assays.

FIG. 27 illustrates FVIII antigen concentration ranges (FLI) in comparison to FVIII concentration by APTT in severe hemophilia (n=8). A large scope of FVIII concentrations ranging from 5 pM to 76 pM could be readily detected, emphasizing the sensitivity of the FLI to variations in FVIII concentration (FIG. 27).

Figure 28A:
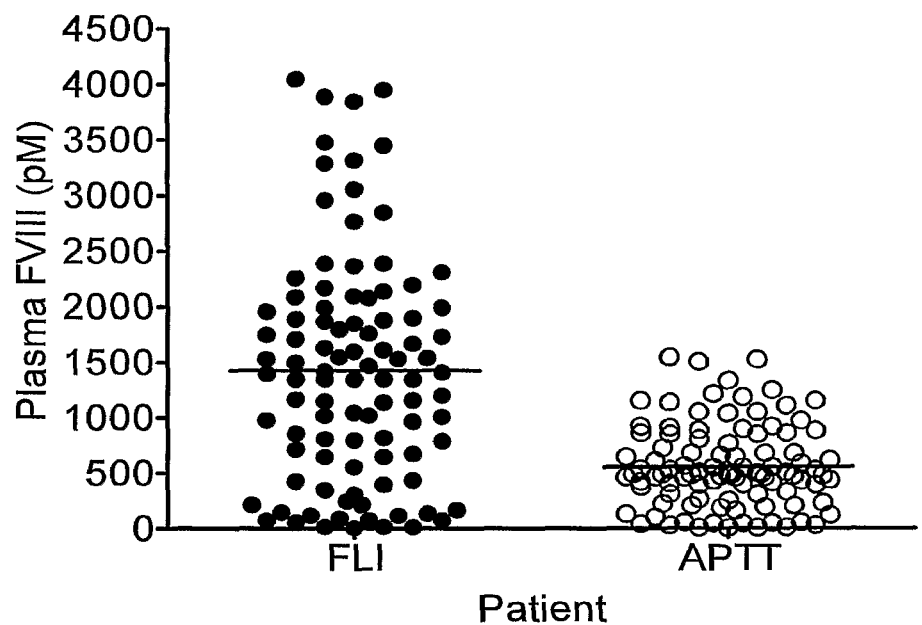
FIG. 28A is two plots showing FVIII concentrations and ranges in patients (n=100) with diseases including autoimmune disorders and FVIII deficiency, as determined by FLI and APTT assays.
Figure 28B:
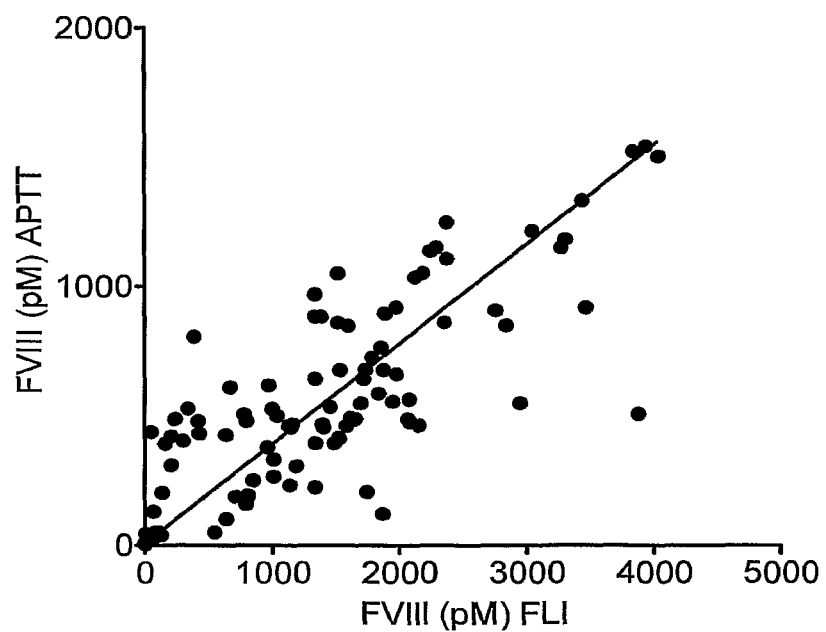
FIG. 28B is a graph showing correlation between measurements of plasma FVIII concentration as determined by FLI and APTT assays.

Additional studies were performed on plasmas from children (n=100) with various pathological conditions including hemophilia patients and patients with autoimmune disorders (FIG. 28). More particularly, comparison of FVIII concentrations and ranges in patients (n=100) with various diseases (including autoimmune and FVIII deficiency) determined by FLI and APTT is shown in FIG. 28A. For FLI (●), plasmas were diluted 2-fold in FVIII-depleted plasma and an additional 2-fold with PBS buffer, reduced with 10 mM BME, diluted further 4-, 10 and 20-fold and subjected to FLI. FVIII concentrations were determined from high range calibrator similar to that shown in FIG. 24A. For APTT (○), plasmas were diluted 5- and 10-fold in FVIII-immunodepleted plasma (Precision Biologic) and subjected to APTT. APTT calibrator was generated by spiking rFVIII (FIGS. 28A and 28B) or Immunate into FVIII-depleted plasma (Precision Biologic). FIG. 28B shows correlation between plasma FVIII concentration by FLI and APTT.

The patient populations included those with a significant amount of auto- and anti-coagulant antibodies. Results illustrated in FIG. 28 indicate that there are significant variations in FVIII concentration among these patients and that FLI is sensitive to low as well as high FVIII concentrations over a range of >3 orders of magnitude (2-4000 pM, FIG. 28A). When the results of FVIII antigen concentration were compared to our in house APTT, mean FVIII concentration by FLI was 2.6-fold higher (1424±1024 pM) than the FVIII concentration by APTT (556±375). These data show that plasma FVIII concentration is 39% higher by FLI as compared to APTT, consistent with our FVIII results for 44 healthy individuals, showing that the concentration of plasma FVIII by FLI is 30% higher than that obtained by APTT. Despite significant variations in FVIII concentration among patients, there is a linear correlation between the results of FLI and APTT with Pearson r of 0.8 (R squared 0.64).

Figure 29A:
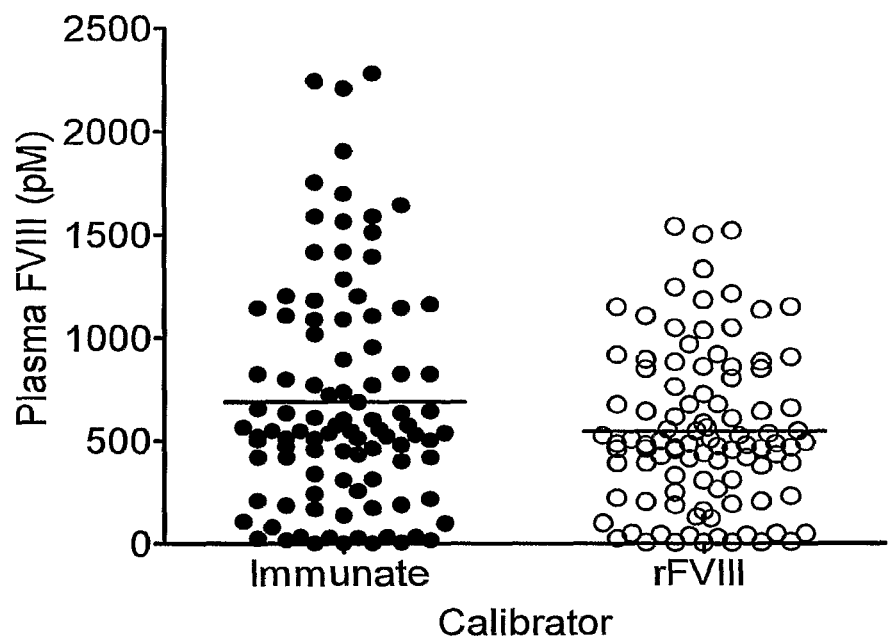
FIG. 29A is two plots showing a comparison of plasma FVIII concentrations calculated from rFVIII and Immunate calibrators.
Figure 29B:
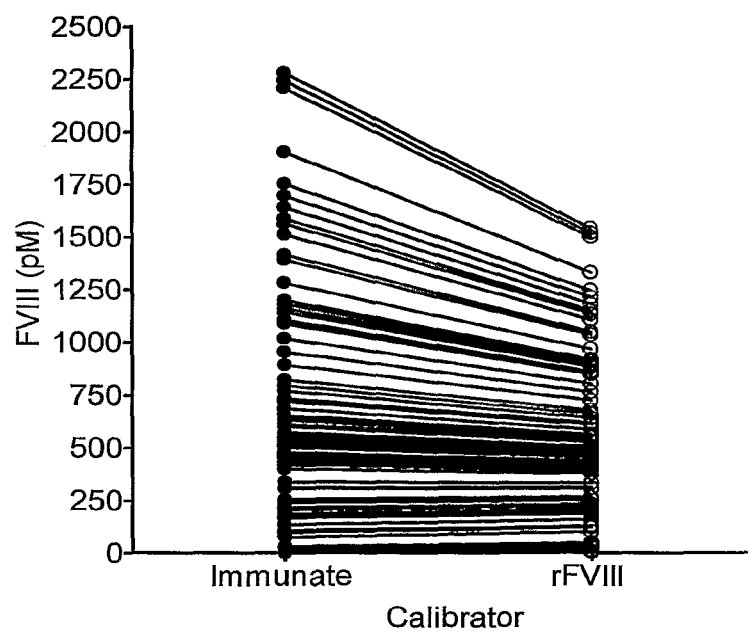
FIG. 29B is a graph showing a comparison of FVIII concentrations as determined using the two calibrators.

Our APTT assay was performed with a FVIII immunodepleted plasma substrate that was also depleted of vWF. In order to determine whether absence of vWF could result in significant differences between FVIII antigen results (FLI) and those obtained by APTT (FIG. 28B), we used Immunate as FVIII calibrator. The concentration of Immunate was verified by ELISA, FLI and 1:1 functional stoichiometry (Butenas et al., 2004; Parhami-Seren et al., 2004). Immunate contained 40-fold molar excess molar of vWF, as established by ELISA. FIG. 29A illustrates the results of plasma FVIII concentration determination using either rFVIII or Immunate as calibrator. FIG. 29A shows a comparison of plasma FVIII concentrations calculated from rFVIII (○) and Immunate (●) calibrators. FIG. 29B is a comparison between FVIII concentrations calculated from rFVIII (○) or Immunate (●) calibrators showing that at concentrations below 1000 pM, there is no significant difference between the results of these two calibrators. At concentrations above 1000 pM, the Immunate calibrator gives 25% higher FVIII concentrations by APTT as compared to rFVIII calibrator.

As discussed, there was no significant difference between FVIII concentrations of up to 1000 pM when either calibrator was used. However, at FVIII concentrations>1000 pM Immunate calibrator, FVIII concentrations were slightly (25%) higher in comparison to the FVIII results obtained from the rFVIII calibrator (FIGS. 29A and 29B). This indicates that at high FVIII concentrations, absence or presence of vWF results in slight differences in the results of FVIII concentration determination.

These data indicate that FLI can detect FVIII concentrations significantly below 1% physiological concentration (detection limit 2 pM, ~0.16-0.2% FVIII based on 1-1.2 nM FVIII mean physiological concentration obtained by FLI and by ELISA. FLI also quantifies FVIII at concentrations between 2-4000 pM (3 orders of magnitude); thus FLI should facilitate quantitative measurements of FVIII in healthy individuals, in individuals with prothrombotic conditions due to high concentration of FVIII, and severe hemophilia patients and patients receiving FVIII replacement.

FVIII concentrations obtained by FLI were compared with those obtained by activated partial thromboplastin time (APTT). FLI exhibited large dynamics by detecting FVIII concentrations in severe, moderate and mild hemophilia ranging between 0-4.5 nM. This assay will not only permit FVIII antigen quantitation and further classification of severe hemophilia patients, but it can also be useful in pharmacokinetic studies involving FVIII replacement.

In summary, we have developed a specific and sensitive assay format by which plasma FVIII can be quantified at concentrations as low as 2 pM. Integration of FVIII ELISA with LMAP technology allows quantitation of plasma at concentrations significantly below 1% physiological concentration. Such sensitivity could not be achieved by conventional ELISA.

Our data using this highly sensitive assay show that the mean value for plasma FVIII antigen in healthy population is about 30% higher (1.0 nM) than that reported by activity assay (0.7 nM) (Girma et al., 1998; Hoyer, 1981; Hoyer, 1994; Hubbard and Heath, 2004; Ingerslev et al., 2004) although significant variations in FVIII levels were observed among healthy individuals. The sensitivity and large dynamics of the assay is evident by its ability to quantify a low range of plasma FVIII from patients with severe hemophilia patients (FIG. 27). FVIII concentrations in all experiments were determined from the standard curve of rFVIII; thus plasma FVIII concentrations reported here are fundamental measurements of mass of FVIII across healthy and hemophilia populations as well as population with diverse diseases.

The FLI described herein provides an important tool for precise determination of FVIII concentration for the diagnosis of FVIII deficiencies (genetic vs. production of non-functional FVIII protein) and management of hemophilia A.

REFERENCES

It is believed that a review of the references will increase appreciation of the present invention. In some instances, the references are prefaced by a number in parentheses referred to in the specification.

Barrowcliffe, T. W., Raut, S., Sands, D. and Hubbard, A. R. (2002) Coagulation and chromogenic assays of factor VIII activity: general aspects, standardization, and recommendations. Semin. Thromb. Haemost. 28, 247-255.

Bihoreau, N., Paolantonacci, P., Bardelle, C., Fontaine-Aupart, M.-P., Krishnan, S., Yon, J. and Romet-Lemonne, J.-L. (1991) Structural and functional characterization of Factor VIII-dII, a new recombinant Factor VIII lacking most of the B-domain. Biochem. J. 277, 23-31.

Brackmann, H. H., Aygoren, E., Scharrer, I., Schwaab, R., Hammerstein, U. and Oldenburg, J. (1993) Two years' experience with two recombinant factor VIII concentrate. Blood Coagul. Fibrinolysis 4, 421-424.

Butenas, S., van't Veer, C. and Mann, K. G. (1999) "Normal" thrombin generation. Blood 94, 2169-2178.

Chavin, S. T. and Fay, P. J. (1989) The purification, Structure and Function of Factor VIII. CRC Press, Boca Raton, Fla.

El Alfy, M. S., Tantawy, A. A., Ahmed, M. H. and Abdin, I. A. (2000) Frequency of inhibitor development in severe haemophilia A children treated with cryoprecipitate and low-dose immune tolerance induction. Haemophilia 6, 635-638.

Fay, P. J. (1993) Factor VIII Structure and Function. Thromb. Haemost. 70, 63-67.

Foster, P. A. and Zimmerman, T. S. (1989) Factor VIII structure and function. Blood Reviews 3, 180-191.

Foster, W. B., Katzmann, J. A., Miller, R. S., Nesheim, M. E. and Mann, K. G. (1982) Monoclonal antibodies selective for the functional states of bovine factor V and factor Va. Thromb. Res. 28, 649-661.

Foster, W. B., Tucker, M. M., Katzmann, J. A., Miller, R. S., Nesheim, M. E. and Mann, K. G. (Blood) Monoclonal antibodies to human coagulation factor V and factor Va. Blood 61, 1060-1067.

Hoyer, L. W. (1981) The factor VIII complex: structure and function. Blood 58, 1-13. Kane, W. H. and Davie, E. W. (1988) Blood coagulation factors V and VIII: structural and functional similarities and their relationship to hemorrhagic and thrombotic disorders. Blood 71, 539-555.

Kemball-Cook, G., Tubbs, J. E., Dawson, N. J. and Barrowcliffe, T. W. (1993) The behavior of different factor VIII concentrates in a chromogenic factor X-activating system. Brit. J. Haematol. 84, 273-278.

Kleinveld, H. A., Anderson, N. E., van Voorthuiozen, H., den Hartog, J. and de Groot, P. G. (1999) Determination of coagulation FVIII activity by chromogenic substrate method on STA, an automated coagulation analyzer. Scans. J. Clin. Invest. 59, 335-341.

Klinge, J., Auerswald, G., Budde, U., Klose, H., Kreuz, W., Lenk, H. and Scandella, D. (2001) Paediatric Inhibitor Study Group of the German Society on Thrombosis and Haemostasis. Detection of all anti-factor VIII antibodies in haemophilia A patients by the Bethesda assay and a more sensitive immunoprecipitation assay. Haemophilia 7, 26-32.

Langdell, R. D., Wagner, R. H. and Brinkhous, K. M. (1953) Effect of antihemophilic factor on one-stage clotting tests. A presumptive assay for hemophilia and a simple one-stage antihemophilic factor assay procedure. J. Lab. Clin. Med. 41, 637-647.

Lenting, P. J., van Mourik, J. A. and Mertens, K. (1998) The life cycle of factor VIII in view of its structure and function. Blood 92, 3983-3996.

Lindgren, A., Wadenvik, H. and Tengborn, L. (2002) Characterization of inhibitors to FVIII with an ELISA in congenital and aquired haemophilia A. Haemophilia 8, 644-

648. Lollar, P., Fay, P. J., and Fass, D. N. (1993) Factor VIII and Factor VIIIa. Methods in Enzymology:128-143.

Lundblad, R. L., Kingdon, H. S., Mann, K. G. and White, G. C. (2000) Issues with the assay of FVIII activity in plasma and factor VIII concentrates. Thromb. Haemost. 84, 942-948. Lusher, J. M., Arkin, S., Abildgaard, C. F. and Schwartz, R. S. (1993) Recombinant factor VIII for the treatment of previously untreated patients with hemophilia A. Safety, efficacy, and development of inhibitors. Kogenate Previously Untreated Patient Study Group. N Engl J Med. 328, 453-459.

Lusher, J. M., Hillman-Wiseman, C. and Hurst, D. (1998) In vivo recovery with products of very high purity-assay discrepancies. Haemophilia 4, 641-645.

Mikaelsson, M., Oswaldson, U. and Jankowski, M. A. (2001) Measurement of FVIII activity of B-domain deleted recombinant factor VIII. Semin. Hematol. 38 (Suppl. 4), 13-23.

Mikaelsson, M. and Oswaldsson, U. (2002) Assaying the cirulating factor VIII activity in hemophilia A patients treated with recombinant factor VIII products. Semin. Thromb. Haemost. 28, 257-264.

Mikaelsson, M., Oswaldsson, U. and Sandberg, H. (1998) Influence of phospholipids on the assessment of factor VIII activity. Haemophilia. 4, 646-650.

Niemetz, J. and Nossel, H. L. (1969) Activated coagulation factors: In vivo and in vitro studies. Brit. J. Haematol. 16, 337-351.

Over, J. (1986) Methodology of the one-stage assay of factor VIII (VIII:C). Scand. J. Haematol. 33 (Suool. 41), 13-24.

Pipe, S. W. and Kaufman, R. J. (1997) Characterization of a genetically engineered inactivation-resistant coagulation factor VIIIa. Proc. Natl. Acad. Sci. USA 94, 11851-11856.

Rick, M. E., Walsh, C. E. and Key, N. S. (2003) Congenital bleeding disorders. Hematology (Am Soc Hematol Educ Program)., 559-574.

Sandberg, H., Almstedt, A., Brandt, J., Gray, E., Holmquist, L., Oswaldsson, U., Sebring, S. and Mikaelsson, M. (2001) Structural and functional characteristics of the B-domain-deleted recombinant factor VIII protein, rFVIII SQ. Thromb. Haemost. 85, 93-100.

Scandella, D., Mondorf, W. and Klinge, J. (1998) The natural history of the immune response to exogenous factor VIII in severe haemophilia A. Haemophilia 4, 546-551.

1. Lundblad R L, Kingdon H S, Mann K G, White G C. Issues with the assay of FVIII activity in plasma and factor VIII concentrates. Thromb Haemost 2000; 84:942-948.
2. Hubbard A R, Bevan S A, Weller L J. Potency estimation of recombinant factor VIII: effect of assay method and standard. Br J Haematol 2001; 113:533-536.
3. Over J. Methodology of the one-stage assay of factor VIII (VIII:C). Scand J Haematol. 1986; 33 (Suool. 41):13-24.
4. Langdell R D, Wagner R H, Brinkhous K M. Effect of antihemophilic factor on one-stage clotting tests. A presumptive assay for hemophilia and a simple one-stage antihemophilic factor assay procedure. J Lab Clin Med 1953; 41:637-647.
5. Niemetz J, Nossel H L: Activated coagulation factors. In vivo and in vitro studies. Brit J Haematol 1969; 16:337-351.
6. Kemball-Cook G, Tubbs J E, Dawson N J, Barrowcliffe T W. The behavior of different factor VIII concentrates in a chromogenic factor X-activating system. Brit J Haematol 1993; 84:273-278.
7. Hoyer L W. The factor VIII complex: structure and function. Blood 1981; 58:1-13.
8. Kane W H, Davie E W. Blood coagulation factors V and VIII: structural and functional similarities and their relationship to hemorrhagic and thrombotic disorders. Blood 1988; 71:539-555.
9. Chavin S T, Fay P J. The purification, Structure and Function of Factor VIII. Boca Raton, Fla., CRC Press, 1989.
10. Lenting P J, van Mourik J A, Mertens K. The life cycle of factor VIII in view of its structure and function. Blood 1998; 92:3983-3996.
11. Kleinveld H A, Anderson N E, van Voorthuiozen H, den Hartog J, de Groot P G. Determination of coagulation FVIII activity by chromogenic substrate method on STA, an automated coagulation analyzer. Scans J Clin Invest 1999; 59:335-341.
12. Mikaelsson M, Oswaldson U, Jankowski M A. Measurement of FVIII activity of B-domain deleted recombinant factor VIII. Semin Hematol 2001; 38 (Suppl. 4):13-23.
13. Barrowcliffe T W, Raut S, Sands D, Hubbard A R. Coagulation and chromogenic assays of factor VIII activity: general aspects, standardization, and recommendations. Semin Thromb Haemost 2002; 28:247-255.
14. Mikaelsson M, Oswaldsson U. Assaying the cirulating factor VIII activity in hemophilia A patients treated with recombinant factor VIII products. Semin Thromb Haemost 2002; 28:257-264.
15. Mikaelsson M, Oswaldsson U, Sandberg H. Influence of phospholipids on the assessment of factor VIII activity. Haemophilia 1998; 4:646-650.
16. Lusher J M, Hillman-Wiseman C, Hurst D. In vivo recovery with products of very high purity-assay discrepancies. Haemophilia 1998; 4:641-645.
17. Lu D, Kalafatis M, Mann K G, Long G L. Comparison of activated protein C/protein S-mediated inactivation of human factor VIII and factor V. Blood 1996; 87:4708-4717.
18. Butenas S, van't Veer C, Mann K G. "Normal" thrombin generation. Blood 1999; 94:2169-2178.
19. Scandella D, Mondorf W, Klinge J. The natural history of the immune response to exogenous factor VIII in severe haemophilia A. Haemophilia 1998; 4:546-551.
20. Rick M E, Walsh C E, Key N S. Congenital bleeding disorders. Hematology (Am Soc Hematol Educ Program). 2003:559-574.
21. Hoyer L W. Medical progress-Hemophilia A. N Engl J Med 1994; 330:38-47.
22. Olson J D, Brockway W J, Fass D N, Bowie E J, Mann K G. Purification of porcine and human ristocetin-Willebrand factor. J Lab Clin Med 1977; 89:1278-1294.
23. Sadler J E, Davie E W. The molecular basis of blood diseases. Philadelphia, W. B. Saunders, 1987.
24. Lollar P, Fay P J, Fass D N. Factor VIII and factor VIIIa. Methods Enzymol 1993; 222:128-143.
25. Butenas S, Parhami-Seren B, Gissel M T, Gomperts E D, Mann K G. Activity and content of factor VIII in various FVIII products. J Thromb Haemost 2005; 3:Supplement 1 (Abstract#2028).
26. Foster W B, Tucker M M, Katzmann J A, Miller R S, Nesheim M E, Mann K G. Monoclonal antibodies to human coagulation factor V and factor Va. Blood 1983; 61:1060-1067.
27. Precup J W, Kline B C, Fass D N. A monoclonal antibody to factor VIII inhibits von Willebrand factor binding and thrombin cleavage. Blood 1991; 77:1929-1936.
28. Parhami-Seren B, Butenas S, Amblo J, Fass D N, Mann K G. Quantitation of FVIII antigen in human plasma. J Thromb Haemost 2005; 3: Supplement 1 (Abstract#650).

29. Pace C N, Vajdos F, Fee L, Grimsley G, Gray T. How to measure and predict the molar absorption coefficient of a protein. Protein Sci 1995; 4:2411-2423.
30. Kumar H, Healey J F, Lollar P, Durrani M J. Determination of free sulfhydryls in human factor VIII. J Thromb Haemost 2003; 1 (Supplement 1):P1067.
31. Parhami-Seren B, Butenas S, Amblo J, Mann K G. Immunologic quantitation of tissue factors. J Thromb Haemost 2006; 4:1-6.
32. Girma J P, Fressinaud E, Houllier A, Laurian Y, Amiral J, Meyer D. Assay of factor VIII antigen (VIII:CAg) in 294 haemophilia A patients by a new commercial ELISA using monoclonal antibodies. Haemophilia 1998; 4:98-103.
33. Ingerslev J, Jankowski M A, Weston S B, Charles L A. Collaborative field study on the utility of a BDD factor VIII concentrate standard in the estimation of BDDr Factor VIII:C activity in hemophilic plasma using one-stage clotting assays. J Thromb Haemost 2004; 2:623-628.
34. Hubbard A R, Heath A B. Standardization of factor VIII and von Willebrand factor in plasma: calibration of the WHO 5th International Standard (02/150). J Thromb Haemost 2004; 2:1380-1384.
35. Nogami K, Wakabayashi H, Fay P J. Mechanisms of factor Xa-catalyzed cleavage of the factor VIIIa A1 subunit resulting in cofactor inactivation. J Biol Chem 2003; 278: 16502-16509.
36. Fay P J, Beattie T L, Regan L M, O'Brien L M, Kaufman R J. Model for the factor VIIIa-dependent decay of the intrinsic factor Xase. Role of subunit dissociation and factor IXa-catalyzed proteolysis. J Biol Chem 1996; 271: 6027-6032.
37. Parker E T, Doering C B, Lollar P. A1 Subunit-mediated Regulation of Thrombin-activated Factor VIII A2 Subunit Dissociation. J Biol Chem 2006; 281:13922-13930.
38. Hockin M F, Jones K C, Everse S J, Mann K G. A model for the stoichiometric regulation of blood coagulation. J Biol Chem 2002; 277:18322-18333.
39. Lawson J H, Kalafatis M, Stram S, Mann K G. A model for the tissue factor pathway to thrombin. I. An empirical study. J Biol Chem 1994; 269:23357-23366.
40. Kalashnikova L A, Berkovskii A L, Dobrynina L A, Sergeeva E V, Kozlov A A, Aleksandrova E N, Nasonov E L. [Clotting factor VIII in Sneddon syndrome]. Klin Med (Mosk) 2003; 81:42-45.
41. Hoppener M R, Kraaijenhagen R A, Hutten B A, Buller H R, Peters R J, Levi M. Beta-receptor blockade decreases elevated plasma levels of factor VIII:C in patients with deep vein thrombosis. J Thromb Haemost 2004; 2:1316-1320.
42. Tripodi A, Chantarangkul V, Martinelli I, Bucciarelli P, Mannucci P M. A shortened activated partial thromboplastin time is associated with the risk of venous thromboembolism. Blood 2004; 104:3631-3634.
43. Conley C L. Disorders of the blood in disseminated lupus erythematosus. Am J Med 1952; 13:1-2.
44. Conley C L, Hartmann R C. A hemorrhagic disorder caused by circulating anticoagulant in patients with disseminated lupus erythematosus. J Clin Invest 1952; 31:621-622.
45. Andersson L O, Forsman N, Huang K, Larsen K, Lundin A, Pavlu B, Sandberg H, Sewerin K, Smart J. Isolation and characterization of human factor VIII: molecular forms in commercial factor VIII concentrate, cryoprecipitate, and plasma. Proc Natl Acad Sci USA 1986; 83:2979-2983.

Butenas S., Parhami-Seren B., Gissel M. T., Gomperts E. D. and Mann K. G. (2004) Quantitative evaluation of factor VIII in factor VIII products. Blood 104, 89b (Abstract#4012).
Butenas S., Parhami-Seren B., Gissel M. T., Gomperts E. D. and Mann K. G. (2005) Activity and content of factor VIII in various FVIII products. J. Thromb. Haemost. 3, Supplement 1 (Abstract#2028).
Chuah M. K., Collen D. and Vandendiressche T. (2004) Preclinical and clinical gene therapy for haemophilia. Haemophilia 4, 119-125.
Fay P. J., Beattie T. L., Regan L. M., O'Brien L. M. and Kaufman R. J. (1996) Model for the factor VIIIa-dependent decay of the intrinsic factor Xase. Role of subunit dissociation and factor IXa-catalyzed proteolysis. J. Biol. Chem. 271, 6027-6032.
Gilchrist G. S., Wilke J. L., Muehlenbein L. R. and Danilenko-Dixon D. (2001) Intrauterine correction of factor VIII (FVIII) deficiency. Haemophilia 7, 497-499.
Girma J. P., Fressinaud E., Houllier A., Laurian Y., Amiral J. and Meyer D. (1998) Assay of factor VIII antigen (VIII:CAg) in 294 haemophilia A patients by a new commercial ELISA using monoclonal antibodies. Haemophilia 4, 98-103.
Hawkins T. E., Green G. J., Romeril K., Milicih G. S, and Carter J. M. (1995) Treatment of Haemophilia A by continuous factor VIII infusion. Aus. NZ J. Med. 25, 37-39.
Hockin M. F., Jones K. C., Everse S. J. and Mann K. G. (2002) A model for the stoichiometric regulation of blood coagulation. J Biol Chem 277, 18322-33.
Hoyer L. W. (1994) Medical progress-Hemophilia A. N. Engl. J. Med. 330, 38-47.
Hubbard A. R. and Heath A. B. (2004) Standardization of factor VIII and von Willebrand factor in plasma: calibration of the WHO 5th International Standard (02/150). J. Thromb. Haemost. 2, 1380-1384.
Hurst D., Zabor S., Malianni D. and Miller D. (1998) Evaluation of recombinant factor VIII (KogenateR) stability for continuous infusion using a minipump infusion device. Haemophilia 4, 785-789.
Ingerslev J., Jankowski M. A., Weston S. B. and Charles L. A. (2004) Collaborative field study on the utility of a BDD factor VIII concentrate standard in the estimation of BDDr Factor VIII:C activity in hemophilic plasma using one-stage clotting assays. J. Thromb. Haemost. 2, 623-628.
Kane W. H. and Davie E. W. (1988) Blood coagulation factors V and VIII: structural and functional similarities and their relationship to hemorrhagic and thrombotic disorders. Blood 71, 539-555.
Kumar H., Healey J. F., Lollar P. and Durrani M. J. (2003) Determination of free sulfhydryls in human factor VIII. J. Thromb. Haemost. 1 (Supplement 1), P1067.
Lawson J. H., Kalafatis M., Stram S, and Mann K. G. (1994) A model for the tissue factor pathway to thrombin. I. An empirical study. J Biol Chem 269, 23357-66.
Lindgren A., Wadenvik H. and Tengborn L. (2002) Characterization of inhibitors to FVIII with an ELISA in congenital and aquired haemophilia A. Haemophilia 8, 644-648.
Nogami K., Wakabayashi H. and Fay P. J. (2003) Mechanisms of factor Xa-catalyzed cleavage of the factor VIIIa A1 subunit resulting in cofactor inactivation. J. Biol. Chem. 278, 16502-16509.
Pace C. N., Vajdos F., Fee L., Grimsley G. and Gray T. (1995) How to measure and predict the molar absorption coefficient of a protein. Protein Sci 4, 2411-23.

Parhami-Seren B., Butenas S., Amblo J. and Mann K. G. (2006) Immunologic quantitation of tissue factors. J. Thromb. Haemost. 4, 1-6.

Parhami-Seren B., Butenas S., Bouchard B., Amblo J. and Mann K. G. (2004) Quantitation of natural, recombinant, cell-surface and plasma tissue factor. Blood 104, 533a (Abstract#1929).

Petrini P. (2001) What factors should influence the dosage and interval of prophylactic treatment in patients with severe haemophilia A and B? Haemophilia 7, 99-102.

Precup J. W., Kline B. C. and Fass D. N. (1991) A monoclonal antibody to factor VIII inhibits von Willebrand factor binding and thrombin cleavage. Blood 77, 1929-36.

Roth D. A., Tawa N. E., Jr., O'Brien J. M., Treco D. A. and Selden R. F. (2001) Nonviral transfer of the gene encoding coagulation factor VIII in patients with severe hemophilia A. N Engl J Med 344, 1735-42.

Sadler J. E. and Davie E. W. (1987) The molecular basis of blood diseases. W. B. Saunders, Philadelphia.

Tackaberry E. S., Ganz P. R. and Rock G. (1987) Measurement of human factor VIII by avidin-biotin dot immunobinding ELISAs. J. Immunol. Methods 99, 59-66.

The disclosures of all references cited herein are incorporated herein by reference. The invention has been described in detail with reference to preferred embodiments thereof.

However, it will be appreciated that those skilled in the art, upon consideration of this disclosure, may make modifications and improvements within the spirit and scope of the invention.

What is claimed is:

1. A method for determining the level of a FVIII protein or a fragment thereof in a sample, comprising:
   (a) contacting the sample with a first antibody directed to a FVIII antigen, said first antibody being attached to a first bead having at least one first characteristic, wherein the FVIII protein or fragment thereof comprising said FVIII antigen binds to said first antibody being attached to the first bead, thereby forming a capture antibody, and forms a complex therewith;
   (b) contacting the sample with a control antibody not directed to a FVIII antigen, said control antibody being attached to a second bead having at least one second characteristic distinguishable from the first characteristic of the first bead, wherein one or more proteins in the sample may form non-specific complexes with the control antibody;
   (c) contacting the complexes formed in steps (a) and (b) with a second antibody directed to the FVIII antigen, said second antibody being labeled with a marker, to form a complex which includes the antibody of step (a) or (b), the FVIII protein or fragment thereof comprising said FVIII antigen, and the second antibody; and
   (d) subtracting the quantity of the second labeled antibody in complexed associated with the second beads attached to the control antibody from the quantity of the second labeled antibody in complexes associated with the first beads attached to the first antibody directed against the FVIII antigen, thereby removing spurious non-specific binding and more accurately determining the level of the FVIII protein or fragment thereof comprising said antigen in the sample.

2. The method of claim 1, wherein the sample comprises plasma.

3. The method of claim 1, wherein the sample comprises plasma obtained from a human having or at risk of developing a blood clotting disorder.

4. The method of claim 1, wherein the sample is a pharmaceutical product comprising FVIII protein obtained from human blood.

5. The method of claim 1, wherein the sample comprises recombinant FVIII protein.

6. The method of claim 1, wherein the first antibody can bind to FVIII under conditions wherein FVIII is dissociated from von Willebrand factor.

7. The method of claim 1, wherein an epitope recognized by the first antibody resides in the L-chain of FVIII.

8. The method of claim 7, wherein the first antibody is anti-FVIII-68 mAb, deposited under ATCC Accession No. PTA-6891.

9. The method of claim 1, wherein an epitope recognized by the second antibody resides in the H/L-chain of FVIII.

10. The method of claim 9, wherein the second antibody is anti-FVIII-24 mAb, deposited under ATCC Accession No. PTA-6890.

11. The method of claim 1, wherein the determined level of FVIII protein in the sample is between about 0.001 nM and 1000 nM.

12. The method of claim 1, wherein the first antibody is anti-FVIII-68 mAb and the second antibody is anti-FVIII-24 mAb.

13. The method of claim 1, further comprising prior to step (a) contacting the sample with a reducing agent that releases FVIII from a FVIII-binding molecule, wherein the reducing agent is selected from the group consisting of β-mercaptoethanol, sodium borohydride, dithiothreitol, erytritol, and ethane thiol.

14. An isolated antibody directed to FVIII protein, wherein the epitope recognized by said antibody resides in the H/L-chain of FVIII antigen, said antibody having a binding affinity ($IC_{50}$) in the range of about 50-100 nM.

* * * * *